(12) United States Patent
Eide

(10) Patent No.: US 7,559,898 B2
(45) Date of Patent: Jul. 14, 2009

(54) METHOD FOR ANALYSIS OF SINGLE PULSE PRESSURE WAVES

(75) Inventor: Per Kristian Eide, Oslo (NO)

(73) Assignee: DPCOM AS, Oslo (NO)

(*) Notice: Subject to any disclaimer, the term of this patent is extended or adjusted under 35 U.S.C. 154(b) by 983 days.

(21) Appl. No.: 10/613,112

(22) Filed: Jul. 7, 2003

(65) Prior Publication Data
US 2004/0087863 A1    May 6, 2004

Related U.S. Application Data

(60) Provisional application No. 60/422,111, filed on Oct. 30, 2002.

(30) Foreign Application Priority Data
Jul. 2, 2003    (NO) ..................... PCT/NO03/00229

(51) Int. Cl.
*A61B 5/00* (2006.01)
(52) U.S. Cl. ...................... 600/485; 600/500
(58) Field of Classification Search .................... None
See application file for complete search history.

(56) References Cited

U.S. PATENT DOCUMENTS 5,755,229 A * 5/1998 Amano et al. ............... 600/500

* cited by examiner

*Primary Examiner*—Robert L Nasser
(74) *Attorney, Agent, or Firm*—Birch, Stewart, Kolasch & Birch, LLP

(57) ABSTRACT

This invention relates to a method for analysing pressure-signals derivable from pressure measurements on or in a body of a human being or animal, comprising the steps of identifying during given time sequences in a series of time sequences the single pressure waves, including related parameters [pressure amplitude ΔP latency (ΔT), rise time coefficient (ΔP/ΔT)], determining numbers of single pressure waves with pre-selected combinations of two or more of said single pressure wave parameters during said time sequence. For the time sequences is further determined the balanced positions of single wave parameters. Two-dimensional values of balanced position may be presented as a one dimensional value after weighting of the matrix cells. The signal processing method may be used for more optimal detection of single pressure waves by means of non-invasive sensor devices.

93 Claims, 12 Drawing Sheets

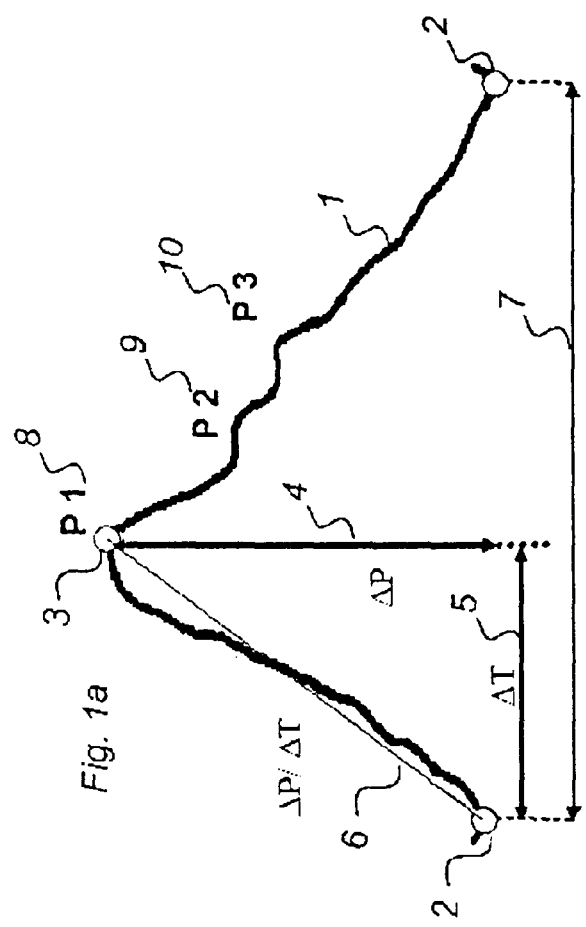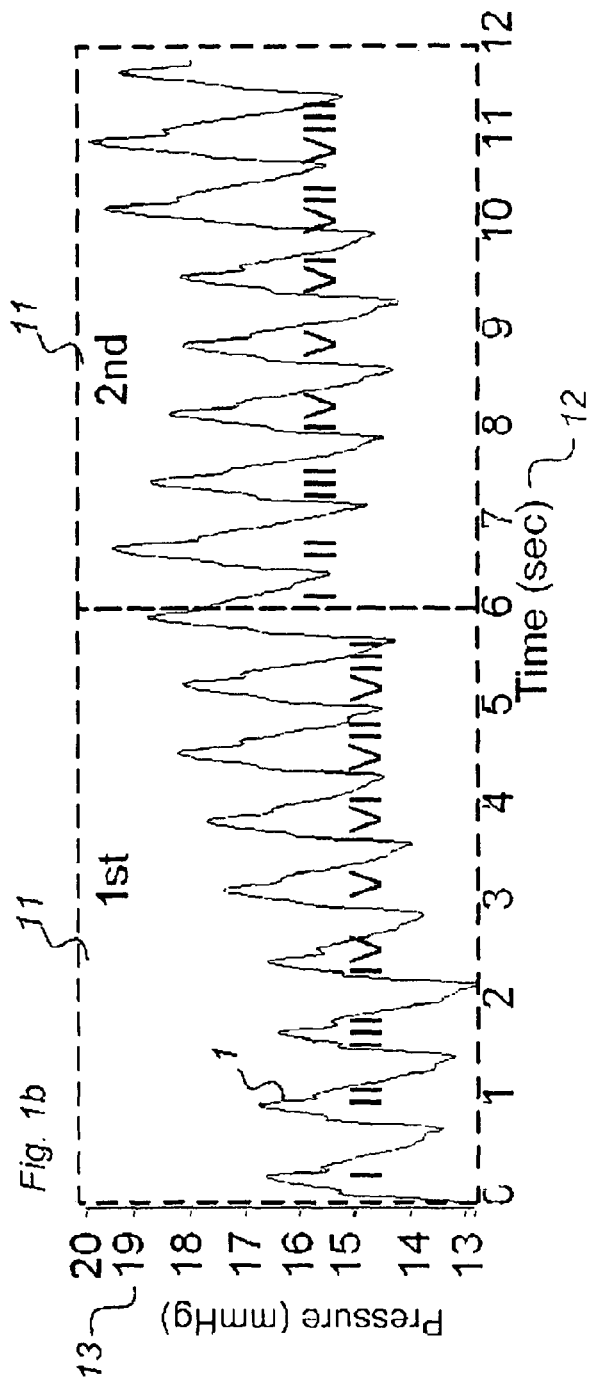

Fig. 2a
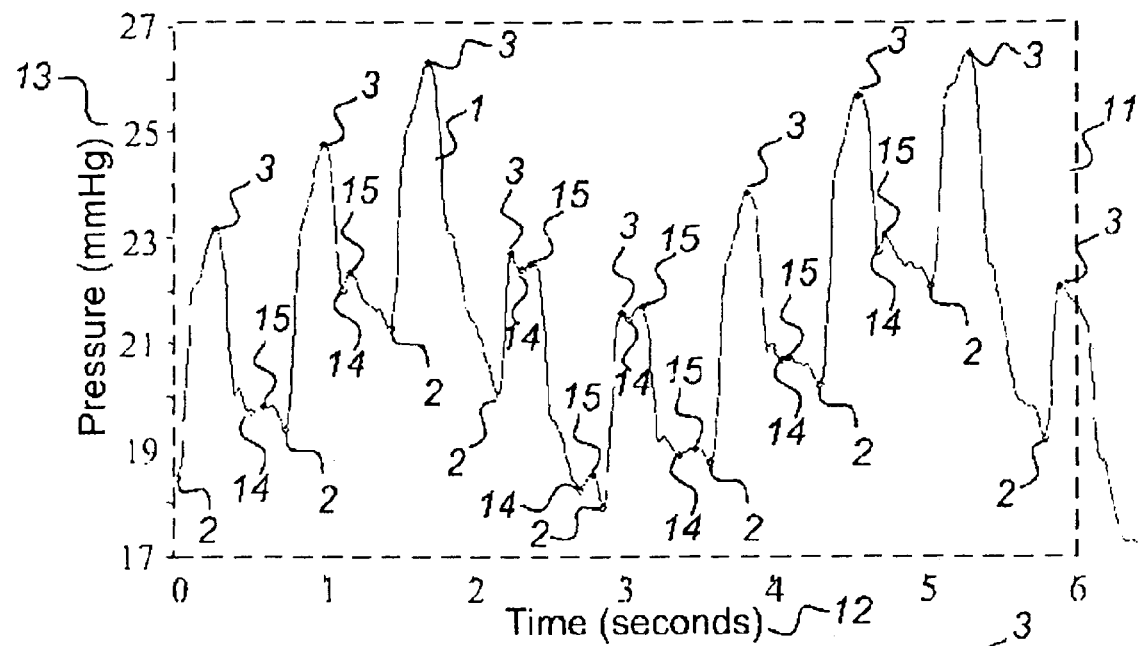
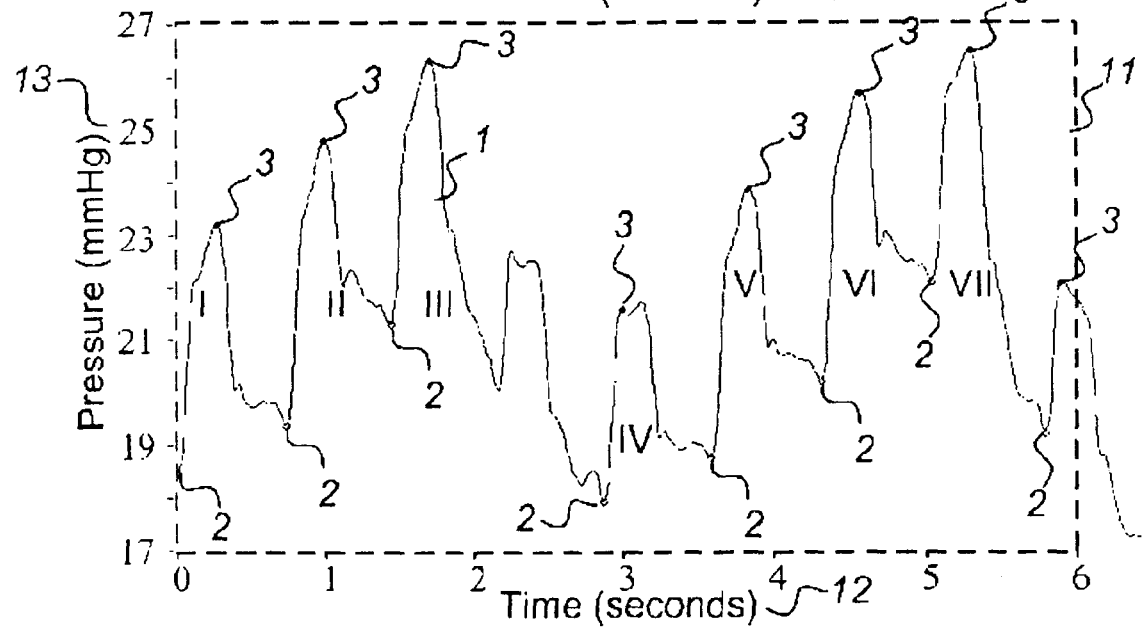
Fig. 2b

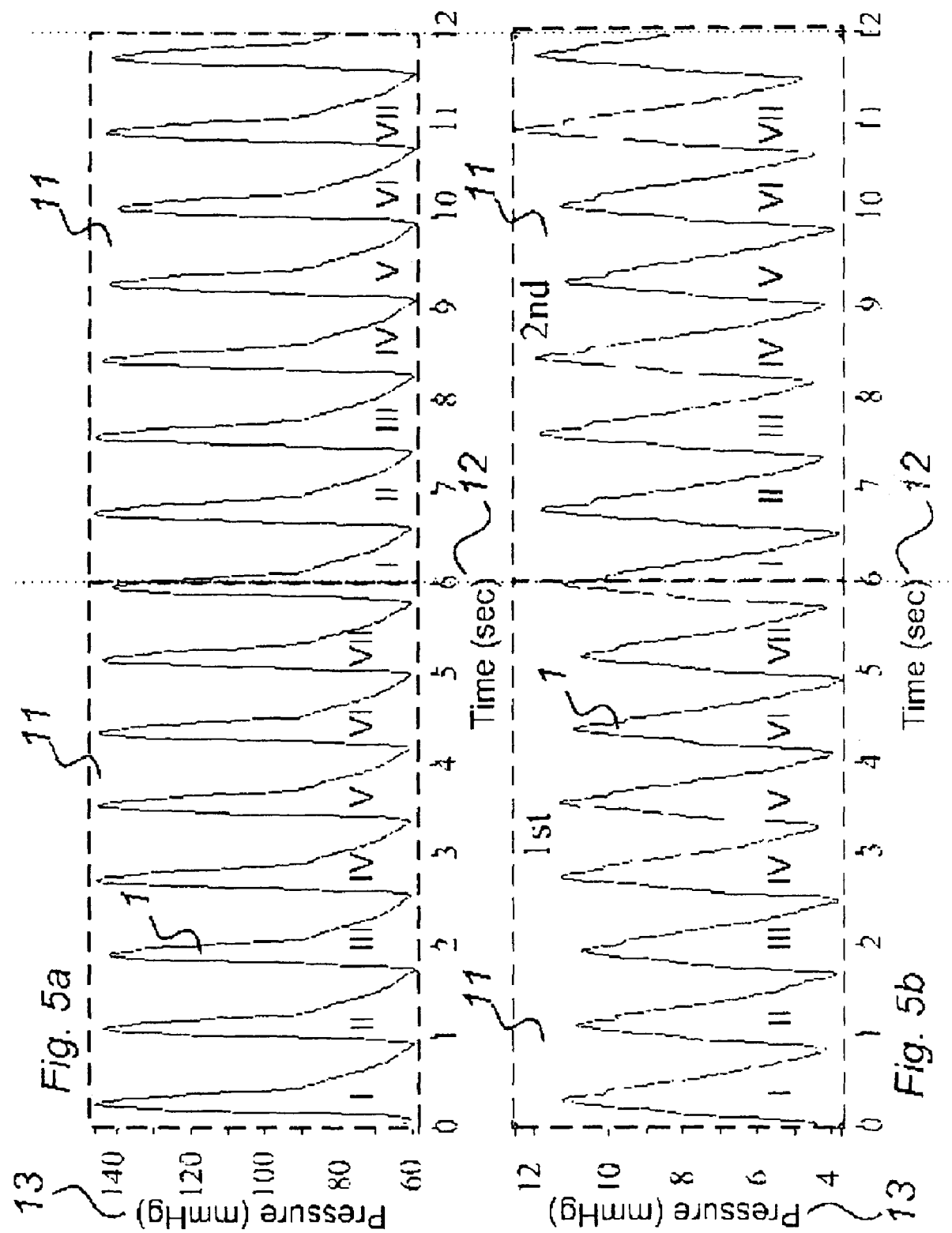

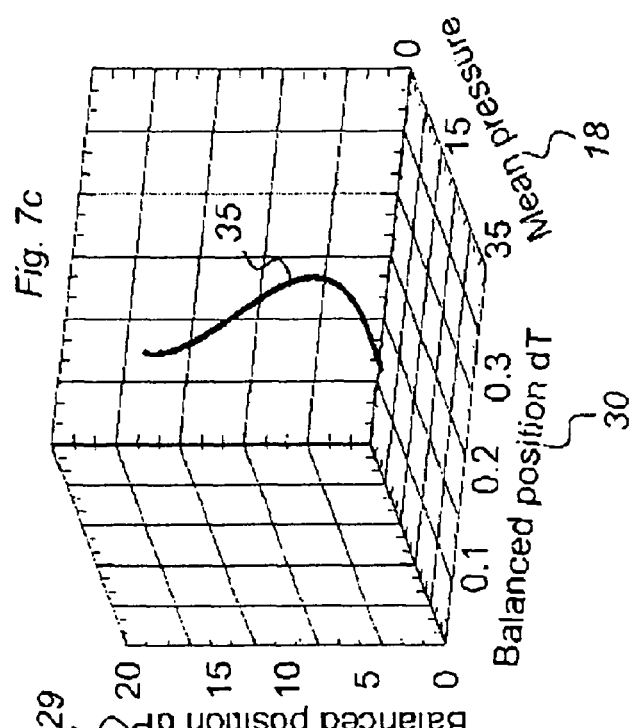
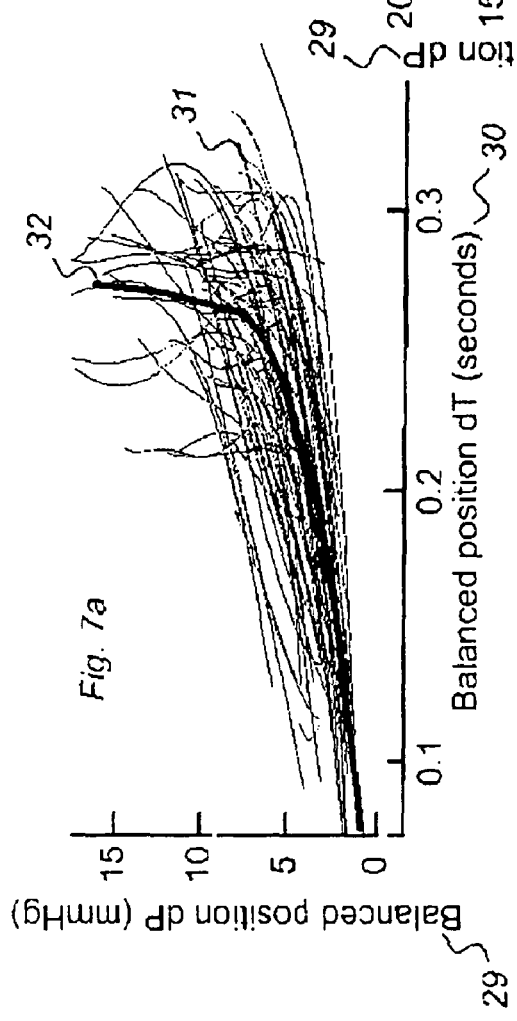
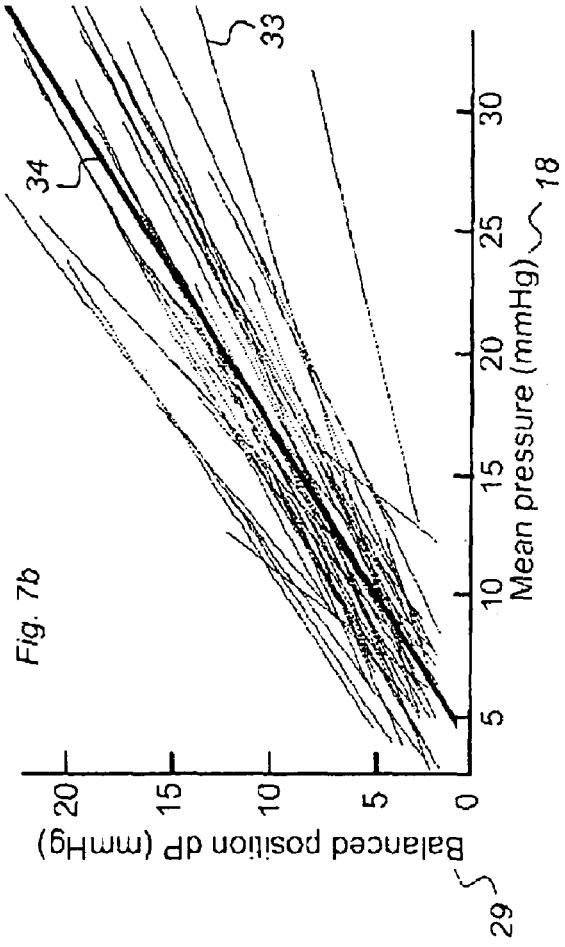

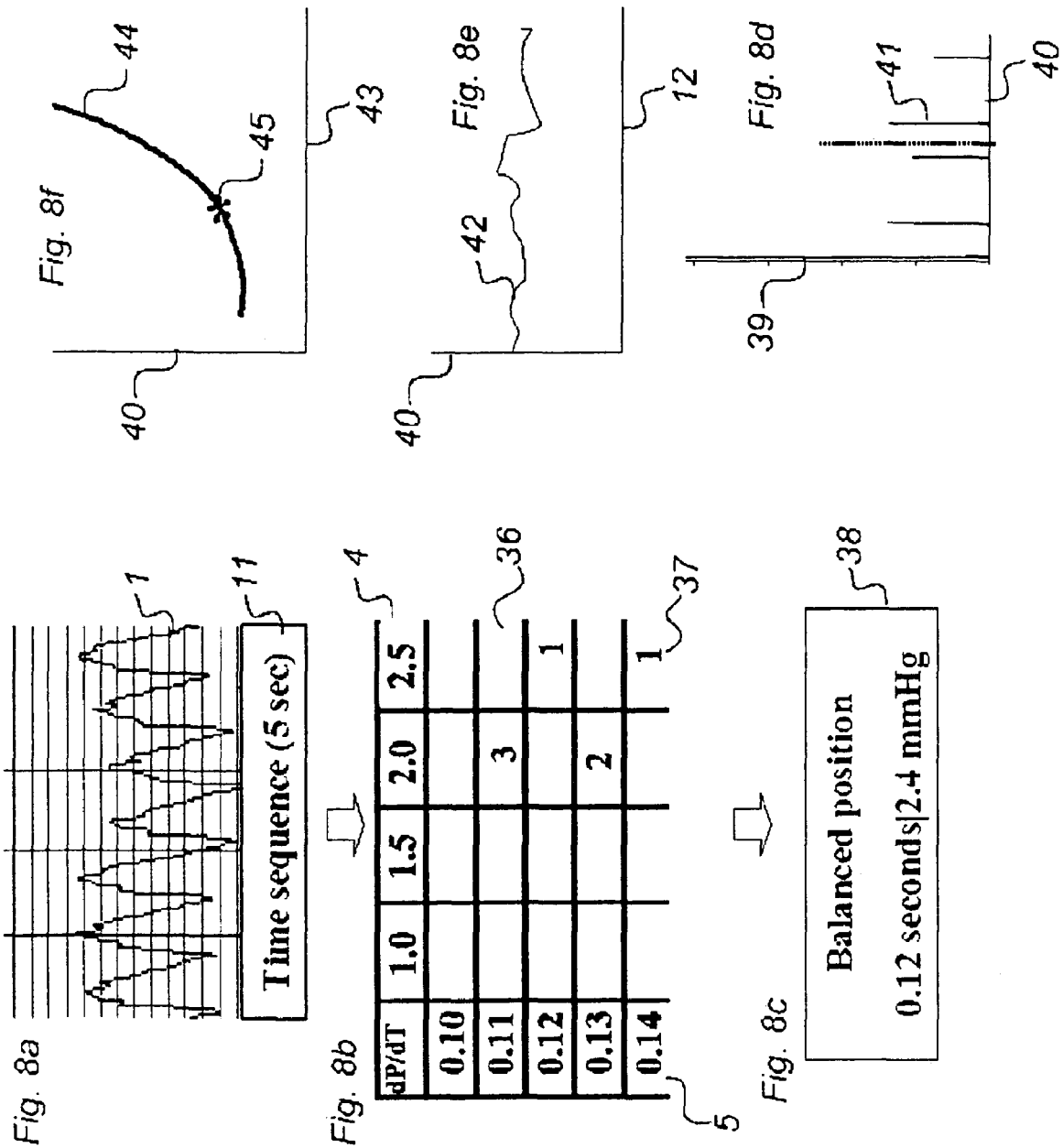

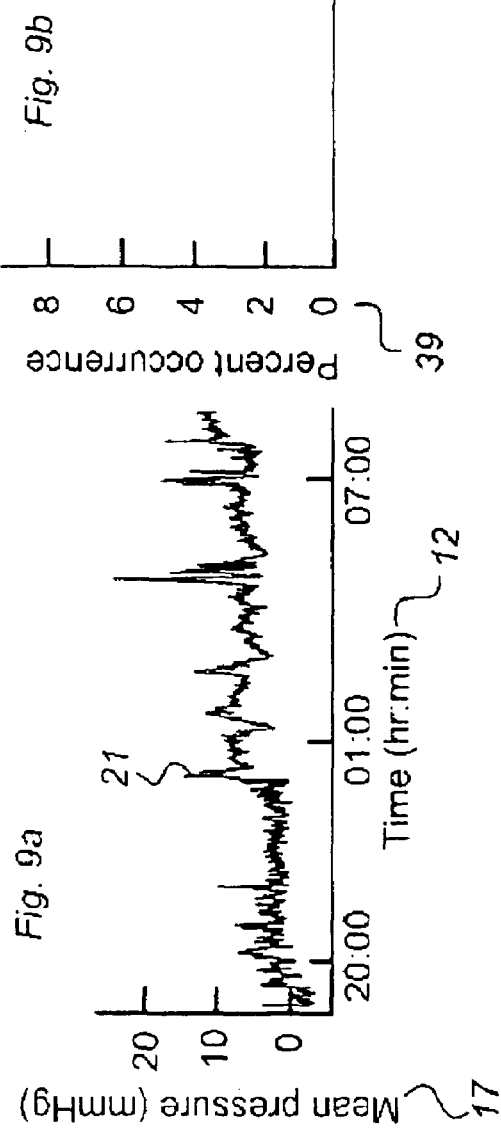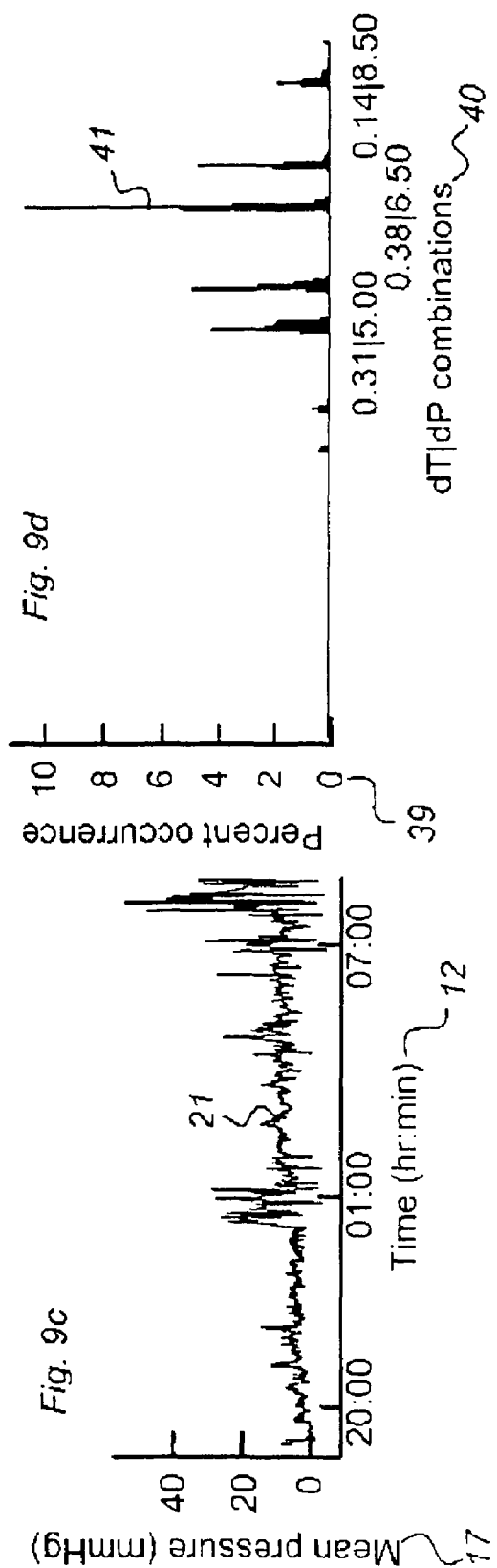

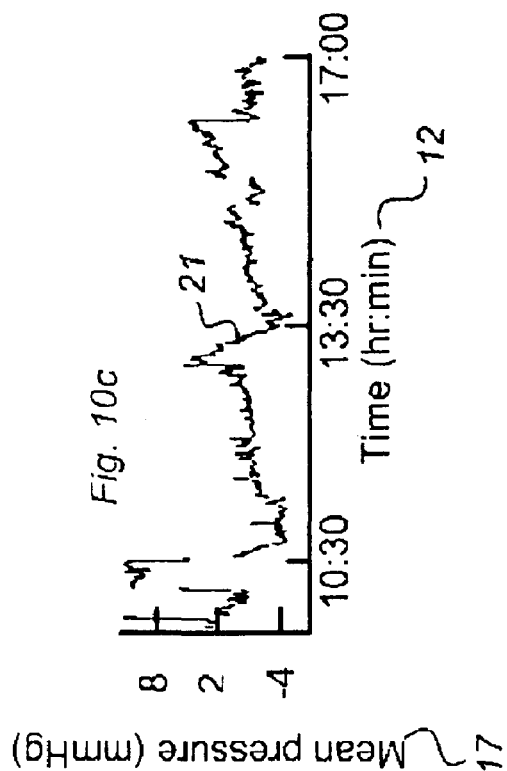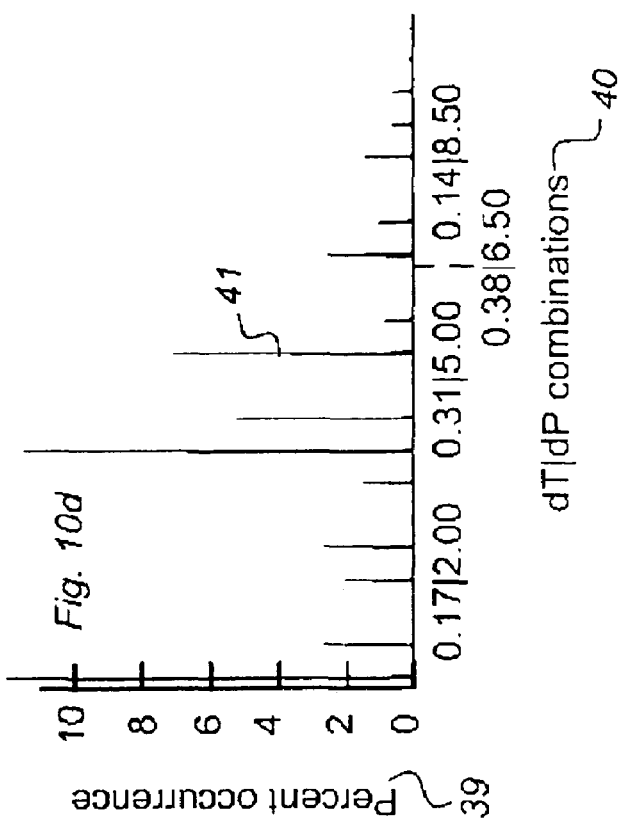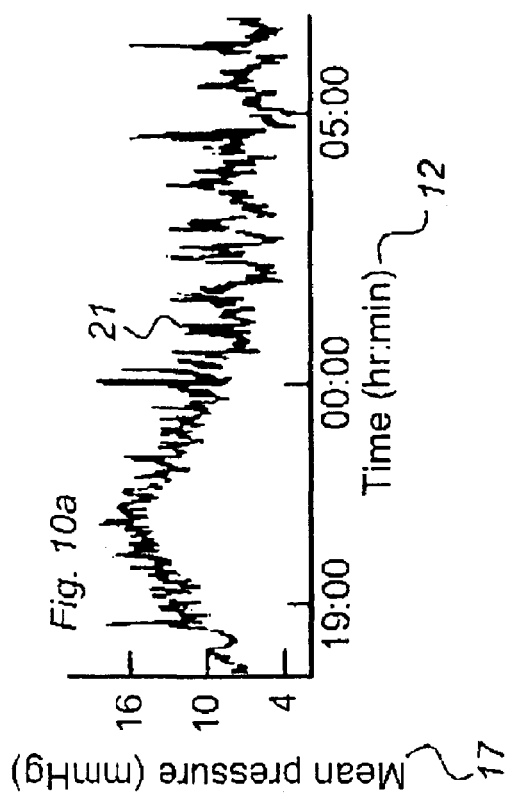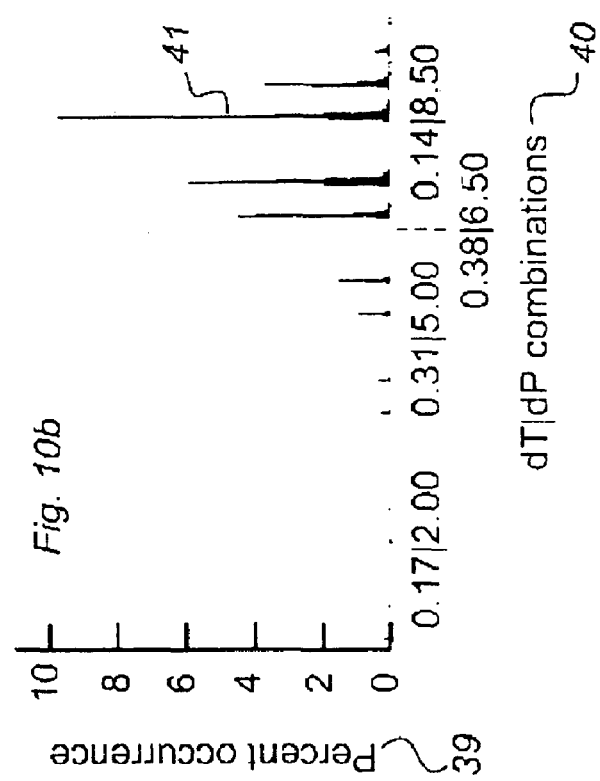

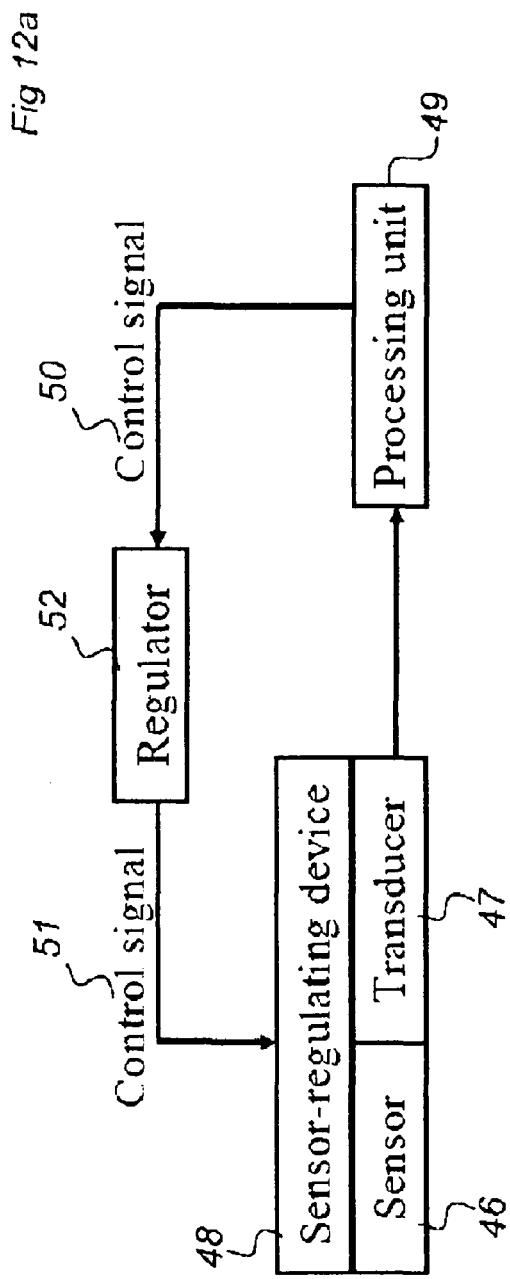
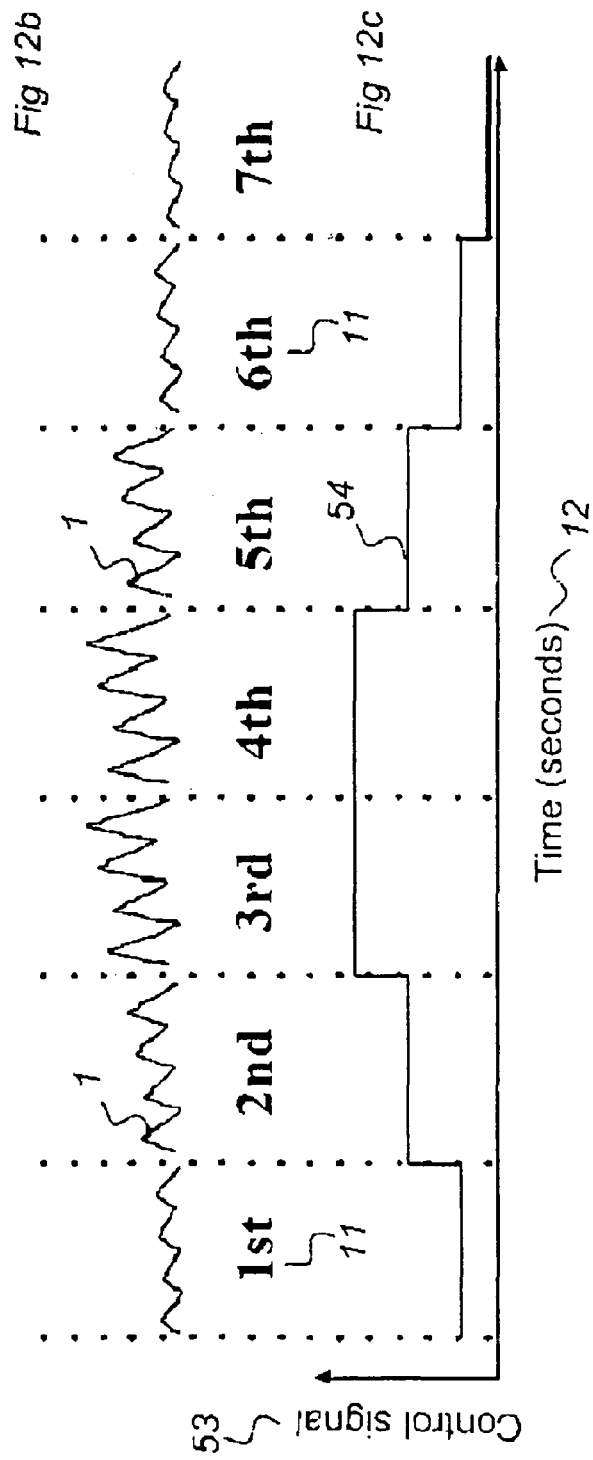
Fig 12a
Fig 12b
Fig 12c

METHOD FOR ANALYSIS OF SINGLE PULSE PRESSURE WAVES

This application claims priority on provisional Application No. 60/422,111 filed on Oct. 30, 2002, the entire contents of which are hereby incorporated by reference.

BACKGROUND OF THE INVENTION

1. Field of the Invention

Monitoring of pressures within human body cavities has an important role in diagnosis and management of a large number of diseases and clinical conditions. The present invention relates to a method for analyzing pressure signals derivable from pressure measurements on or in a body of a human being or animal, comprising the steps of sampling said signals at specific intervals, and converting the pressure signals into pressure-related digital data with a time reference.

More specifically, the invention relates to methods as defined in the preamble of attached independent claims 1 and 94.

2. Related Art

Continuous monitoring of pressures in humans and animals has a widespread place. During continuous pressure monitoring, today's existing technology, not the inventive technology (hereafter referred to as conventional or current technology) calculates a mean or area under curve of several seconds of pressure recordings. For example, for a given time sequence of 6 seconds, mean pressure may be computed as the sum of all pressure sample levels divided by the numbers of samples. Most modern monitors update the calculated pressure value each 5-10 seconds. Thereby information within the single waves is lost. Whether or not the mean pressure corresponds to single pressure waves during said time sequence is not known. Therefore, absolute numbers of systolic, mean and diastolic pressures shown oil the scope of vital signs monitors do not reveal single wave distribution. The basis for this praxis is the assumption of a linear relationship between mean pressure and amplitude of the single waves.

There are several problems with the current strategies of assessing continuous pressure recordings. Current technology uses calibration of pressures against a zero pressure level, usually the atmospheric pressure. This situation raises various problems, such as drift of zero pressure level during a period of recording. Differences in absolute zero pressure levels may cause false or inaccurate differences in pressures between different pressure recordings, making it difficult to compare pressure curves. Other causes of erroneous continuous pressure recordings are sensor failure, misplacement of pressure sensor, low quality of sensor signals related to movement of patient, and low signal-noise ratio of other reasons. Whether the quality of pressure signals is good or bad may be difficult to decide according to Current strategies of assessing continuous pressure signals. The present invention aims at solving these problems, introducing a new strategy of analysis of pressure related digital data, including assessment of the single pressure waves.

A continuous pressure signal fluctuates over time related to the cardiac beats. In the human or animal body cavities, single pressure waves are built up from the waves created by each of the cardiac pulsation's. For example, the intracranial and arterial blood pressure waves are intimately related as the intracranial pressure waves arise from the contractions of the left cardiac ventricle. Each heart beat results in a pulse pressure wave, termed single pressure wave. Related to the cardiac beats, these waves have a diastolic minimum pressure and a subsequent systolic maximum pressure. When it has not previously been possible to take the knowledge of single wave parameters into daily clinical practice, this situation is related to the facts that heart rate is variable, single waves fluctuate a lot over time, and the inter-individual variation is large. So-called spectrum analysis or Fourier analysis assesses fluctuations in pressure, but not by analyzing the single pressure waves.

Non-invasive pressure monitoring is partially established for blood pressure and ocular pressure monitoring, though no methods or devices allows for continuous single wave monitoring with identification of single wave distribution. In particular, applanation tonometry is a non-invasive method for intraocular pressure measurement, blood pressure measurement, and measurements of intracranial pressure in infants.

SUMMARY OF THE INVENTION

There are a number of human or animal body cavities in which pressures may be recorded for diagnostic and therapeutic reasons. For example, pressures in a human or animal body cavity relate to arterial blood pressure, intracranial pressure, cerebrospinal fluid pressure, ocular pressure, urinary tract pressure, gastrointestinal tract pressure. The present invention primarily was designed for analysis of pressure signals derivable from monitoring of single waves in blood vessels, the intracranial compartment, the cerebrospinal fluid (CSF) system, the ocular bulb and the urinary tract and bladder. These cavities represent, however, no limitation in the context of the invention. Other cavities may be the esophageal tract, the anal canal, and others not specified. Thus, this invention is not limited to analysis of pressures from only some particular human or animal body cavities, as the invention relates to a generic method for analysis of pressure derivable signals.

This invention relates to analysis of continuous pressure related signals. Such pressure related data may be derived from a variety of pressure sensors and pressure transducers. Independent of the type of sensor, a continuous pressure signal is measured, providing the opportunity for sampling of single waves. Examples of such sensors are solid or fiber-optic mechanical sensors for invasive monitoring, and sensors for invasive monitoring of pressure within a fluid system such as arterial or venous blood vessels, cerebrospinal fluid, or urinary bladder/tract. There are various other types of sensors providing signals indicative of pressures. Examples are sensors for non-invasive measurement of blood pressure, using principles of Doppler technology, or measurement of oxygen saturation, and non-invasive measurements of intacranial pressure using Doppler technology or acoustic signals. The most well-known principle of non-invasive pressure monitoring uses the principles of applanation tonometry. For example, applanation tonometry is used for monitoring of fontanel pressure in infants, and ocular pressure and arterial blood pressure. The unique with the present invention is the opportunity for determining single wave distribution by more optimal detection of single pressure waves using the inventive method of analyzing single pressure waves.

More specifically and in a first aspect of the invention, the method for a selected time sequence comprises the further inventive steps of:

a) identifying from said digital data the single pressure waves in said pressure signals, b) computing absolute mean pressure for said single pressure waves, c) computing single pressure wave related parameters of said single pressure waves, d) identifying numbers of single pressure waves with pre-selected parameter values of such waves with respect to amplitude, latency and rise time coefficient, e) plotting the numbers of occurrences of single pressure waves with pre-selected values of amplitude and latency in a first matrix., f) plotting the numbers of occurrences of single pressure waves with pre-selected values of rise time coefficients in a second matrix, g) determining balanced position of amplitude and latency combinations in said first matrix h) determining balanced position of rise time coefficients in said second matrix, and i) presenting the balanced positions obtained in steps g) and/or h) as numerical values or as related to weighted values.

Further embodiments of this first aspect of the invention are defined in sub-claims 2-93.

In a second aspect of the invention, the method is applied for more optimum single pressure wave detection, wherein the method for analysis comprises the further steps of:

identifying said single pressure wave related parameters during short time sequences, e.g. 3 seconds of duration.

establishing an analysis output based on said determining steps for single pressure wave related parameters during said time sequence, establishing a deliverable first control signal related to said single pressure wave analysis output for each of said time sequences, wherein said first control signal is determined according to one or more selectable criteria for said analysis output, wherein the method comprises the further steps of:

modifying said deliverable first control signal into a regulator deliverable second control signal, said second control signal corresponding to said first deliverable control signal, delivering said second control signal to a sensor-regulating device, causing modifications of performance of said sensor-regulating device.

Thus, this invention is not limited to specific types of pressure signals, however, the signal has to be continuous for a given time sequence. During continuous pressure monitoring, single pressure waves are sampled along with a time reference. Analog pressure signals are converted into digital pressure-related data. Since each wave represents a heart beat, the heart rate is known when the sampling rate is known. Determination of single wave distribution may be used in the real-time and online monitoring of pressures. Processing of single waves may be performed after sampling of pressure signals. Though data processing is performed with some delay, monitoring is real-time since the delay has no significance for the observed phenomenon. During identification of the single pressure waves, the continuous pressure signals undergo filtering and concatenation procedures wherein noise signals are removed. Each single pressure wave is identified according to the diastolic minimum ($P_{min}$) and systolic maximum ($P_{max}$) values. False $P_{min}$ and $P_{max}$ values are removed. Identification of correct $P_{min}/P_{max}$ values are made by means of pre-determined thresholds for the single wave amplitude ($\Delta P$), latency ($\Delta T$) and rise time coefficient ($\Delta P/\Delta T$) values. For the correctly identified single pressure waves, the single wave parameters [amplitude ($\Delta P$), latency ($\Delta P$), and rise time coefficient ($\Delta P/\Delta T$)] are determined for short time sequences (e.g. each 5 seconds). Such short time sequences with identified single pressure waves are accepted or rejected according to selected criteria. The latencies represent the time sequence when pressures increases from diastolic minimum to systolic maximum, and the pressure change occurring during this time sequence is the amplitude. The maximum ($P_{max}$) and minimum ($P_{min}$) values for the single waves are identified, and the matrix computed containing the amplitudes ($\Delta P$) on the vertical column and latencies ($\Delta T$) on the horizontal row. Accordingly, the amplitudes are related to the naming of the columns and the latencies to the naming of the rows. The number or percentages of the single waves with the various combinations of amplitude and latency are computed within a first matrix. The balanced position of occurrences of amplitude ($\Delta P$) and latency ($\Delta T$) are determined. In a one-dimensional second matrix is plotted the number of occurrences of single pressure waves with a given rise time coefficient ($\Delta P/\Delta T$) plotted, and the balanced position determined. Furthermore, the absolute pressure values during said time sequence is determined, either as mean pressure for the whole time sequence or as mean pressure for the single pressure waves solely during said time sequence. All of these single pressure wave parameters related to a recording sequence may be stored in a database.

Single waves are recorded repeatedly during a fixed time sequence (e.g. each 5 seconds). Such selected time sequences may have various durations, preferentially between 5 to 15 seconds. The actual heart rate should not influence the results in this particular situation). Various types of on-line presentation are possible. When balanced position of amplitude ($\Delta P$) and latency ($\Delta T$) are plotted in a two-dimensional weighted matrix, the balanced position may be represented as one weighted value, e.g. in a trend plot (weighted value on the Y axis and time on the X axis), or in a histogram (weighted value on the X axis and proportion or absolute number of occurrences on the Y axis). For the given time sequence, the numbers or percentages of single wave combinations are presented within the histogram. On the Y-axis is indicated percentage occurrence of the various single wave combinations of latency and amplitude, and the various latency/amplitude combinations are indicated on the X-axis. For example, the bar within the histogram with label on the X-axis of 0.2|3.5 indicates the percentage occurrence of the single wave with a latency of 0.2 seconds and amplitude of 3.5 mmHg in percentage of the total numbers of single waves during the actual recording time of 5 seconds. The matrix and/or histogram may be subject to a number of statistical analyses. In one embodiment it is useful to determine the balanced position within the histogram or matrix. This balanced position may be termed the centroid or the centre of distribution, though these terms represent no limitation of the scope of the invention. In this invention the term balanced position is preferred. Balanced position may refer to the balanced position of occurrences of amplitude ($\Delta P$) and latency ($\Delta T$) combinations in the first matrix (see Table I), or to balanced position of rise-time coefficients ($\Delta P/\Delta T$) in the second matrix. In this situation, balanced position is the mean frequency distribution of the single pressure wave parameter combinations.

According to the invention the matrixes and histograms of single wave distribution may be computed repeatedly online including alarm functions for the single wave distributions that may be considered as abnormal. Thereby, continuous update of single waves is an alternative way of presenting pressures. In such an implementation single wave distribution may be updated each 5 or 10 seconds.

According to the invention, a method is described for more optimum analysis of pressure signals from detection of single pressure waves by means of non-invasive pressure sensors. During short time sequences of pressure recordings (e.g. each 3 seconds) the single pressure wave parameters are computed. Between each of said time sequences a sensor-regulating device is modified by a regulator providing a control signal to the sensor-regulating device. Results of said analysis within the processing unit provide a control signal to the regulator that in turn provide another control signal to the sensor-regulating device. Thereby, the inventive method of single wave analysis may modify the function of the sensor device to give the most optimal single pressure wave detection. An example is described with regard to applanation tonomtery, though this represents no limitation of the scope of the invention. A pneumatic pump and bellow press the transducer array against the skin and tissue above the cavity wherein pressure is measured (e.g. artery), usually referred to as the hold down pressure. In some devices the monitor searches through a range of pressure values until it measures an optimal signal in order to determine optimal hold-down pressure. Determining single wave distribution is however not possible by these methods. The present invention enables optimum single pressure wave detection. Furthermore, according to the present invention, there is no need for calibration by an independent technique. With regard to monitoring of fontanel pressure in infants basically the same principles are used. In these cases, tonometry enables pressures to be measured non-invasively on neonates. None of the techniques of tonometry provides the opportunity for sampling of single pressure waves.

The particular features of the invention are described in the attached independent method claims, whereas the related dependent claims describe advantageous, exemplifying embodiments and alternatives thereof, respectively.

BRIEF DESCRIPTION OF THE DRAWINGS

FIG. 1 shows (a) parameters of a single pulse pressure wave, and (b) two time sequences wherein single pressure waves are identified.

FIG. 2 shows (a) one time sequence wherein all maximum and minimum values in the continuous pressure signal are detected, and (b) the identical time sequence wherein only the accepted minimum/maximum ($P_{min}/P_{max}$) pairs are shown.

FIG. 5 shows two identical time sequences with identical time reference for continuous (a) arterial blood pressure and (b) intracranial pressure measurements.

FIG. 7 shows the scatter plots for determining the best fitted curves for the relationships between (a) balanced positions of amplitude and latency, (b) mean pressure and balanced position of latency, and between (c) mean pressure, balanced position of amplitude and balanced position of latency.

FIG. 8 shows a sequence of events during real time monitoring of single wave distribution, including (a) determination of single pressure waves within time sequences, (b) plotting combinations of single pressure wave amplitudes and latencies during said time sequence within a matrix, and (c) determining numerical value of balanced position of amplitude and latency within matrix. The figure as well shows presentations of weighted values of balanced position of amplitude and latency within time sequences within (d) histogram, (e) trend plot, and (f) pressure-volume curve.

FIG. 9 shows the pressure curves and histogram presentations of single wave distribution for intracranial pressure measurements within (a-b) the brain parenchyma and (c-d) the epidural space.

FIG. 10 shows two repeated pressure curves (a) before and (c) after pressure reduction, including accompanying histograms of single wave distribution (b) before and (d) after pressure reduction.

FIG. 12 shows (a) an overview of a system for interaction between a processing unit, a regulator and a sensor-regulating device, for more optimum (b) single pressure wave detection during said time sequences, also indicating (c) modifications in control signal level applied to a sensor regulating device.

DETAILED DESCRIPTION OF PREFERRED EMBODIMENTS

Figure 3A:
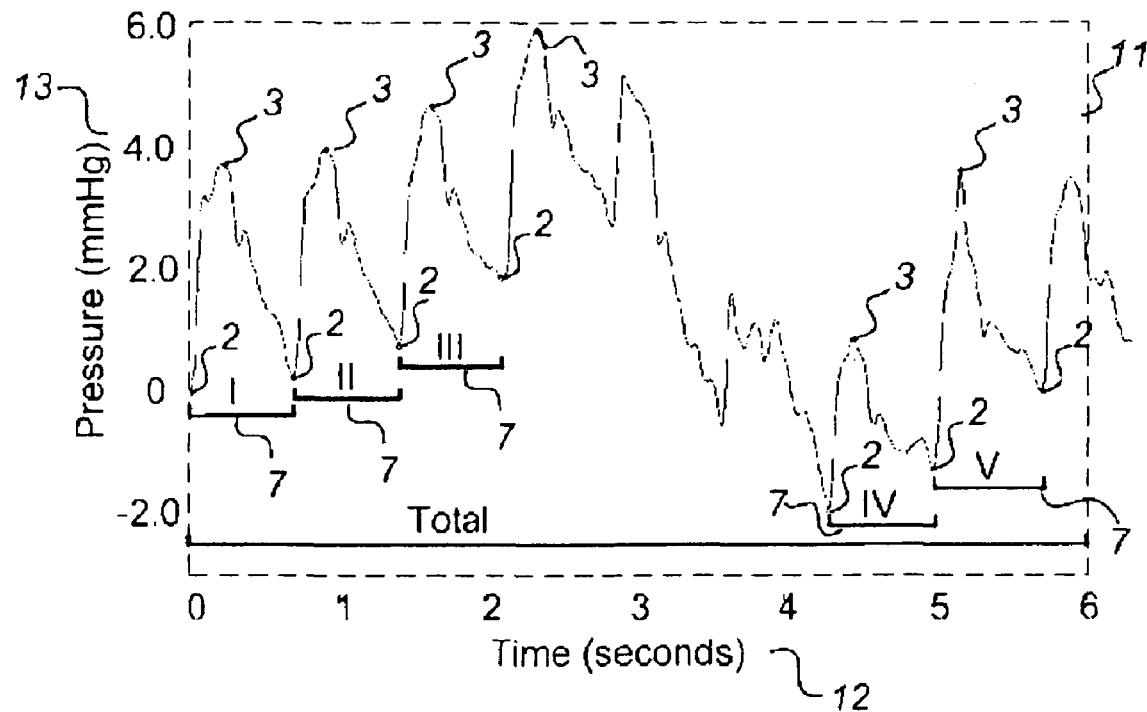
FIG. 3 shows (a) one time sequence illustrating computation of absolute mean pressure for said time sequence according to two methods, and (b) relationships between absolute mean pressures computed according to the two methods for a large group of time sequences.

With regard to sampling, analysis and presentation of single pulse pressure waves 1, relative differences in pressures are computed, not related to a zero pressure level such as the atmospheric pressure. The invention provides measurement and analysis of the following parameters included in the time sequences (FIG. 1):

a) Minimum ($P_{min}$) 2 is defined as the diastolic minimum pressure of the single wave, or as the valley of the wave. An individual single pressure wave starts and ends with a diastolic minimum ($P_{min}$) value.

b) Maximum ($P_{max}$) 3 is defined as the systolic maximum pressure of the single wave, or defined as the peak of the wave.

c) Amplitude ($\Delta P$) 4 is defined as the pressure difference when pressures increase from diastolic minimum pressure ($P_{min}$) to systolic maximum pressure ($P_{max}$).

d) Latency ($\Delta T$) 5 is defined as the time interval of the single wave when the pressures change from diastolic minimum pressure ($P_{min}$) to systolic maximum pressure ($P_{max}$).

e) Rise time coefficient ($\Delta P/\Delta T$) 6 is defined as the relationship between amplitude divided by latency.

f) Wavelength 7 is defined as the duration of the single pulse pressure wave between the diastolic minimum pressure ($P_{min}$) 2 representing the start of the wave and the diastolic minimum pressure ($P_{min}$) 2 representing the end of the wave. Wavelength is referred to as $P_{min}$-$P_{min}$ duration wherein first $P_{min}$ is inclusive and ending $P_{min}$ is not inclusive.

Whether the waveform is reproduced properly or not depends as well on a sufficient resolution order and a sufficient sampling rate. In FIG. 1a is shown a standardized single pulse pressure wave 1, indicating the various parameters of a single wave that may be analyzed quantitatively. A single intracranial pressure wave may contain three peaks, the first (P1) 8, second (P2) 9 and third (P3) 10 peaks. The maximum peak is termed the first peak (P1) 8 or top of the percussion wave. During the declining phase of the wave, there are two peaks namely the second peak (P2) 9, often termed the tidal wave, and the third peak (P3) 10, often termed the dicrotic wave. It is well known from the prior art that the absolute pressure value may determine whether the various peaks are present or not. The maximum value ($P_{max}$) 3 usually is related to the first peak (P1) 8, but as pressure increases also the second peak (P2) 9 may become the maximum value ($P_{max}$) 3. In this latter situation the systolic maximum ($P_{max}$) 3 is represented by the second peak (P2) 9. It should be noted that the algorithm of defining single waves 1 according to the maximum ($P_{max}$) 3 and minimum ($P_{min}$) 2 values, it is not always possible to determine whether the maximum ($P_{max}$) 3 value represents the first (P1) or second (P2) peak. Not to introduce misunderstandings, the present invention relates to identification of single pressure waves 1 according to the systolic maximum ($P_{max}$) 3 and the diastolic minimum ($P_{min}$) 2 pressure values. Thus, in the present application, the amplitude ($\Delta P$) 4 of the first peak is defined as the pressure difference between the diastolic minimum pressure ($P_{min}$) 2 and the systolic maximum pressure ($P_{max}$) 3, the latency of the first peak ($\Delta T$) 5 is defined as the time interval when pressures increases from diastolic minimum 2 to systolic maximum 3 pressures. It should be noted, however, that it is not always possible to exactly identify whether the top of the wave corresponds to the first peak or not. Whether or not the various peaks are identified depends on sampling rate and/or resolution. Therefore, the method described here does not require that the different peaks (P1-3) are identified, in other words the inventive method is not limited to the identification of the specific peaks P1-P3. Thus, single waves 1 are identified according to diastolic minimum ($P_{min}$) 2 and systolic maximum ($P_{max}$) 3 values, independent whether systolic maximum ($P_{max}$) 3 is related to the first (P1) 8 or second (P2) 9 peaks. In practice it may be nearly impossible to differentiate the first and second peaks.

In another embodiment reference may be to the second (P2) 9 and third (P3) 10 peaks. The maximum and minimum values may be specified for the different peaks (P1-P3), wherein also the single pressure wave parameters amplitude 4, latency 5, and rise time 6 coefficients are with reference to each of the specific pressure peaks (P1-P3), 8-10. In this situation, the identification of the first peak (P1) 8 is relative to maximum 3 and minimum 2. The identification of the second peak (P2) 9 also is relative to the first peak (P1) 8, and the third peak (P3) 10 is relative to the second peak (P2) 9. This embodiment requires that each peak (P1-P3) is determined within the single pressure wave 1. Thereby, latency 4, amplitude 5, and rise time coefficient 6 may be with reference to each of said single pressure waves.

An important inventive step is the identification of single pressure wave parameters within given time sequences 11. A time sequence 11 refers to a specified time period of pressure recording during a continuous pressure monitoring. With reference to current technology absolute mean pressure of continuous pressure signals usually is computed within short time sequences 11 of 5-10 seconds. This is done because it is useful to update regularly the pressure values during a time of continuous pressure recording. In order to be comparable against current technology, the inventor select time sequences of between 5 and 15 seconds duration. Thus, it is suggested that the lengths of the time sequences should be in the range of 5-15 seconds. The inventor found it useful to use time sequences of 5 or 6 seconds. In the latter situation, a continuous recording period is considered as built tip of a series of numerous continuous short time sequences of 6 seconds. The number of 6 seconds time sequences 11 are 10 during one minute, 300 during 30 minutes, 600 during 1 hours, 6000 during 10 hours and 12000 during 20 hours of continuous pressure recording. The inventor considered these 6 second time sequences 11 as the building blocks of the recording period. However, these suggestions of durations (e.g. 5 or 6 or 8 second durations) of time sequences 11 (or building blocks) should not be regarded as a limitation of the scope of the invention, as the time sequences might be of any duration selected by the user.

With reference to FIG. 1b, on the x axis is indicated the time of pressure recording 12, and on the y axis is indicated the pressure levels 13. Along the time scale 12 two time sequences 11 each of 6 seconds duration are indicated. The first time sequence 11 (named $1^{st}$) lasts from seconds 1-6 on the time scale 12, and includes eight single pressure waves 1 (numbered I-VIII). The second time sequence 11 (named $2^{nd}$) lasts from seconds 6-12 on the time scale 12, and also includes eight waves 1 (numbered I-VIII). On the pressure scale 13 is indicated the absolute pressure levels, as well as giving an indication of the values of the single wave amplitudes 4. As indicated in FIG. 1b, the first single pressure wave 1 in the second time sequence 11 (named $2^{nd}$) is wave named 1. This single wave 1 has its final minimum ($P_{min}$) 2 within the $2^{nd}$ time sequence. The inventor applied the criterion that a time sequence 11 always starts with a single pressure wave 1 with complete wavelength 7 ($P_{min}$-$P_{min}$), wherein the final $P_{min}$ is within said time sequence. When considering the $1^{st}$ time sequence (named $1^{st}$), the final wave does not terminate within the $1^{st}$ time sequence but terminates within the $2^{nd}$ time sequence. Therefore, this wave is included in the $2^{nd}$ time sequence. In order not to exclude single waves from the analysis, criteria must be included for determining whether a single pressure wave 1 located between two time sequences 11 should be located within the preceding or subsequent time sequence. The strategy relies on selected criteria. This strategy represents no limitation concerning the concept of time sequences.

The method of analysis of continuous pressure signals described in this invention is applied to continuous pressure signals during such selected time sequences. The method is applied to all continuous pressure signals for each of said time sequences in a continuous series of said time sequences during a continuous measurement period. Accordingly, a continuous pressure recording period is considered as built up of a continuous series of said time sequences wherein said time sequences are accepted or rejected for further analysis according to selected criteria.

Based on measurement of a continuous pressure signal, various strategies may be used to identify the single waves. Each pressure signal may be identified on the time scale 12 because pressures are recorded along with a time reference. In one implementation, single waves are identified according to the maximum ($P_{max}$) 3 and minimum ($P_{min}$) 2 values. The following is an example of the procedure of identifying maximum ($P_{max}$) 3 and minimum ($P_{min}$) 2 values, though the example is not intended to limit the scope of the invention.

The procedure of sampling signals indicative of pressure and converting said signals into digital data are described. The specific steps described here represent no limitation as several strategies may be used. The first part of the signal conditioning is the software filter. This filter removes a great deal of the high frequency noise. The source of the high frequency noise is not always possible to point out, but it will always be present in many different shapes and magnitudes. Various filters may be used. The inventor found it useful to apply a $25^{th}$ order Bessel low pass filter, with a 25 Hz cut-off frequency. Other filters are available. The filter is programmed in a manner that removes both the transient part and phase lag. This is done by taking a copy of the first 100 samples in the signal, and then reversing the order. Then the copy of the first 100 samples is concatenated to the original signal. This process is also repeated for the 100 last samples in the signal. Then this signal is processed in the digital filter, the transient part will appear in the "new concatenated" part in the signal. It will not destroy the original signal. In order to remove phase lag, the filtered signal is restored by taking a subset of data from the signal processed by the filter algorithm. The subset is taken from sample index 109, with a length equal to the original signal. The specific values referred to in this paragraph depend on sampling frequency and other variables, and should not be regarded as limitations of the scope of the invention.

Reference is now given to FIG. 2. Most of the pressure signals in the human body are very dynamic signals, which contain a lot of peaks and valleys, not related to diastolic minimum and systolic maximum pressures. This paragraph describes the procedure of defining peaks related to systolic maximum pressure ($P_{max}$) 3 and valleys related to diastolic minimum pressure ($P_{min}$) 2. It should be noted that determination of peaks ($P_{max}$) and valleys ($P_{min}$) may as well be related to the specific peaks (P1-P3) within said single pressure waves 1. The signals are also sometimes garbled with artificial signals. In this context peaks refer to maximum values and valleys to minimum values. The result may be a lot of unwanted maximum ($P_{max}$) 15 and minimum ($P_{min}$) 14 detections. An unwanted or artificial minimum ($P_{min}$) 14 value is a minimum value that does not represent the diastolic minimum of said single pressure wave, and an unwanted or artificial maximum ($P_{max}$) 15 value does not represent the systolic maximum value of said wave. The peaks or valleys that are considered as unwanted or artificial depend on the criteria used during the identification procedure. As indicated in FIG. 2a, the procedure of identifying maximum ($P_{max}$) 3 and minimum ($P_{min}$) 2 values always results in a lot artificial maximum ($P_{max}$) 15 and minimum ($P_{min}$) 14 detection values. In FIG. 2a all the detected minimum and maximum values are shown. In other words the peak and valley detections have to be refined according to selected criteria. Therefore, wrong maximum 15 and minimum 14 values have to be removed. A total of eight wrong maximum 15 and eight wrong minimum 14 values are indicated in FIG. 2a. The acquired signal is first run through separate detection of minimum and maximum values. The maximum peak threshold value (or peak) is set to the lowest level in the signal, with duration longer than pre-defined values. A variety of pre-defined values may be chosen. The minimum threshold (or valley) is set to highest signal level, and the duration of the valley is a pre-defined value, as described above. Subsequent to this analysis, all maximum and minimum values are represented with an amplitude value and a location value or time stamp. This procedure will result in a lot artificial maximum ($P_{max}$) 15 and minimum ($P_{min}$) 14 detection values. Therefore the maximum and minimum detection has to be refined. After refinement, the result is a collection of approved maximum ($P_{max}$) 3 and minimum ($P_{min}$) 2 pairs (FIG. 2b) that may be presented to the function handling the dynamic parameter analysis. First, grouping of the maximum values and minimum values is performed. For every maximum the subsequent minimum is found. This couple makes a maximum-minimum ($P_{min}/P_{max}$) pair. The latter maximum-minimum pair is inspected for threshold level. The threshold value has to be larger than a given value. Subtracting the maximum amplitude and minimum amplitude performs this. The inventor found it useful to use the following criteria for intracranial pressure: Amplitude (ΔP) 4 must be between 1.0 and 35.0 mmHg, and latency (ΔT) 5 between 0.10 and 0.40 seconds. For arterial blood pressure, the thresholds were 30-120 mmHg for amplitude (ΔP) 4 and 0.10 to 0.40 seconds for latency (ΔT) 5. These thresholds represent, however, no limitation of the scope of the invention. Other thresholds may as well be used. The pre-defined values may depend on age, and other variables such as type of pressure, type of cavity wherein pressure is measured, as well as underlying diseases. If the amplitudes (ΔP) 4 and latencies (ΔT) 5 are different from the pre-selected values, the pair is discarded. All the dynamic values are calculated by using the approved minimum-maximum ($P_{min}/P_{max}$) pairs. Only approved $P_{min}/P_{max}$ pairs are entered into the time sequences for further analysis. Thus, an accepted $P_{min}/P_{max}$ pair refers to an accepted diastolic minimum ($P_{min}$) 2 value followed by a subsequent systolic maximum ($P_{max}$) 3 value, indicative of an accepted single pressure wave 1. Criteria are applied as well to which diastolic minimum ($P_{min}$) 2 value that is considered to terminate the single pressure wave. The values which are calculated are amplitude (ΔP) (delta intracranial pressure expressed in mmHg) 4, latency (ΔT) 5, rise time coefficients (ΔP/ΔT) 6, and heart rate 16. The latency (ΔT) 5 from minimum to maximum is the time where the pressure of the single wave increases from the diastolic minimum pressure ($P_{min}$) 2 to the systolic maximum pressure (wavelength $P_{min}$-$P_{min}$) 3. Afterwards the $P_{min}/P_{max}$ pair is inspected for the ΔP/ΔT 6 value. The ΔP/ΔT 6 value can be expressed as (peak amplitude-valley amplitude) divided by (peak location—valley location). This will further remove $P_{min}/P_{max}$ pairs caused by for example an artefact in the collected signal. All ΔP/ΔT values with a value equal or larger than a given value are discarded. Another criterion is related to the wavelength duration. Since the wavelength is a measure of the heart rate, the heart rate represents still another criterion. After applying the various criteria to single pressure wave detection, the collection of peaks and valleys now contains only approved $P_{min}/P_{max}$ pairs, corresponding to approved single pressure waves. With reference to FIG. 2b, a total of 8 accepted $P_{min}/P_{max}$ pairs are indicated. The individual single pressure waves 1 are indicated along with the time reference on the time scale 12, and the levels of the single wave amplitudes are indicated on the pressure scale 13. The duration of said time sequence is 6 seconds. It is indicated that each of these $P_{min}/P_{max}$ pairs (i.e. single pressure waves) have a diastolic minimum 2 value followed by a subsequent maximum 3 value. Furthermore, the relation of the single pressure waves 1 to the time sequence 11 is indicated. The first 7 accepted $P_{min}/P_{max}$ pairs correspond to the first seven single pressure waves (waves named I, II, III, IV, V, VI, VII). The final accepted $P_{min/Pmax}$ pair has no number since this wave is not included in this time sequence 11. The reason for this is that no accepted minimum 2 value was identified within the time sequence 11. Provided that such an accepted minimum 2 value is determined within the subsequent time sequence, this wave will become the first wave in the following time sequence (see FIG. 1b).

Thus, during a given recording period all single pulse pressure waves are identified. However, due to artifacts some waves are missed. The software allows the computation of numbers of artifacts and missed single waves, as well as relates this to total counts of single waves. Hence, the artifact ratio may be computed. Given that the numbers of artifacts are considered as too high a recording period may be omitted from analysis. Such artifacts relate to pressure recording sequences without accepted single pressure waves (i.e. accepted $P_{min}/P_{max}$ pairs). There are several reasons for not identifying single pressure waves: Failure of pressure sensor may cause erroneous pressure recordings. Noise in pressure signals is another reason. The identification of the correct single pressure waves provides the opportunity for only including those parts of the pressure recordings that include single pressure waves.

Measurement of single waves requires a continuous pressure signal, though the pressure signals may be sampled at a variable rate. The sampling frequency preferably should be above 10 Hz. The inventor initially found it sufficient to use a sampling rate of at least 100 Hz to identify maximum ($P_{max}$) 3 and minimum ($P_{min}$) 2 values. A higher sampling rate (at least 200 Hz) may be required to find the maximum $P_{max}$ 3 and minimum $P_{min}$ 2 values for the individual peaks (P1-P3) 8-10. When valleys ($P_{min}$) and peaks ($P_{max}$) are determined with reference to the specific peaks P1-3, said valleys and peaks are relative to maximum values ($P_{max}$) related to systolic maximum pressure and minimum values ($P_{min}$) related to diastolic minimum pressure for said single pressure waves.

The invention is not limited to a particular range of sampling frequencies. Rather the sampling rate should be sufficient to detect the various single pressure wave parameters (i.e. $P_{min}$, $P_{max}$, $\Delta P$, $\Delta T$, and $\Delta P/\Delta T$).

In summary, the procedure of identifying correct $P_{min}/P_{max}$ pairs includes different steps: (1) Filter and concatenation of digital pressure signals. (2) All minimum ($P_{min}$) and maximum ($P_{max}$) values are identified and represented with an amplitude value and a location value (or time stamp). (3) All $P_{min}/P_{max}$ pairs are identified, where the subsequent minimum ($P_{min}$) value is found for every maximum ($P_{max}$) value. (4) Only those $P_{min}/P_{max}$ pairs meeting certain pre-selected criteria concerning thresholds for $\Delta P$, $\Delta T$ and $\Delta P/\Delta T$ are accepted. (5) The single pressure wave parameters for given time sequences are determined. (6) The time sequences are subsequently accepted or rejected, according to criteria for the time sequences. With reference to the time sequences 11, a question is which single pressure waves that should be included. A time sequence may contain parts of single waves both in the first and final part of the time sequences. It is not useful to discard waves of this reason. During a continuous recording period, single pressure waves 1 occurring between two time sequences are included in the first or second time sequence according to selected criteria. The invention is not limited to which criteria that are used. The inventor used the following procedure: First, with regard to the final part of a time sequence 11, the inventor found it useful to include in the time sequence 11 the single wave 1 that is terminating within the time sequence 11, which is the single wave terminating with its last P1an, within said time sequence. Thus, the last single pressure wave 11 included within a time sequence 11 will have its whole wavelength ($P_{min}$-$P_{max}$-$P_{min}$) within that particular time sequence, including its last $P_{min}$. As indicated in FIG. 2b, the accepted $P_{min}/P_{max}$ pair subsequent to single wave no. VII is not included in the time sequence presented. If the last accepted $P_{min}/P_{max}$ pair has no $P_{min}$ the inventor found it useful to use this wave in the following time sequence, provided a following time sequence is measured. Thereby, the single pressure waves may be immediately analysed for said time sequence without waiting for the results of analysis of the next time sequence. Second, when considering the first part of a time sequence 11, the first single wave 1 will have its final $P_{min}$ within this time sequence. With reference to FIG. 1b, in the second time sequence (named $2^{nd}$) the first wave (named 1) is the single wave with its final $P_{min}$ within the second time sequence. The same aspect is indicated in FIGS. 5a and 5b.

In FIGS. 1b, 2a and 2b are indicated on the pressure scale 13 (y axis) the absolute pressure levels, which also give an indication of the values of amplitudes ($\Delta P$) 4 of the single pressure waves 1. The amplitude ($\Delta P$) 4 values are relative values, not related to a zero pressure level, since the amplitude ($\Delta P$) 4 levels represent the pressure difference between the systolic maximum ($P_{max}$) 3 and diastolic minimum ($P_{min}$) 2 pressure levels. This is an important aspect of the invention.

The absolute pressure levels of the single pressure waves 1 may as well be determined. The pressure scales 13 of FIGS. 1b, 2a and 2b refer to the absolute pressure levels that are relative to the atmospheric zero pressure level. The term absolute pressure refers to the situation when pressure is relative to the atmospheric zero pressure level. According to current technology, absolute pressures may be computed as mean or average of pressures during a time sequence of 5 seconds, and shown on the Y-axis. The X-axis shows the time of pressure recording. The fundamental difference between the curve according to the present invention and the conventional curve according to current technology relates to the strategy of processing pressure signals. According to current technology, pressures may be processed in sequences of 5 seconds, and the mean or area under curve for continuous pressure signals during the 5 seconds period is computed. By this conventional approach information about single waves are missed. The time period wherein mean pressure is computed may vary and depending on the monitor system. Furthermore, there is a wide range concerning pressure sampling frequency. Most monitors compute mean pressure in sequences of 5-8 seconds, though the term absolute mean pressure does not refer to a particular recording period.

This invention introduces a new inventive step concerning computation of absolute mean pressure, related to time sequence. This method is hereafter referred to as Method 2, as opposed to Method 1, representing conventional or current technology. The differences between conventional technology (Method 1) and the method according to this invention (Method 2) are illustrated in FIG. 3a. Given that absolute mean pressure is computed for a time sequence 11 of 6 seconds, current technology takes into account all recorded pressure signals during the time period, indicated by the line termed Total in FIG. 3a. Absolute mean pressure for said time sequence 11 is the sum of all sample values (pressure levels) divided by numbers of samples during said time sequence. In equation 1 is shown the procedure of computing mean pressure (x=pressure level for each sample, and n=numbers of samples in the sequence). According to Method 1, a absolute mean pressure of 1.85 mmHg was computed for the time sequence presented in FIG. 3a.

$$\text{Mean} = \frac{1}{n}\sum_{i=0}^{n-1} x_i \qquad (1)$$

The time sequence indicated in FIG. 3a shows five accepted single pressure waves 1 within said time sequence (named I, II, III, IV, and V). According to the criteria used, the pressure signals between single wave III and IV were not indicative of single pressure waves. The basic concept of this invention is that pressure values are only relevant when related to single pressure levels, since pressure signals not indicative of single pressure waves probably represent noise, not related to pressure per se. Mean pressures computed according to conventional technology does not take into account whether pressure signals are related to single pressure waves or not. This invention introduces a new inventive step, namely computing mean pressure for said time sequence 11 as the sum of mean pressure for all individual single pressure waves ($P_{min}$ to $P_{min}$) divided by the number of waves during said time sequence. Thereby, pressure samples not related to single pressure waves are not included in determining absolute mean pressure for the particular time sequence. For the time sequence presented in FIG. 3a the wavelength ($P_{min}$ to $P_{min}$) 7 for each individual single wave (I to V) is indicated. In this situation the Formula 1 is applied to each individual single wave, wherein each wave begins and ends with a diastolic minimum value, equal to the wavelength ($P_{min}$ to $P_{min}$) 7 of said single pressure wave 1. According to equation 1, for each individual single wave, the sum of all pressure samples (pressure levels) is divided by the numbers of samples. In this particular example, the sampling rate was 100 Hz. Absolute mean pressure was 2.5 mmHg for single pressure wave I, 2.27 mmHg for wave II, 2.96 mmHg for wave III, −0.45 mmHg for wave IV and 1.07 mmHg for wave V. Second, for the whole time sequence, the sum of mean pressure for each individual single pressure wave during said time sequence is divided by the number of single waves. Non-accepted single waves (or time sequences) are not included in the analysis. Mean pressure for the time sequence in FIG. 3a according to Method 2 was 1.67 mmHg [(2.5+2.27+2.96−0.45+1.07)/5]. Actually the difference was small concerning absolute mean pressure computed according to Method 1 (1.85 mmHg) and Method 2 (1.67 mmHg).

Figure 3B:
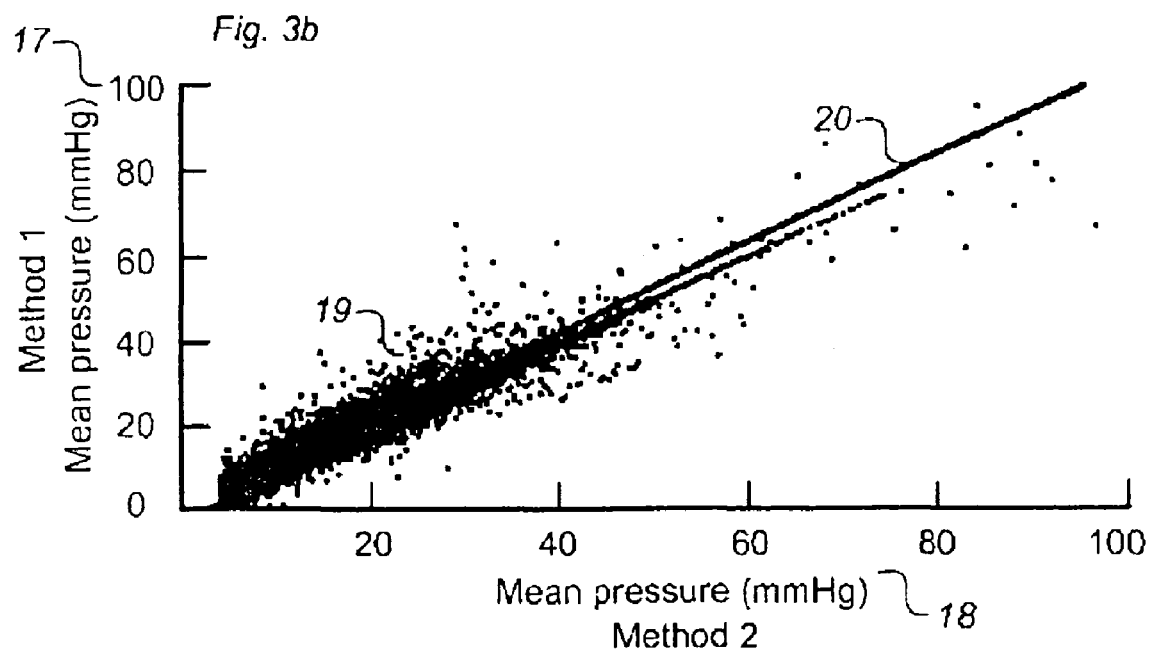

In FIG. 3b is shown the relationships between absolute mean pressure computed according to Method 1 or Method 2. On the y axis, the absolute mean pressure 18 refers to mean pressure computed according to Method 1, with reference to absolute mean pressure 18 computed according to Method 2 on the x axis. Each plot in the scatter 19 refers to absolute mean values computed by either of the methods. Both methods were applied to individual time sequences of 6 seconds during a series of continuous time sequences in a total of 75 continuous pressure recordings. These 75 continuous pressure recordings included a total of 873546 time sequences 11, each lasting 6 seconds. Of these time sequences, a total of 144835 time sequences were rejected according to selected criteria. No single pressure waves were found in 20862 time sequences. Thereby, the plot presented in FIG. 3b is based on a total of 707849 time sequences, each lasting 6 seconds. As indicated in FIG. 3b, at the group level a very high correlation exists between mean pressure computed according to Method 1 and Method 2, as indicated by the regression line 20.

Figure 4A:
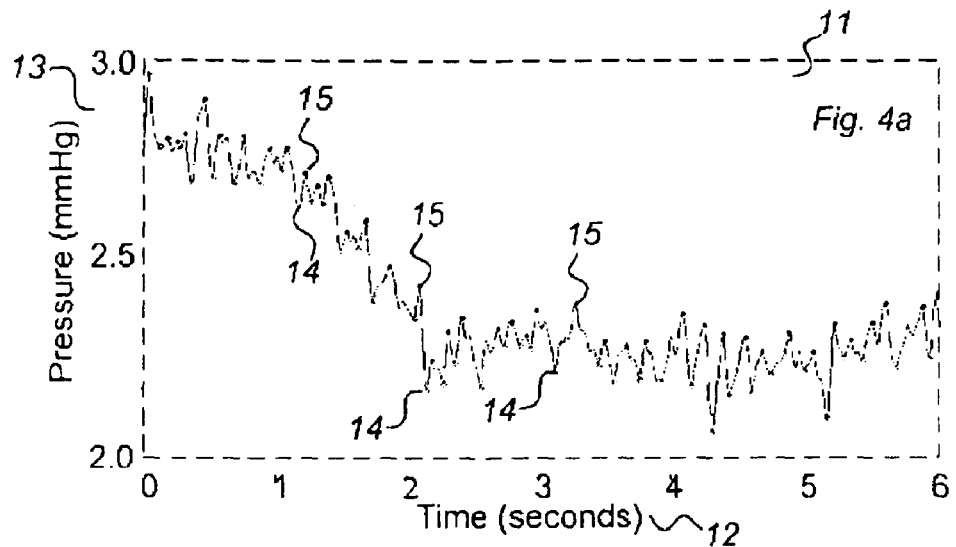
FIG. 4 shows (a) one time sequence wherein only false minimum/maximum ($P_{min}/P_{max}$) pairs are shown, and a trend plot of absolute mean pressure computed according to (b) the first or (c) the second method.
Figure 4B:
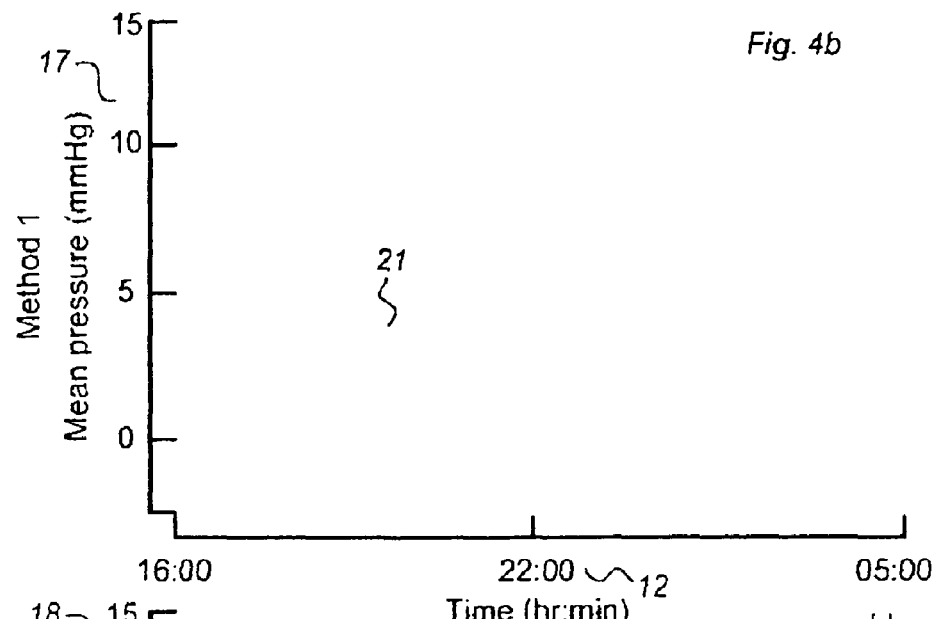
Figure 4C:
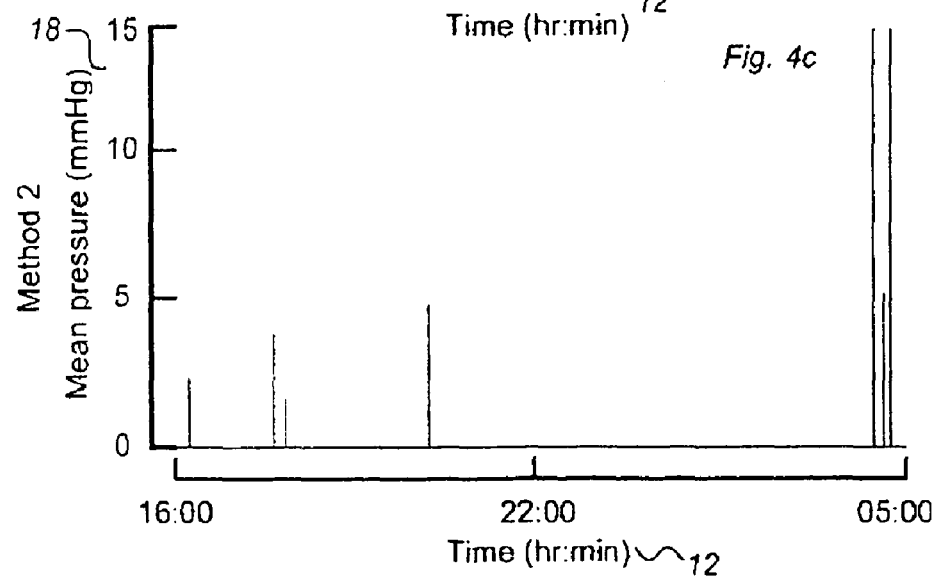

Despite a very high correlation between absolute mean pressures computed by either of the methods, a major advantage with the inventive method (Method 2) is that absolute mean pressure is computed only when single pressure waves are identified. If no single pressure waves are accepted or identified, no absolute mean pressure is computed. Method 1, on the other hand, computes mean pressure whether single pressure waves are present or not. Reference is now given to FIG. 4 that shows an intracranial pressure recording lasting about 11 hours and 54 minutes. This continuous recording period consisted of a continuous series of 7145 time sequences 11. Only a total of 7 time sequences 11 were accepted, whereas 7134 time sequences 11 contained no single pressure waves, and 4 time sequences 11 were rejected according to selected criteria. In FIG. 4a is provided an example of one of the time sequence 11 of 6 seconds that contained no single pressure waves. The absolute pressure levels were between 2 and 3 mmHg. As shown the pressure signal contained only unwanted or artificial minimum 14 and maximum 15 values, not related to single pressure waves 1. According to Method 1, mean pressure for each time sequence 11 is computed as the sum of all pressure sample levels divided by the number of pressure samples. In FIG. 4b, the mean pressure 17 according to Method 1 computed within each time sequence each 6 seconds is plotted repeatedly against time in the time scale 12. The mean pressure trend plot (pressure curve) 21 consists of repeated plots, wherein each plot represents the mean pressure value of the 6 seconds time sequence 11. When only considering the pressure curve 21, it is not possible to know whether the curve is acceptable or not. Examples of absolute mean pressure trend curves 21 are also shown in FIGS. 9a, 9c, 10a, 10c, 11a, and 11c. In FIG. 4c is shown another trend plot wherein the y axis shows absolute mean pressure computed according to Method 2 18 and the x axis the time scale 12. No pressure curve was found in FIG. 4c. Thus, computation of mean pressure within given time sequences according to the method described here (Method 2) gives the major advantage of not computing pressure values when single pressure waves are not identified. When single pressure waves are present, the method gives absolute mean pressure values very similar to the absolute mean pressures computed according to conventional technology.

Reference now is given to FIGS. 5a and 5b. One single wave 1 has the duration from one minimum value ($P_{min}$) back to another minimum value ($P_{min}$), which is the duration of the wave (see FIGS. 1a and 3a). During a time sequence 11, the heart rate 16 may be computed according to two methods (HR-methods 1 and 2). According to the first method (HR-method 1), heart rate 16 is defined as equal to the number of single pressure waves during said time sequence, divided with the duration of said time sequence. With reference to FIG. 5a, heart rate is equal to a number of waves divided by recording time (seconds). During the first time sequence 11 of 6 seconds 7 single pressure waves were identified (I to VII), giving a heart rate of 7/6 seconds (=1.2/second).

Another strategy (HR-method 2) is defining heart rate as numbers of waves divided by the total wavelength of said single pressure waves. In one single pressure wave, the entire wavelength is defined as the duration from $P_{min}$ to $P_{min}$. The heart rate is the number of single pressure waves during a time sequence divided by the duration of the time sequence wherein these waves occurs. Heart rate method 2 is somewhat more accurate than Heart rate method 1, since the first method only includes the duration of the time sequence wherein single waves occurred. With reference to FIG. 5a, the sum of wavelengths (i.e. $P_{min}$-$P_{max}$-$P_{min}$) of the 7 single pressure waves (I to VII) were 5.7 seconds, heart rate would be 7/5.7 seconds (=1.2/second). Some minor differences in heart rate may be computed by the two methods.

The invention includes through its methods of analysis at least two levels of verifying whether a time sequence 11 includes correct single pressure waves: (1) Criteria for accepting or rejecting single pressure waves entering into the time sequences. (2) Criteria for accepting or rejecting the individual time sequence. If the time sequence 11 is not accepted according to the criteria, the time sequence 11 is rejected for further analysis.

First, the main strategy for identification of single waves 1 are related to criteria applied to accepted $P_{min}/P_{max}$ pairs concerning ranges for amplitude ($\Delta P$) 4, latency ($\Delta T$) 5, and rise-time coefficients ($\Delta P/\Delta T$) 6. Single pressure waves not meeting the pre-selected requirements are rejected. A new time sequence 11 is started including the first accepted $P_{min}/P_{max}$ pair, which is the first accepted $P_{min}/P_{max}$ pair that has its final $P_{min}$ 2 within that particular time sequence 11. This has been commented on for FIGS. 2a and 2b. In FIG. 2a is indicated a total of 17 $P_{min}/P_{max}$ pairs. After the single pressure wave criteria were applied to these 17 $P_{min}/P_{max}$ pairs, only a total of 8 $P_{min}/P_{max}$ pairs were accepted (FIG. 2b). However, only 7 single pressure waves (I to VII) were included in the time sequence, as the accepted $P_{min}/P_{max}$ pair following wave VII was not followed by an accepted $P_{min}/P_{max}$ value within the particular time sequence. Therefore, this latter accepted $P_{min}/P_{max}$ pair was included in the subsequent time sequence, provided that an acceptable $P_{min}$ was identified.

Second, criteria may be applied to the individual time sequences 11, determining whether the entire time sequence is accepted or not. The strategy is related to the numbers of single pressure waves (or the heart rate) during the time sequence. During a time sequence the heart rate 16 should be within physiological limits. Ranges for numbers of single waves within a time sequence may be defined. The inventor found it useful to define that the heart rate should be 40-180 (i.e. 4 to 18 single waves within a time sequence of 6 seconds). Thus, time sequences of 6 seconds duration containing a number of single pressure waves outside 4-18 are not accepted for further analysis. Other criteria may as well be used. In addition, thresholds may be defined for accepted variation of numbers of single waves within a time sequence. For several time sequences, standard deviation of numbers of single waves within the time sequence may be computed, wherein time sequences with numbers of single waves deviating too much from standard deviations are rejected.

When several pressures are monitored simultaneously with identical time reference, numbers of single pressure waves within identical time sequences may be compared, as illustrated in FIGS. 5a and 5b. For example, simultaneous monitoring of continuous arterial blood pressure (ABP) (FIG. 5a) and intracranial pressure (ICP) (FIG. 5b) with the same time reference provides the opportunity to compare numbers of waves for these two pressures during identical time sequences. During a given time sequence, numbers of single waves of ICP ($N_{SW-ICP}$) waves should be nearly equal to numbers of single waves of ABP waves ($N_{SW-ABP}$) [$N_{SW-ABP}$−$N_{SW-ICP}$<2]. In the same way, heart rate (HR) derived from single waves of ICP (or CSFp) ($HR_{ICP}$) may be compared with heart rate (HR) of ABP ($HR_{ABP}$). During this recording period, the difference of heart rate (HR) derived from these pressures should be less than 2 [$HR_{ABP}$−$HR_{ICP}$<2]. As illustrated in FIGS. 5a and 5b, the first time sequence (named $1^{st}$) contains seven single pressure waves (named I-VII), identical to the second time sequence (named $2^{nd}$) It should be noted that the numbers of single pressure waves were equal (nos. I-VII) for both arterial blood pressure (FIG. 5a) and intracranial pressure (FIG. 5b) The specific numbers (<2) are only for illustrative purposes and should not be regarded as limitations of the invention.

Comparisons between numbers of waves for one pressure type within a time sequence also may be compared against heart rate measurement from another source, for example pulse oxymetri ($spO_2$), or electrocardiography (ECG). Heart rate 16 during a given recording period derived from either arterial blood pressure or intracranial pressure waves should be equal to heart rate derived from oxygen saturation measurements or by electrocardiography (ECG) [$HR_{P-O2}$−$HR_{ICP}$<2; $HR_{ECG}$−$HR_{ICP}$<2]. The inventor found it useful to use criteria for differences in single waves <2, though other criteria may as well be applied.

For each time sequence 11, all the single waves and single wave parameters are known. Accordingly, standard deviations for all the single pressure wave parameters may be computed. Standard deviations for relative pressures include the parameters amplitude ($\Delta P$) 4, latency ($\Delta T$) 5, and rise time coefficient ($\Delta P/\Delta T$) 6 for all single pressure waves 1 within the time sequences 11. Standard deviations for absolute pressures include absolute pressure values such as mean pressure for all individual single pressure waves (i.e. mean pressure from $P_{min}$ to $P_{min}$ for each individual of all single waves within the time intervals), standard deviations for diastolic minimum ($P_{min}$) 2 for all individual single pressure waves during said time sequence, standard deviations for systolic maximum pressure ($P_{max}$) 3 for all individual single waves 1 during the time sequence 11. Other criteria for acceptance or rejection of a time sequence may be related to limits for the standard deviations referred to here.

Repeated up-dates are made concerning numbers/proportion of accepted and rejected time sequences (and single waves). A log is made for numbers of rejected time sequences and numbers of rejected single pressure waves. A log also is made for reasons of rejection, such as abnormal $\Delta P$ 4, $\Delta T$ 5, $\Delta P/\Delta T$ 6, or abnormal changes in HR 16. Rejected portions of trend plot may be indicated by color of graph or background. Examples of such statistics were made for FIGS. 3b and 4a.

After identification of the single pulse pressure waves 1 during a recording period, the single pressure waves are subject to analysis. Fundamental to the invention is the computation of a matrix 36 of numbers or percentages of single pulse pressure waves with pre-selected wave characteristics. Examples of such characteristics are latencies ($\Delta T$) 5 and amplitudes ($\Delta P$) 4. The matrix 36 of amplitude ($\Delta P$) 4 and latency ($\Delta T$) 5 combinations are referred to as the first matrix in this document. Again, the latencies and amplitudes in the matrix presented in Tables I, V and VI refer to single waves identified by diastolic minimum ($P_{min}$) 2 and systolic maximum ($P_{max}$) 3 values. As indicated, the group of amplitudes are shown oil the horizontal row, and the grouping of the latencies on the vertical column. Each number 37 within the cells of said matrix 36 represents the total numbers of single waves with the given combination of amplitude 4 and latency 5. In another situation the numbers 37 may refer to percentages. When percentages are used, it is against total numbers of waves. The amplitudes 4 are usually expressed in mmHg and the latencies 5 in seconds. The numbers of cells in such a matrix 36 may differ depending on the number of columns and rows. An example is given based on experience of the inventor. For intracranial pressure, the inventor found it useful to use the range of amplitudes ($\Delta P$) 4 equal to 0 to 30.0 mmHg, with intervals of 0.5 mmHg, giving a total of 60 columns. The range of latencies ($\Delta T$) 5 is 0.10 seconds to 0.40 seconds with intervals 0.01 seconds, giving a total of 30 rows. In this matrix the total cell number is 1800. The example represents no limitation of the scope of the invention. For arterial blood pressure, on the other hand, the inventor used the range of amplitudes ($\Delta P$) from 30 to 120 mmHg, with intervals of 2.0 mmHg, giving a total of 45 columns. The range of latencies ($\Delta T$) is 0.10 seconds to 0.40 seconds with intervals 0.01 seconds, giving a total of 30 rows. In this matrix the total cell number is 1350. However, these are only examples, and are not intended to limit the scope of the invention.

An example of a small part of a matrix applied to intracranial pressure is shown in Table I. The matrix 36 (referred to as first matrix) illustrate only a small fraction of a large matrix of 1800 cells.

TABLE I

Part of a matrix of amplitude (ΔP) and latency (ΔT) combinations.

| Group name | Group range | Group midpoint | 0.5<br>$0.5 \leq dP < 1.0$<br>0.75 | 1<br>$1.0 \leq dP < 1.5$<br>1.25 | 1.5<br>$1.5 \leq dP < 2.0$<br>1.75 | 2<br>$2.0 \leq dP < 2.5$<br>2.25 | 2.5<br>$2.5 \leq dP < 3.0$<br>2.75 |
|---|---|---|---|---|---|---|---|
| 0.1 | $0.10 \leq dT < 0.11$ | 0.105 | | | | | |
| 0.11 | $0.11 \leq dT < 0.12$ | 0.115 | | | | | |
| 0.12 | $0.12 \leq dT < 0.13$ | 0.125 | | | 3 | 12 | |
| 0.13 | $0.13 \leq dT < 0.14$ | 0.135 | | 16 | 12 | 8 | |
| 0.14 | $0.14 \leq dT < 0.15$ | 0.145 | | 7 | 5 | 4 | |
| 0.15 | $0.15 \leq dT < 0.16$ | 0.155 | | | | | |

The amplitude (ΔP) 4 values are presented in the columns and the latency (ΔT) 5 values in the rows. For example the first column corresponds to the first amplitude (ΔP) group, named 0.5 (corresponding to 0.5 mmHg); this group includes amplitude (ΔP) 4 values greater or equal to 0.5 mmHg, but less than 1.0 mmHg (indicated by the group range 0.5<ΔP<1). The midpoint (or mean) of the group is 0.75 [(0.5+1.0)/2]. Similarly, the first latency group is termed 0.1, corresponding to a latency of 0.1 seconds. This latency group includes latencies with a duration greater or equal to 0.10 seconds, but less than 0.11 seconds (indicated by the group range 0.10≦ΔT<0.11). The group midpoint is 0.105 [(0.10+0.11)/2]. The amplitude/latency (ΔP/ΔT) matrix can be seen as a two dimensional collection of bins, where the rows are labelled ΔT and the columns are labelled ΔP. A cell equals a bin. Each bin denotes how often ΔP/ΔT combinations have appeared. When the observation is categorized or grouped, the midpoint of the group is used. The data are categorized when the data are in a "range". As an example the first bin in the matrix presented in Table I contains all ΔP values which fall in the range greater or equal to 0.5 mmHg and less than 1 mmHg, with a ΔT value greater or equal to 0.10 seconds and less than 0.11 seconds. The matrix cells found at intersections between columns and rows indicate numbers or proportions of single pressure waves with specific combinations of amplitude (ΔP) and latency (ΔT). The numbers presented in Table I refers to an intracranial pressure recording lasting one minute including 10 time sequences 11, each lasting 6 seconds. During these 6 time sequences a total of 67 single pressure waves occurred. The distribution of the various single pressure waves during this recording period is shown in Table I. For example, single pressure waves 1 with an amplitude (ΔP) 4 greater or equal to 1.5 mmHg but less than 2.0 mmHg and a latency (ΔT) greater or equal to 0.14 seconds, but less than 0.15 seconds occurred 5 times during the time sequence represented in this matrix.

During real time monitoring, the matrix may be computed each 5 seconds. The centre of mass of distribution (balanced position) of single waves with combinations of latency and amplitude may be computed, without taking into account the heart rate. Another implementation may be continuous update of single wave distribution each 5 or 10 seconds. On the monitor display a histogram is presented each 5 seconds in many monitors, though there may be differences between the monitors. The invention does not give any limitations concerning the frequency of updates of matrix.

The preferable approach suggested by the inventor, is repeated computation of the matrix during a continuous pressure monitoring. For each of said time sequences 11 the matrix 36 is computed. For example, with reference to FIG. 5a, one matrix is computed for the first time sequence (named $1^{st}$) and a new matrix computed for the second time sequence (named $2^{nd}$). For the first time sequence 11 (termed $1^{st}$), the matrix 36 contains the amplitude (ΔP) 4 and latency (ΔT) 5 values of seven single pressure waves. For the second time sequence 11 (termed $2^{nd}$), a new matrix 36 is computed also containing seven single pressure waves. For each individual time sequence, new ΔP/ΔT combinations are subsequently entered into the matrix cells during the ongoing pressure measurement. The matrix is updated dynamically during such a 6 seconds time sequence, each cell is updated by adding the new value to the old content. After the 6 seconds interval the procedure is reiterated starting with a new and empty matrix.

The matrix 36 presentations may be subject to various types of analyses. The balanced position within the matrix may be presented as numerical value combinations 38 such as centroid or centre of distribution. According to the present invention, the single waves 1 with pre-selected characteristics of latency 5 and amplitude 4 are computed, and the matrix 36 of single wave combinations computed., with presentation of the distribution of single wave combinations. For the 5 second period the balanced position of single wave combinations may be computed, for example as centroid or centre of distribution. For example, a combination 38 of 0.17|2.0 refers to the single wave combination of latency of 0.17 seconds and amplitude of 2.0 mmHg. During real-time monitoring these numerical value combinations may be updated each time sequence 11 of 5 seconds. In one embodiment, the numerical value combinations 38 may be presented on the display of the apparatus, though this is no limitation of the scope of the invention. For example, presentation on the display of monitoring systems is possible.

The balanced position of single wave combinations, for example determined as centroid or centre of distribution, may also be presented on the y axis in a xy chart with time on the x axis (see FIG. 8e). For example, the centroid or centre of distribution of single wave combinations may be computed repeatedly each 5 second and plotted in the XY-chart during a period of recording. In this situation, the curve reflects numerical value combinations of centroid or centre of distribution of single wave combinations within the histogram or matrix.

Balanced position within a matrix may have different names, such as centroid, centre of distribution, or centre of mass. In this document it is preferred to use the term balanced position. In the context described here, balanced position refers to mean frequency distribution of occurrences of single pressure wave parameters. In this document the terms balanced position of amplitude (ΔP), balanced position of latency (ΔT) and balanced position of rise time coefficient (ΔP/ΔT) are used as terms with respect to the first and seconds matrixes, respectively. However, the term balanced position per se is a method for determining the mean occurrence either within a one- or two-dimensional matrix in general.

With reference to the matrix presented in Table I, the procedure of computing balanced position of the distribution of different amplitude (ΔP) and latency (ΔT) combinations is described. The numbers referred to in Table I relates to a recording period of 1 minute. The method is however, similar whether the recording period is 5, 6 or 10 seconds, or 1 minute or 10 hours. The balanced position relates to the frequency distribution of the different occurrences of amplitude (ΔP) 4 and latency (ΔT) 5 during the selected time period. The method is similar independent on factors such as type of pressure, group ranges, or numbers of cells. Depending on the range of amplitude and latency values, the matrixes may contain a variable number of columns and rows. However, the balanced position result is dependent on the matrix resolution.

With reference to the matrix presented in Table I, the columns refer to amplitude (ΔP) 4 groups and the rows to the latency (ΔT) 5 groups. The system will have i rows, and j columns. When computing balanced position/centroid/mean frequency of such a two-dimensional distribution (referred to as first matrix), both dimensions have to be considered. Since there are two variables the mean (or balanced position) must be given by two numbers, like the ΔT|ΔP values. With reference to Table I, if the values from the row and column mean are considered, the results may be interpreted as the mean value for the distribution. The mean distribution (or balanced position) for the numbers presented in Table I, is located in the crossing point between the two lines ΔP=1.64 and ΔT=0.135. This is the most accurate way to describe the balanced position (or mean value) for this two dimensional distribution. The balanced position in the matrix shown in Table I is ΔP=1.64 and ΔT=0.135, corresponding to the cell with count 12. In the following, some details are given concerning computation of mean row and mean column values. First, the latency (ΔT) mean value (or row mean), with respect to the amplitude (ΔP) values (columns) is determined. The $m_i$ for each latency (ΔT) row is determined, by using the equation 2.

$$m_i = \sum_{j=1}^{j=c} A_j w_{ij} \qquad (2)$$

where $A_j$ is the $j^{th}$ column midpoint, referring to an amplitude (ΔP) group value; $w_{ij}$ is the frequency (count) of the $i^{th}$ ΔT row and $j^{th}$ ΔP column cells. Then, $$\text{Row mean} = \text{Mean}(dt) = \frac{\sum_{i=1}^{r} m_i B_i}{\sum_{i=1}^{r} mi} \qquad (3)$$

where $B_i$ is the $i^{th}$ row ΔT midpoint value (r=row). The term "$i^{th}$ ΔT row and $j^{th}$ ΔP column cell" may also need an explanation. If a horizontal line is drawn through the midpoint in row i, and a vertical line through the midpoint in column j, the two lines will cross each other in a cell. This cell has the coordinates "$i^{th}$ row and $j^{th}$ column cell". As an example, the data of Table I are used to calculate the mean row value. Application of the equations (2) and (3) gives a row mean with respect to columns equal to 0.135 seconds (14.9/110.25). The calculations are shown in more detail in Table II.

TABLE II

Computation of row (latency) mean with respect to columns (amplitude).

| mi | | ΔT i | mi × ΔT i |
|---|---|---|---|
| 3 × 1.25 + 12 × 1.75 = | 24.75 | 0.125 | 3.0925 |
| 16 × 1.25 + 12 × 1.75 +8 × 2.25 = | 59 | 0.135 | 7.965 |
| 7 × 1.25 + 5 × 1.75 + 4 × 2.25 = | 26.5 | 0.145 | 3.8425 |
| Sum = | 110.25 | | 14.9 |

Row mean: 14.9/110.25 = 0.135 seconds

Second, the ΔP mean value (columns), with respect to the ΔT value (rows), is determined. The column ΔP mean value are found using the same approach as used for finding the mean row ΔT value. First, the $m_j$ for each ΔP column is found, as given in equation (4).

$$m_j = \sum_{i=1}^{i=r} B_i w_{ij} \qquad (4)$$

where $B_i$ is the $i^{th}$ row ΔT midpoint, and referring to a ΔT group value and $w_{ij}$ is the frequency for the $i^{th}$ row and $j^{th}$ column. Then, $$\text{Column mean} = \text{Mean}(dP) = \frac{\sum_{j=1}^{j=c} m_j A_j}{\sum_{j=1}^{j=c} mi} \qquad (5)$$

where $A_j$ is the $j^{th}$ column ΔP value midpoint (c=column). The calculations are shown in Table III, using the equations (4) and (5), the column mean with respect to rows will be equal to 1.64 mmHg (14.9/9.055).

TABLE III

Computation of column (amplitude) mean with respect to rows (latency).

| Column | mj | | ΔPj | mj × ΔPj |
|---|---|---|---|---|
| 1 | | | | |
| 2 | 3 × 0.125 + 16 × 0.135 +7 × 0.145 = 3.55 | | 1.25 | 4.4375 |
| 3 | 12 × 0.125 + 12 × 12 × 0.135 + 5 × 0.145 = 3.845 | | 1.75 | 6.72875 |
| 4 | 8 × 0.135 + 4 × 0.145 + 4 × = 1.66 | | 2.25 | 3.735 |
| 5 | | | | |
| | Sum | | 9.055 | 14.9 |

Column mean: 14.9/9.055 = 1.64 mmHg

Finally, it should be mentioned that balanced position may as well be determined within a one-dimensional matrix (termed second matrix). Such a matrix is used for determining balanced position of occurrences of rise-time coefficients during a given time sequence. It may be used for other one-dimensional matrix variables/relations as well. In this situation the rise time coefficients are plotted in a one-dimensional matrix of pre-defined rise time coefficients. In such a one-dimensional frequency distribution we have two variables $x_i$, and $w_i$ ($x_i$ equal to the value of each observation, $w_i$ equal to the frequency or count). $x_i$ is comparable to $\Delta P/\Delta T$ and $w_i$ is comparable to the number of occurrences of the various $\Delta P/\Delta T$ combinations. The mean of this distribution may be computed according to equation 6:

$$\overline{X} = \frac{\sum_{i=1}^{k} x_i w_i}{\sum_{i=1}^{k} w_i}, k = \text{number of observations} \quad (6)$$

It has been discussed computation of a two-dimensional matrix of combinations of amplitude ($\Delta P$) and latency ($\Delta T$) combinations (referred to as the first matrix), and also computation of a one-dimensional matrix of combinations of rise-time coefficients ($\Delta P/\Delta T$) (referred to as the second matrix). It should be noted that these are examples, and not intended to limit the scope of the invention. A matrix may contain any of the single pressure wave parameters discussed in this document, and any combinations are possible. Matrixes may be computed for any type of pressure. The numbers of groups may be selected.

Figure 6A:
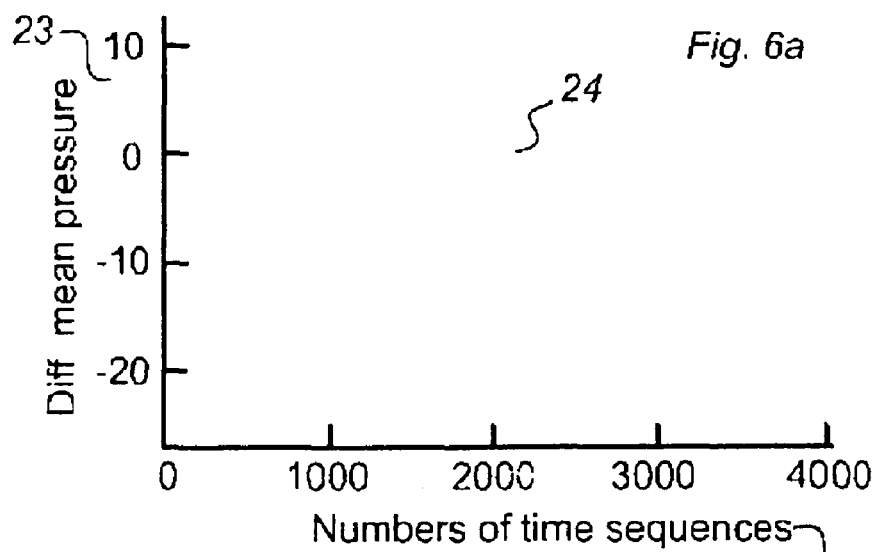
FIG. 6 shows a differential plot of two simultaneous continuous pressure recordings with identical time reference with regard to (a) absolute mean pressure, (b) balanced position of amplitude, and (c) balanced position of latency.
Figure 6B:
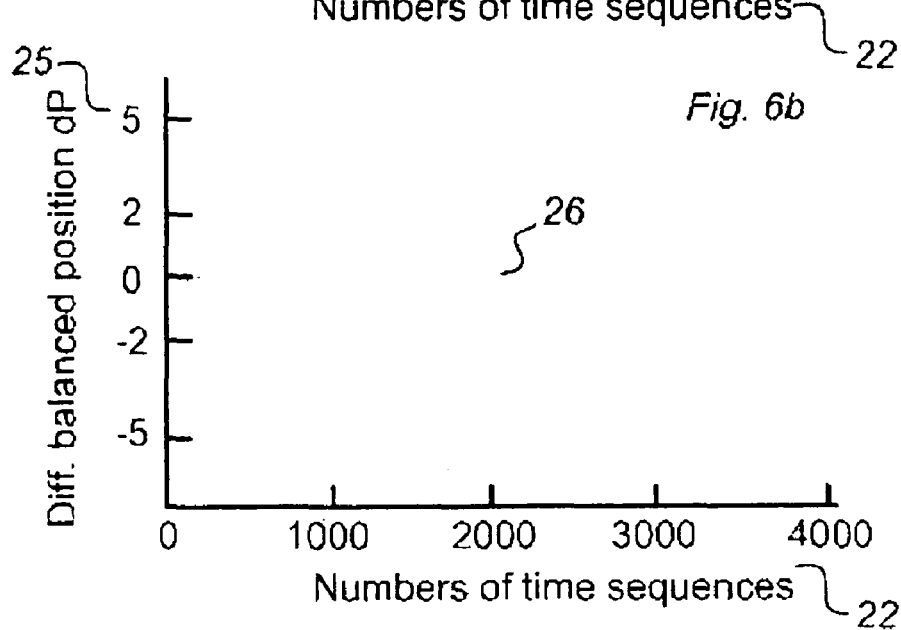
Figure 6C:
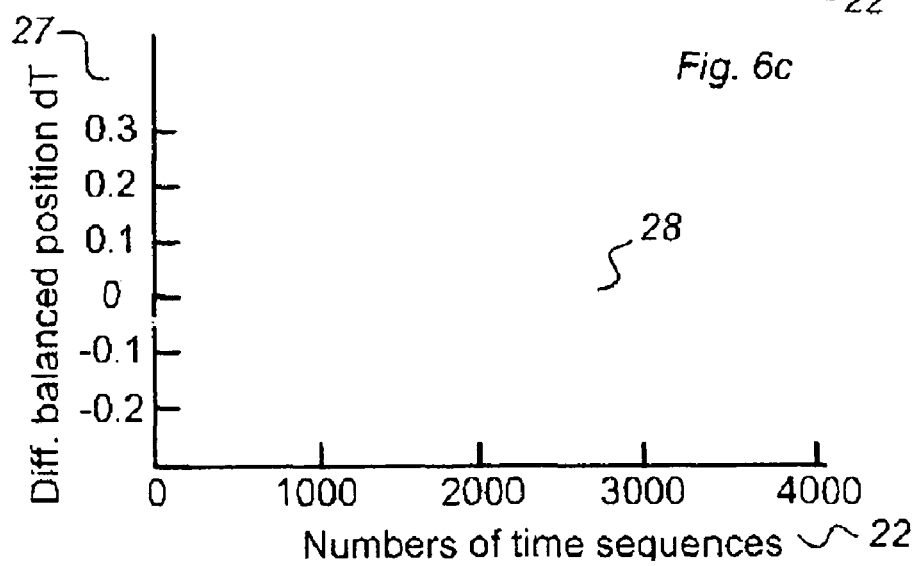

Reference is now given to FIGS. 6a-c. This figure illustrates differences between computation of absolute mean pressure and single pressure wave parameters. Intracranial pressure was measured simultaneously by means of two different sensors located within the brain parenchyma, separated by 1-2 centimetres. Intracranial pressure would be expected to be similar, given the narrow location between the sensors. Intracranial pressure was measured simultaneously by the two sensors. Since measurements had identical time reference, the single pressure wave parameters computed within given time sequences of 6 seconds duration could be compared time sequence for time sequence. For each time sequence 11 absolute mean pressure was computed according to Method 2, as well as balanced position of amplitude ($\Delta P$) and balanced position of latency ($\Delta T$). Time sequence for time sequence in the continuous series of time sequences, differences between the two pressure recordings were computed with regard to absolute mean pressure (FIG. 6a), balanced position of amplitude ($\Delta P$) (FIG. 6b), and balanced position of latency (FIG. 6c). With reference to FIG. 6a, on the x axis is shown the number of the time sequences 22. In this recording period, the first time sequence starts with number 1 and the last time sequence ends with number 4100, indicating the start and end of the recording period, respectively. Thus, the continuous recording period consisted of a series of 4100 continuous time sequences 11, corresponding to 24600 seconds (6.8 hours). On the x axis is indicated the scale for differences in absolute mean pressure 23. The differential pressure curve 24 shows the trend distribution of differences in absolute pressure within identical time sequences for two pressure recordings with different sensors. Each plot within said differential plot 24 presents differences within identical time sequences for absolute mean pressure, wherein differences related to pressures measured by either of said two sensors. A large variation in absolute pressures is shown. For time sequence number 1000, absolute mean pressure was 20.2 mmHg for sensor 1 and 33.3 mmHg for sensor 2, with a difference in mean pressure of −13.1 mmHg. In FIG. 6b is indicated on the y axis differences in balanced position of amplitude ($\Delta P$) 25 and the series of time sequences 22 on the x axis. The differential curve of balanced position 26 shows for consecutive time sequences differences in balanced position of amplitude ($\Delta P$). The trend curve show 25 that differences in balanced position of amplitude ($\Delta P$) between identical time sequences are minimal. For time sequence number 1000, balanced position of amplitude was 5.2 mmHg for sensor 1 and 5.6 mmHg for sensor 2. Difference in balanced position was 0.4 mmHg. In the same way, differences in balanced position of latency are shown in FIG. 6c. In FIG. 6c is shown on the y axis differences in balanced position of latency ($\Delta T$) 27 and on the x axis the consecutive series of time sequences 22. The differential trend plot of balanced position of latency ($\Delta T$) 28 show minimal differences between balanced position of latency ($\Delta T$) for different pressure curves using different sensors with identical time sequences. The results presented in FIG. 6a-c suggest that pressures are less reliably predicted by absolute mean pressure, as compared to balanced position of amplitude ($\Delta P$) and latency ($\Delta P$). Again it should be noted that differences were computed on a beat to beat basis since the time reference was identical.

With regard to time sequences, absolute mean pressure and balanced position of either amplitude ($\Delta P$) or latency ($\Delta P$) are only few of many different single pressure wave parameters. The various parameters related to single pressure waves 1 are discussed in the following. An inventive step of this invention is to store in a database the single pressure wave related parameters computed according to the invention. The single wave 1 related parameters relate to said time sequences 11. Before creating a database, the duration of said time sequences may be selected. The inventor suggest that the duration preferably should be of 5-15 seconds duration. Specific durations of said time sequences are not a limitation. The inventor computed a database wherein time sequences of 6 seconds duration were selected. Within each time sequence the single wave related parameters may either be related to each of the individual single pressure waves within said time sequence, or to the group of individual single waves within said time sequence.

For each of the individual single pressure waves 1 within said time sequence 11, the following parameters are stored (referred to as Single wave parameters 1-6):

1. Absolute pressure value for diastolic minimum ($P_{min}$) 2 value for each individual single pressure wave 1 (i.e. accepted $P_{min}/P_{max}$ pair) during said time sequence 11.
2. Absolute pressure value for systolic maximum ($P_{max}$) 3 value for each individual single pressure wave 1 (i.e. accepted $P_{min}/P_{max}$ pair) during said time sequence 11.
3. Absolute mean pressure for each accepted single wave 1 (i.e. accepted $P_{min}/P_{max}$ pair) (related to each accepted $P_{min}/P_{max}$ pair), that is mean pressure from $P_{min}$ to $P_{min}$ (wavelength) 7 for each individual single pressure wave 1 during said time sequence 11.
4. Relative amplitude ($\Delta P$) 4 pressure value for each individual single pressure wave 1 (i.e. accepted $P_{min}/P_{max}$ pair) during said time sequence 11.
5. Relative latency ($\Delta T$) 5 value for each individual single pressure wave 1 (i.e. accepted $P_{min}/P_{max}$ pair) during said time sequence 11.
6. Relative rise time coefficient ($\Delta P/\Delta T$) 6 value for each individual single pressure wave 1 (i.e. accepted $P_{min}/P_{max}$ pair) during said time sequence 11.

For the group of single pressure waves within said time sequence 11, the following parameters are stored (referred to as time sequence parameters 1-12):

1. Numbers of single waves ($N_{sw}$) during said time sequence.
2. Single pressure wave derived heart rate 16, computed as numbers of single pressure waves 1 divided with the total duration of wavelengths ($P_{min}$ to $P_{min}$) 7 of single pressure waves within said time sequence 11.
3. Single pressure wave derived heart rate 16, computed as numbers of single pressure waves 1 divided with the duration of said time sequence 11 wherein said single pressure waves occur.
4. Absolute mean pressure for said time sequence 11, computed as the sum of absolute mean pressure (entire wavelength 7 from $P_{min}$ to $P_{min}$ for all individual single waves 1 during said time sequence 11, divided by numbers of single waves within said time sequence 11 (referred to as Method 2).
5. Standard deviation for mean pressure of mean pressure for the individual single waves 1 occurring during said time sequence 11.
6. Standard deviation for diastolic minimum ($P_{min}$) 2 during said time sequence, which is computed as standard deviation for diastolic minimum ($P_{min}$) 2 of all individual single waves 1 during said time sequence 11
7. Standard deviation for systolic maximum ($P_{max}$) 3 during said time sequence 11, which is computed as standard deviation for systolic maximum ($P_{max}$) 3 of all individual single waves 1 occurring during said time sequence 11.
8. Standard deviation for amplitude ($\Delta P$) 4 of all individual single pressure waves 1 occurring during said time sequence 11.
9. Standard deviation for latency ($\Delta T$) 5 of all individual single pressure waves 1 occurring during said time sequence 11.
10. Standard deviation for rise time coefficient ($\Delta P/\Delta T$) 6 of all individual single pressure waves 1 occurring during said time sequence 11.
11. Balanced position of amplitude ($\Delta P$)/latency ($\Delta T$) combinations in said amplitude/latency matrix (referred to as first matrix).
12. Balanced position of rise time coefficients ($\Delta P/\Delta T$) in rise time coefficient matrix (referred to as second matrix).

All the single pressure wave related parameters are computed for each time sequence. Given that the duration of each time sequence is set to 6 seconds, an individual recording of 10 hours consists of 6000 time sequences. For example, the sole parameter Balanced position of amplitude ($\Delta P$) and latency ($\Delta T$) consists of two values (e.g. 0.12 seconds 16.25 mmHg), that gives 12000 values during a 10 hours recording period (20 values/minute×60 minutes/hr×10 hrs). These 12000 values include 6000 values of balanced position amplitude ($\Delta P$) 4 and 6000 values of balanced position latency ($\Delta T$) 5. Thus, for every time sequence the single wave related parameters are stored. The inventor first created a database based on time sequences of 6 seconds. At an early stage the database consisted of several millions of said time sequences. Since the data are continuous, it is easy to change the duration of the time sequence (e.g. to 5 seconds duration), though the computer requires time to process the digital data.

The database serves several purposes; an important purpose is to determine relationships between the different single wave parameters. Since relationships between several parameters within identical time sequences may be determined, it is also possible to determine one parameter as a function of two or more other parameters. For example, for one individual pressure recording, the single pressure wave parameters within each time sequence may be related. This procedure may be computed in a scatter plot with one parameter on the y axis and the other on the x axis. An example is given. A continuous pressure recording of 10 hours contains a total of 6000 time sequences, each lasting 6 seconds. Provided that 5400 of 6000 time sequences are accepted from said pressure recording, this pressure recording contains a total of 5400 values of balanced position of amplitude ($\Delta P$) 4 and 5400 values of latency ($\Delta T$) 5. In a scatter plot each value refers to a combination of balanced position of amplitude ($\Delta P$) 4 and balanced position of latency ($\Delta T$) 5. The relationships between the 5400 plots may further be determined by computing the best fitted curve. Goodness of fit may be determined by various strategies. For a given relationship, it is the experience of the inventor that the goodness of fit as well as the spread of the plot may differ among different pressure recordings.

The relationships between parameters may as well be determined for a group of individual pressure recordings. For example, for a group of 100 individual pressure recordings the relationships between balanced positions of amplitude ($\Delta P$) 4 and latency ($\Delta T$) 5 may be determined. Given that each individual pressure recording contains an average of 5400 values of balanced position of amplitude ($\Delta P$) 4 and 5400 values of balanced position of latency ($\Delta T$) 5, an averaged total of 540000 values of each variable is available. Various mathematical procedures are possible to determine the relationships between these variables in such a large sample. A scatter of 540000 plots may be made. A relationship may as well be made by a random selection of the total material. The invention does not limit to a particular strategy for determining relationships within a large material, as various mathematical strategies are possible.

In FIGS. 7*a-c* addresses the topic of determining relationships between single pressure wave parameters within a group of individual pressure recordings. This is an example of one strategy, though this example is not intended to limit the scope of the invention. The data presented in FIGS. 6*a-c* represents a total of 40 individual pressure recordings. These 40 individual pressure recordings contain a total of 330540 individual time sequences 11, each lasting 6 seconds. First, each individual of said 40 individual pressure recordings were considered. For each individual pressure recording, the best fitted equation is determined for ranges of the parameters wherein the curve is based. For example, for one pressure recording the best fitted equation was applicable for the amplitude ($\Delta P$) ranges of 2.5 to 6.7 mmHg, whereas another pressure recording determined the best fitted equation for the amplitude ($\Delta P$) ranges of 5.4 to 12.0 mmHg. Second, the best fitted curves 31 from the individual pressure recordings were sampled within a scatter of all 40 individual pressure recordings. In FIG. 7*a* the y axis shows the balanced position values of amplitude ($\Delta P$) values 29, and the x axis the balanced position of latency ($\Delta T$) 30. In FIG. 6*b* is balanced position of amplitude ($\Delta P$) values 29 on the y axis plotted against absolute mean pressure (computed according to Method 2) 18 on the x axis. In FIG. 6*a* is indicated the regression line 31 corresponding to individual pressure recordings of the relationship between balanced position of amplitude ($\Delta P$) and latency ($\Delta T$). The total regression line 32 for all individual pressure recordings is shown. This corresponds to the relationship between balanced position of amplitude ($\Delta P$) and latency ($\Delta T$) for the whole group of 40 individual pressure recordings including 330540 time sequences. The relationship is exponential. In FIG. 7*b* is shown the regression lines 33 for the individual pressure recordings for the relationship between balanced position of amplitude ($\Delta P$) 29 and absolute mean pressure 18. The total regression line 34 for all individual regression lines concerning relationship between balanced position of amplitude ($\Delta P$) 29 and absolute mean pressure 18 is shown in FIG. 6*b*. The equation of the total regression line 32 of FIG. 6a may be combined with the equation of the total regression line 34 of FIG. 6b. Since both equations contain the variable balanced position of amplitude ($\Delta P$) 29, it is possible to compute one of the variables as a function of the others. This aspect is further illustrated in FIG. 6c, wherein the variables balanced position of amplitude ($\Delta P$) 29, balanced position of latency ($\Delta T$) 30, and absolute mean pressure 18 are plotted are plotted in a 3D graph. In FIG. 7c is shown a graphical presentation of the three-dimensional regression line 35 based on the equation of the three variables balanced position of amplitude ($\Delta P$) 29, balanced position of latency ($\Delta T$) 30, and absolute mean pressure 18. The equation of this three-dimensional regression line shows one variable as a function of the two other variables. Independent of the method, the following model was computed for this particular relationship: Mean pressure $= a + b_1 \times \Delta P + b_2 \times \Delta T^3$. On this basis an equation was determined:

$$\text{Predicted mean pressure} = 3.214 + 1.3 \times \Delta P + 63.609 \times \Delta T^3 \qquad (7)$$

It should be noted that this equation is relevant for the data presented in FIGS. 7a and 7b. For other materials, other equations may be computed. This equation is included to give an example of how one single pressure wave parameter may be expressed as a function of two other single pressure wave parameters. The data have been selectively chosen, but contains a huge number of comparisons. The data shown in these figures consist of 330540 individual time sequences 11, each lasting 6 seconds. Nevertheless, an important question is how to establish a database of individual pressure recordings that may provide a reliable relationship between the single pressure wave parameters. According to this invention, selected criteria are established to determine whether or not an individual pressure recording may be included in determining the relationship between single pressure wave parameters. Not all scatter plots of single pressure wave parameters are useful for determining fitted curve formulas since the variation within the plot may be very large. Determination of goodness of fit for regression lines of individual pressure recordings may be made by various strategies. An important issue is also to determine which parameters that do or do not influence on each other.

An important aspect of determining relationships between single pressure wave related parameters is an inventive procedure of giving weights to cells within a matrix. Reference has been made to said first matrix of amplitude ($\Delta P$) and latency ($\Delta T$) combinations (see Table I). The cells within the matrix described in Table I may be represented as weight values. Instead of the word weight, the word score might be used. In this description the word weight is preferred. A weighted cell value means that each cell in said matrix (see Table I) is represented by one value instead of two values corresponding to the respective column and row numbers. According to the invention, weight values are made on the basis of observations. In this context, observations refer to the relationships established by means of the database.

Reference is now given to Table IV that is a weight matrix. The group names, ranges and midpoints correspond to the amplitude/latency matrix shown in Table I. For example, the amplitude (AP) group named 1.5 mmHg includes amplitude values equal to or larger than 1.5 mmHg but less than 2.0 mmHg, with group midpoint value equal to 1.75 mmHg. The latency ($\Delta T$) group termed 0.11 seconds includes latency values equal to or larger than 0.11, but less than 0.12 seconds, with group midpoint value of 0.115 seconds. With reference to Table IV, the equation of the relationships presented in FIG. 7c was used to give each individual cell in said matrix a weight value. The weight value was considered as equal to predicted mean (Predicted mean pressure$=3.214+1.3 \times \Delta P + 63.609 \times \Delta T^3$). The equation was applied to each amplitude and latency group within said matrix. The equation describes the predicted mean value as a function of the balanced position of amplitude ($\Delta P$) and latency ($\Delta T$) values. With reference to Table IV, the group midpoint values of amplitude ($\Delta P$) and latency ($\Delta T$) groups were used as input values to the equation to give each cell a predicted mean value. For example, buy using the equation 7 related to FIG. 7c (Predicted mean pressure$=3.214+1.3 \times \Delta P + 63.609 \times \Delta T^3$), the cell corresponding to amplitude ($\Delta P$) group 1.5 mmHg (with group midpoint 0.115 seconds) would be represented with the predicted mean pressure value of 5.59 mmHg. In this example the whole matrix is weighted according to the equation computed according to the relationships presented in FIGS. 7a to 7c. Based on the relationships presented in FIGS. 7a to 7c, it is also possible to compute one individual equation for each amplitude ($\Delta P$) group within said matrix. Thereby, each equation is applicable for ranges of amplitude ($\Delta P$), for example the ranges $0.5 < \Delta P \leq 1.0$ mmHg. Matrix cells of an amplitude ($\Delta P$)/latency ($\Delta T$) matrix can be represented by selected colors corresponding to the mean pressure values of said matrix.

It should be noted that the numbers and equations presented are used as illustrative examples and are not intended to limit the scope of the invention. The weight values computed depend on the relationships determined according to the observational data. Which absolute pressure levels that correspond to which balanced position $\Delta P$ and $\Delta T$ levels depend on the fitted curve equations computed for the particular data set. The invention sets no limitations concerning which types of observations the relationships are based on. Preferentially the plots should be based on a group of patients. However, separate plots may be made for different patient groups, patient ages, and disease states. These curves may to some extent differ depending on the types of pressures measured, compartments where pressures are measured, method by which pressures are measured, age of patient in whom pressures are measured, as well as disease state of the patient. In these situations certain weight matrixes may be used only for particular patient groups or disease states.

TABLE IV

A part of a weight matrix wherein the number in each matrix cell is a weight value that is a function of the amplitude (dP) and latency (dT) values.

| Group name | | | 0.5 | 1 | 1.5 | 2 | 2.5 |
|---|---|---|---|---|---|---|---|
| | Group range | | $0.5 < dP < 1.0$ | $1.0 < dP < 1.5$ | $1.5 < dP < 2.0$ | $2.0 < dP < 2.5$ | $2.5 < dP < 3.0$ |
| | | Group midpoint | 0.75 | 1.25 | 1.75 | 2.25 | 2.75 |
| 0.1 | $0.10 < dT < 0.11$ | 0.105 | 4.26 | 4.91 | 5.56 | 6.21 | 6.86 |
| 0.11 | $0.11 < dT < 0.12$ | 0.115 | 4.29 | 4.94 | 5.59 | 6.24 | 6.89 |
| 0.12 | $0.12 < dT < 0.13$ | 0.125 | 4.31 | 4.96 | 5.61 | 6.26 | 6.91 |

TABLE IV-continued

A part of a weight matrix wherein the number in each matrix cell is a weight value that is a function of the amplitude (dP) and latency (dT) values.

| | | | | | | | |
|---|---|---|---|---|---|---|---|
| 0.13 | 0.13 < dT < 0.14 | 0.135 | 4.35 | 5.00 | 5.65 | 6.30 | 6.95 |
| 0.14 | 0.14 < dT < 0.15 | 0.145 | 4.38 | 5.03 | 5.68 | 6.33 | 6.98 |
| 0.15 | 0.15 < dT < 0.16 | 0.155 | 4.43 | 5.08 | 5.73 | 6.38 | 7.03 |
| 0.16 | 0.16 < dT < 0.17 | 0.165 | 4.47 | 5.12 | 5.77 | 6.42 | 7.07 |
| 0.17 | 0.17 < dT < 0.18 | 0.175 | 4.53 | 5.18 | 5.83 | 6.48 | 7.13 |
| 0.18 | 0.18 < dT < 0.19 | 0.185 | 4.59 | 5.24 | 5.89 | 6.54 | 7.19 |
| 0.19 | 0.19 < dT < 0.20 | 0.195 | 4.66 | 5.31 | 5.96 | 6.61 | 7.26 |
| 0.2 | 0.20 < dT < 0.21 | 0.205 | 4.74 | 5.39 | 6.04 | 6.69 | 7.34 |
| 0.21 | 0.21 < dT < 0.22 | 0.215 | 4.82 | 5.47 | 6.12 | 6.77 | 7.42 |
| 0.22 | 0.22 < dT < 0.23 | 0.225 | 4.91 | 5.56 | 6.21 | 6.86 | 7.51 |
| 0.23 | 0.23 < dT < 0.24 | 0.235 | 5.01 | 5.66 | 6.31 | 6.96 | 7.61 |
| 0.24 | 0.24 < dT < 0.25 | 0.245 | 5.12 | 5.77 | 6.42 | 7.07 | 7.72 |
| 0.25 | 0.25 < dT < 0.26 | 0.255 | 5.24 | 5.89 | 6.54 | 7.19 | 7.84 |
| 0.26 | 0.26 < dT < 0.27 | 0.265 | 5.37 | 6.02 | 6.67 | 7.32 | 7.97 |
| 0.27 | 0.27 < dT < 0.28 | 0.275 | 5.51 | 6.16 | 6.81 | 7.46 | 8.11 |
| 0.28. | 0.28 < dT < 0.29 | 0.285 | 5.66 | 6.31 | 6.96 | 7.61 | 8.26 |
| 0.29 | 0.29 < dT < 0.30 | 0.295 | 5.82 | 6.47 | 7.12 | 7.77 | 8.42 |
| 0.3 | 0.30 < dT < 0.31 | 0.305 | 5.99 | 6.64 | 7.29 | 7.94 | 8.59 |
| 0.31 | 0.31 < dT < 0.32 | 0.315 | 6.18 | 6.83 | 7.48 | 8.13 | 8.78 |
| 0.32 | 0.32 < dT < 0.33 | 0.325 | 6.37 | 7.02 | 7.67 | 8.32 | 8.97 |
| 0.33 | 0.33 < dT < 0.34 | 0.335 | 6.58 | 7.23 | 7.88 | 8.53 | 9.18 |
| 0.34 | 0.34 < dT < 0.35 | 0.345 | 6.80 | 7.45 | 8.10 | 8.75 | 9.40 |
| 0.35 | 0.35 < dT < 0.36 | 0.355 | 7.03 | 7.68 | 8.33 | 8.98 | 9.63 |
| 0.36 | 0.36 < dT < 0.37 | 0.365 | 7.28 | 7.93 | 8.58 | 9.23 | 9.88 |
| 0.37 | 0.37 < dT < 0.38 | 0.375 | 7.54 | 8.19 | 8.84 | 9.49 | 10.14 |
| 0.38 | 0.38 < dT < 0.39 | 0.385 | 7.82 | 8.47 | 9.12 | 9.77 | 10.42 |
| 0.39 | 0.39 < dT < 0.40 | 0.395 | 8.11 | 8.76 | 9.41 | 10.06 | 10.71 |
| 0.4 | 0.40 < dT < 0.41 | 0.405 | 8.41 | 9.06 | 9.71 | 10.36 | 11.01 |
| Group name | | | 3 | 3.5 | 4 | 4.5 | 5 |
| | Group range | | 3.0 < dP < 3.5 | 3.5 < dP < 4.0 | 4.0 < dP < 4.5 | 4.5 < dP < 5.0 | 5.0 < dP < 5.5 |
| | | Group midpoint | 3.25 | 3.75 | 4.25 | 4.75 | 5.25 |
| 0.1 | 0.10 < dT < 0.11 | 0.105 | 7.51 | 8.16 | 8.81 | 9.46 | 10.11 |
| 0.11 | 0.11 < dT < 0.12 | 0.115 | 7.54 | 8.19 | 8.84 | 9.49 | 10.14 |
| 0.12 | 0.12 < dT < 0.13 | 0.125 | 7.56 | 8.21 | 8.86 | 9.51 | 10.16 |
| 0.13 | 0.13 < dT < 0.14 | 0.135 | 7.60 | 8.25 | 8.90 | 9.55 | 10.20 |
| 0.14 | 0.14 < dT < 0.15 | 0.145 | 7.63 | 8.28 | 8.93 | 9.58 | 10.23 |
| 0.15 | 0.15 < dT < 0.16 | 0.155 | 7.68 | 8.33 | 8.98 | 9.63 | 10.28 |
| 0.16 | 0.16 < dT < 0.17 | 0.165 | 7.72 | 8.37 | 9.02 | 9.67 | 10.32 |
| 0.17 | 0.17 < dT < 0.18 | 0.175 | 7.78 | 8.43 | 9.08 | 9.73 | 10.38 |
| 0.18 | 0.18 < dT < 0.19 | 0.185 | 7.84 | 8.49 | 9.14 | 9.79 | 10.44 |
| 0.19 | 0.19 < dT < 0.20 | 0.195 | 7.91 | 8.56 | 9.21 | 9.86 | 10.51 |
| 0.2 | 70.20 < dT < 0.21 | 0.205 | 7.99 | 8.64 | 9.29 | 9.94 | 10.59 |
| 0.21 | 0.21 < dT < 0.22 | 0.215 | 8.07 | 8.72 | 9.3 | 10.02 | 10.67 |
| 0.22 | 0.22 < dT < 0.23 | 0.225 | 8.16 | 8.81 | 9.46 | 10.11 | 10.76 |
| 0.23 | 0.23 < dT < 0.24 | 0.235 | 8.26 | 8.91 | 9.56 | 10.21 | 10.86 |
| 0.24 | 0.24 < dT < 0.25 | 0.245 | 8.37 | 9.02 | 9.67 | 10.32 | 10.97 |
| 0.25 | 0.25 < dT < 0.26 | 0.255 | 8.49 | 9.14 | 9.79 | 10.44 | 11.09 |
| 0.26 | 0.26 < dT < 0.27 | 0.265 | 8.62 | 9.27 | 9.92 | 10.57 | 11.22 |
| 0.27 | 0.27 < dT < 0.28 | 0.275 | 8.76 | 9.41 | 10.06 | 10.71 | 11.36 |
| 0.28 | 0.28 < dT < 0.29 | 0.285 | 8.91 | 9.56 | 10.21 | 10.86 | 11.51 |
| 0.29 | 0.29 < dT < 0.30 | 0.295 | 9.07 | 9.72 | 10.37 | 11.02 | 11.67 |
| 0.3 | 90.30 < dT < 0.31 | 0.305 | 9.24 | 9.89 | 10.54 | 11.19 | 11.84 |
| 0.31 | 0.31 < dT < 0.32 | 0.315 | 9.43 | 10.08 | 10.73 | 11.38 | 12.03 |
| 0.32 | 0.32 < dT < 0.33 | 0.325 | 9.62 | 10.27 | 10.92 | 11.57 | 12.22 |
| 0.33 | 0.33 < dT < 0.34 | 0.335 | 9.83 | 10.48 | 11.13 | 11.78 | 12.43 |
| 0.34 | 0.34 < dT < 0.35 | 0.345 | 10.05 | 10.70 | 11.35 | 12.00 | 12.65 |
| 0.35 | 0.35 < dT < 0.36 | 0.355 | 10.28 | 10.93 | 11.58 | 12.23 | 12.88 |
| 0.36 | 0.36 < dT < 0.37 | 0.365 | 10.53 | 11.18 | 11.83 | 12.48 | 13.13 |
| 0.37 | 0.37 < dT < 0.38 | 0.375 | 10.79 | 11.44 | 12.09 | 12.74 | 13.39 |
| 0.38 | 0.38 < dT < 0.39 | 0.385 | 11.07 | 11.72 | 12.37 | 13.02 | 13.67 |
| 0.39 | 0.39 < dT < 0.40 | 0.395 | 11.36 | 12.01 | 12.66 | 13.31 | 13.96 |
| 0.4 | 10.40 < dT < 0.41 | 0.405 | 11.66 | 12.31 | 12.96 | 13.61 | 14.26 |

In FIG. 8 is illustrated how determination of single wave distribution may be used in the real-time and online monitoring of pressures. The first sequence of events is indicated in FIGS. 8a to 8c, providing a schematic overview of computing balanced position of amplitude/latency combinations within consecutive time sequences 11. Pressure signals from any type of pressure sensor may be sampled, and the single waves 1 identified. Within each time sequence 11 (illustrated with a duration of 5 seconds; FIG. 8a), the single pressure waves 1 are identified. In FIG. 8a is indicated seven single pressure waves within the time sequence 11 of 5 seconds. For all accepted single pressure waves 1 within said time sequence 11, the single pressure wave parameters amplitude ($\Delta P$) 4 and latency ($\Delta T$) 5 are plotted in a first matrix 36. The first matrix 36 in FIG. 8b represents only a small part of a matrix 36 for intracranial pressure. The numbers 37 presented in the matrix are numbers of single waves with different combinations of latency 5 and amplitude 4 during said time sequence 11. An alternative to presenting numbers is presentation of percentages of combinations. With refernce to FIG. 8b, the numbers of occurrences of single waves with amplitude of 2.0 mmHg and a latency of 0.13 seconds was 2 during said time sequence of 5 seconds. For this matrix 36 the numerical value 38 of balanced position of amplitude and latency combinations was 0.12 seconds|2.4 mmHg (FIG. 8c). This combination of 0.12|2.4 refers to the single pressure wave combination wherein latency 5 was 0.12 seconds and amplitude 42.4 mmHg. In fact, various terms may be used concerning balanced position such as centre of mass or centroid. In this context, the balanced position refers to the mean frequency distribution of amplitude 4 and latency 5 combinations within said time sequence 11 and represented in said matrix 36, as previously described in detail. The procedure in FIGS. 8a-c is repeated every new time sequence 11 in the continuous series of time sequences 11 during a continuous pressure monitoring. Accordingly a new balanced position is computed each new 5 seconds in this particular example. During real-time monitoring these numerical value combinations may be updated each 5 seconds. The numerical value combinations 38 may be presented on the display of an apparatus or a monitor.

During on-line monitoring it may be difficult for the physician or nurse to relate to new numerical values presented each 5 seconds. Therefore, various examples of presentations are given in FIGS. 8d-f. In all these examples the two-dimensional values of balanced position are presented as one-dimension values. According to this invention this is made possible by weighting of the matrix cells. Thereby, the two-dimensional balanced position may be represented by a one-dimensional weighted value. In FIG. 8d is shown a histogram presentation with numbers or proportions 39 on the y axis and weighted balanced position 40 values on the x axis. For example, such a histogram may reveal for a given recording period the total distribution of weighted values of balanced positions 40 of amplitude and latency within the time sequences occurring during said recording period, as further shown in FIGS. 9b, 9d, 10b, and 10d. In such a histogram each bar 41 represents a given weighted value of balanced position of amplitude and latency within said 5-second time sequences, with the numbers or proportions of said Weighted values represented on the x axis. In FIG. 8e is presented weighted values of balanced position 40 of amplitude/latency combinations in a trend plot, with time scale 12 on the x axis and weighted values of balanced position 40 on the y axis. In the trend plot 42 each plot represents a weighted value of balanced position 40 of amplitude and latency within a time sequence of 5 seconds. Thus, the trend plot shows the output of analysis of each time sequence in a continuous series of time sequences. Criteria may be selected for handling excluded time sequences. Examples of trend plots 42 of weighted values are further given in FIGS. 11b and 11d. A third alternative of presenting single wave distribution is indicated in FIG. 8f. A modification of a so-called pressure volume curve may be computed for a large number of individuals. Such a curve may depend on age. The inventor has computed so-called pressure volume curves for adults by means of so-called infusion tests, previously described in U.S. patent application Ser. No. 09/843,702 and International Patent Application PCT/NO 02/00164. On the X-axis is indicated change of volume 43. On the Y-axis is indicated the balanced position 40 of amplitude and latency. During so-called infusion tests a fixed volume is applied to the intracranial compartment, for example with similar volume changes each 5 seconds. During each 5 seconds the single waves are monitored with computation of matrix 36. The balanced position 40 may be computed, and expressed on the Y-axis. The fixed volume change 43 is indicated on the X-axis. The inventor has been able to compute such pressure volume curves for a large number of patients. Thereby reference curves have been computed, indicating both normal and abnormal curves. Such reference curves may be shown on the display of the apparatus or on other monitor systems. During real-time monitoring the balanced position of single wave combinations may be plotted in relation to the modified pressure volume curve, for example each 5 seconds. Thereby, real-time and online update of balanced position for a single case may be computed real-time and online and related to a reference curve. Thereby information about compliance/elastance is obtained.

Reference is now given to FIG. 9 that shows two different intracranial pressure recordings in one single case. Pressures were recorded simultaneously (with identical time reference) by means of one sensor placed within the brain parenchyma (FIGS. 9a-9b) and one sensor placed epidurally (FIGS. 9c-9d). An epidural placement means that the sensor is placed outside the dura mater actually mimicking non-invasive pressure monitoring since the sensor is not placed within the cavity in which pressure is measured. Both pressures measured within brain parenchyma and epidurally are relative to atmospheric pressure, and represent absolute pressures. For both pressure curves (FIGS. 9a and 9c) are presented the absolute pressures 17 on the y axis and the time scale 12 on the x axis. Both the x axes show identical time sequences, making a beat to beat comparison possible. It should be noted that the absolute pressures differ for the pressure curve 21 for parenchyma (FIG. 9a) and epidural (FIG. 9c) pressures. For FIG. 9a mean intracranial pressure for the whole recording period was 5.9 mmHg. For FIG. 9c mean intracranial pressure for the whole recording period was 8.35 mmHg. In this context, the absolute mean pressure values of 5.9 and 8.35 mmHg actually represent the mean of all 5 second time intervals during the total recording period. On the other hand, the distribution of single waves was nearly identical between parenchyma and epidural measurements, as indicated in the histogram located to the right for each pressure curve (FIGS. 9b and 9d). Whereas the pressure curves 21 show absolute pressures the histograms refer to single waves defined by relative pressures. The amplitudes of the single waves are computed as relative pressure differences. In FIGS. 9b and 9d is shown the histogram wherein all weighted values 40 of balanced positions of amplitude and latency during said recording period is shown on the x axis. On the y axis the percentage occurrence 39 is indicated, which is how often a single wave with a certain combination of latency/amplitude occurs in percentage of the total number of single waves during the recording period. Each balanced position of amplitude/latency combinations represented by a weight value is represented by one bar 41 in the histogram. For example, the label on the X-axis of 0.38|6.50 refers to single waves with a combination of latency of 0.38 seconds and amplitude of 6.50 mmHg. In this example the values 0.31|5.00, 0.38|6.50 and 0.14|8.50 refer to balanced position values. These values might as well be referred to as index values when a weighted matrix is used. The histograms presented in FIGS. 9b and 9d actually show weighted balanced position values 40 of all time sequences 11 during the recording period illustrated in FIGS. 9a and 9c. The bar corresponding to the latency|amplitude combination of 0.38|6.50 indicates the percentage by which single wave occurred as related to the total numbers of single waves. For parenchyma (FIG. 9b) and epidural (FIG. 9d) pressures, the single wave distribution is nearly identical. These pressure recordings illustrate several important aspects of the invention: Absolute pressures recorded by the conventional strategy and illustrated in the pressure curves give no reliable description of the pressures. Pressures within the brain parenchyma and the epidural space as revealed by the pressure curves were markedly different. Both the absolute pressures and the morphology of the curve were different. Continuous pressure recordings are most accurately described by the single wave distribution. The histogram presentations of the single wave distribution were nearly identical for pressure recordings within the brain parenchyma and the epidural space.

Therefore, single wave distribution may be equally presented whether or not the sensor is placed within the cavity pressure is measured. Results such as these gave the idea to compute single wave distribution in infants by monitoring fontanel pressure non-invasively by applying a sensor on the fontanel. When the results presented in FIGS. 9a-d are presented in a differential plot as described in FIGS. 6a-c, absolute mean pressure is compared time sequence for time sequence. Also balanced position of amplitude and latency is compared time sequence for time sequence, since both pressure curves have identical time reference. Such a differential plot of the results presented in FIGS. 9a-d showed a marked difference in absolute mean pressures between parenchymatous and epidural measurements. The differences in balanced positions of amplitude and latency between time sequences with identical reference were minimal.

Reference is now given to FIGS. 10a-d illustrating how matrix and histogram presentations change before and after intervention in one single case. With reference to the first recording period, is presented the pressure curve 21 (FIG. 10a) and histogram (FIG. 10b). The trend plot 21 (FIG. 10c) and histogram (FIG. 10d) for the second recording period also is presented. The matrix 36 corresponding to FIGS. 10a and 10b is shown in Table V, and the matrix 36 corresponding to FIGS. 10c and 10d in Table VI. An explanation of the different amplitude 4 and latency 5 groups presented in Tables V and VI are further given for Table I. The numbers 37 within cells of matrix 36 presented in Table I represent absolute numbers, whereas the numbers in Tables V and VI refer to percentages. Before intervention, the combination of amplitude 4 of 7.5 mmHg and latency 5 of 0.26 seconds occurred in 0.17% of the total numbers of single waves. After intervention, the combination of amplitude 4 of 7.5 mmHg and latency 5 of 0.26 seconds did not occur. In this particular example, the matrixes 36 including amplitudes 4 and latencies 5, were standardized to a recording period and a heart rate. Non-standardized numbers may as well be presented. The standardized recording period was set to one hour. The actual heart rate was variable during the recording period, but was standardized to a standardized heart rate of 70 beats a minute. With reference to histograms (FIGS. 10c, 10d), on the y axis is shown percentage of occurrence 39 that is how often a single wave with a certain latency/amplitude combination occurred in percentage of the total number of single waves. On the x axis is shown the different weighted latency/amplitude combinations 40. As an example; in these histograms the label 0.14|8.50 on the x axis refers to single waves with latency 5 of 0.14 seconds and amplitude 4 of 8.50 mmHg. Accordingly, the bar 41 corresponding to the label 0.14|8.50 shows the percentage of single waves with this combination occurring as percentage of total number of single waves during a standardized recording time of one hour and a standardized heart rate of 70 beats a minute. Before (FIGS. 10a, 10b) and after (FIGS. 10c, 10d) intervention, the matrixes (Tables V and VI) and histograms showed a marked difference in single wave distribution, with a change of the single wave distribution in a more normal direction.

FIG. 10 also may serve as an example of distribution of balanced positions of amplitude and latency combinations 39 for a whole recording period, wherein the total distribution is presented in matrixes in Tables V and VI. Thereby, balanced positions of amplitude/latency combinations within individual time sequences for the total recording period are presented as numbers in proportion 38 of the total number. In this situation, the bars 41 shown in the histogram refer to balanced positions of amplitude/latency combinations during selected time sequences 11. The histograms in FIGS. 10b and 10d illustrate how balanced position of amplitude and latency changes from one pressure recording to another. With reference to the matrix in Table V, balanced position of latency/amplitude combinations of 0.24 seconds|4 mmHg occurred in 5.02% in the matrix 36 presented in Table V, whereas this combination did not occur in matrix of Table VI. In this context, it should be noted that the matrixes 36 usually are computed each time sequence 11 with determination of balanced position of amplitude/latency combinations for each individual time sequence 11 in a series of continuous time sequences. The matrixes 36 presented in Tables V and VI, on the other hand, show the distribution of balanced positions of amplitude and latency combinations for the whole recording period.

TABLE V

Matrix of amplitude (dP) and latency (dT) combinations corresponding to continuous pressure recordings presented in FIGS. 10a and 10b.

| dT\dP | 1 | 1.5 | 2 | 2.5 | 3 | 3.5 | 4 | 4.5 | 5 | 5.5 | 6 | 6.5 | 7 |
|---|---|---|---|---|---|---|---|---|---|---|---|---|---|
| 0.1 | | 0.02 | 0.05 | 0.21 | 0.13 | | | | | | | | |
| 0.11 | | | | 0.09 | 0.05 | | | | | | | | |
| 0.12 | | | | | | | | | | | | | |
| 0.13 | | | 0.01 | 0.02 | 0.04 | | | | | | | | |
| 0.14 | | | | 0.01 | | | | | | | | | |
| 0.15 | | | | | | | | | | | | | |
| 0.16 | | | | | | | | | | | | | |
| 0.17 | | 0.03 | 0.34 | 0.05 | 0.02 | | | | | | | | |
| 0.18 | | 0.01 | 0.33 | 0.19 | 0.04 | | | | | | | | |
| 0.19 | | | | | | | | | | | | | |
| 0.2 | | 0.01 | 0.26 | 0.65 | 0.9 | 0.11 | | | | | | | |
| 0.21 | | | 0.14 | 0.71 | 1.51 | 0.58 | 0.21 | 0.12 | 0.02 | | | | |
| 0.22 | | | | | | | | | | | | | |
| 0.23 | | | 0.41 | 1.55 | 4.5 | 3.93 | 2.59 | 1.01 | 0.39 | 0.17 | 0.04 | 0.01 | 0.04 |

TABLE V-continued

Matrix of amplitude (dP) and latency (dT) combinations corresponding to continuous pressure recordings presented in FIGS. 10a and 10b.

| | | | | | | | | | | | |
|---|---|---|---|---|---|---|---|---|---|---|---|
| 0.24 | | 0.37 | 1.93 | 3.83 | 5.95 | 5.02 | 3.32 | 1.92 | 1.13 | 0.5 | 0.29 | 0.23 |
| 0.25 | | | | | | | | | | | | |
| 0.26 | | 0.18 | 1.78 | 4.22 | 7.59 | 9.75 | 7.05 | 3.36 | 1.95 | 1.03 | 0.52 | 0.23 |
| 0.27 | | 0.03 | 0.35 | 1.08 | 2.32 | 3.66 | 2.81 | 1.36 | 0.88 | 0.32 | 0.2 | 0.1 |
| 0.28 | | 0.04 | 0.03 | 0.06 | 0.26 | 0.4 | 0.47 | 0.3 | 0.2 | 0.06 | 0.03 | 0.04 |
| 0.29 | | 0.01 | 0.01 | | | | 0.01 | 0.01 | | | | |
| 0.3 | | | 0.01 | | | | | | | | | |
| 0.31 | | | | | | | | | | | | |
| 0.32 | | | 0.01 | 0.01 | | | | | | | | |
| 0.33 | | | | | | | | | | | | |
| 0.34 | | | 0.01 | | | | | | | | | |

| dT\dP | 7.5 | 8 | 8.5 | 9 | 9.5 | 10 | 10.5 | 11 |
|---|---|---|---|---|---|---|---|---|
| 0.1 | | | | | | | | |
| 0.11 | | | | | | | | |
| 0.12 | | | | | | | | |
| 0.13 | | | | | | | | |
| 0.14 | | | | | | | | |
| 0.15 | | | | | | | | |
| 0.16 | | | | | | | | |
| 0.17 | | | | | | | | |
| 0.18 | | | | | | | | |
| 0.19 | | | | | | | | |
| 0.2 | | | | | | | | |
| 0.21 | | | | | | | | |
| 0.22 | | | | | | | | |
| 0.23 | 0.03 | | | 0.03 | | | | |
| 0.24 | 0.13 | 0.18 | 0.13 | 0.06 | 0.01 | | | |
| 0.25 | | | | | | | | |
| 0.26 | 0.17 | 0.11 | 0.07 | 0.06 | 0.09 | 0.05 | 0.03 | 0.02 |
| 0.27 | 0.05 | 0.01 | | 0.02 | 0.01 | 0.01 | | |
| 0.28 | 0.01 | | | | | | | |
| 0.29 | | | | | | | | |
| 0.3 | | | | | | | | |
| 0.31 | | | | | | | | |
| 0.32 | | | | | | | | |
| 0.33 | | | | | | | | |
| 0.34 | | | | | | | | |

TABLE VI

Matrix of amplitude (dP) and latency (dT) combinations corresponding to continuous pressure recordings presented in FIGS. 10c and 10d.

| dT\dP | 1 | 1.5 | 2 | 2.5 | 3 | 3.5 | 4 | 4.5 | 5 | 5.5 | 6 | 6.5 | 7 | 7.5 | 8 | 8.5 | 9 | 9.5 | 10 | 10.5 | 11 |
|---|---|---|---|---|---|---|---|---|---|---|---|---|---|---|---|---|---|---|---|---|---|
| 0.1 | | 10.5 | 14.6 | 0.63 | | | | | | | | | | | | | | | | | |
| 0.11 | 0.02 | 2.04 | 2.75 | 0.07 | | | | | | | | | | | | | | | | | |
| 0.12 | | | | | | | | | | | | | | | | | | | | | |
| 0.13 | | 1.17 | 2.08 | 0.11 | | | | | | | | | | | | | | | | | |
| 0.14 | 0.01 | 1.17 | 2.72 | 0.23 | | | | | | | | | | | | | | | | | |
| 0.15 | | | | | | | | | | | | | | | | | | | | | |
| 0.16 | | 0.73 | 1.5 | 0.05 | | | | | | | | | | | | | | | | | |
| 0.17 | 0.02 | 6.74 | 11.8 | 0.3 | 0.03 | | | | | | | | | | | | | | | | |
| 0.18 | | 5.29 | 5.54 | 0.31 | | | | | | | | | | | | | | | | | |
| 0.19 | | | | | | | | | | | | | | | | | | | | | |
| 0.2 | 0.01 | 3.64 | 7.26 | 0.63 | 0.04 | | | | | | | | | | | | | | | | |
| 0.21 | | 0.82 | 2.17 | 0.34 | 0.03 | 0.01 | | | | | | | | | | | | | | | |
| 0.22 | | | | | | | | | | | | | | | | | | | | | |
| 0.23 | | 0.79 | 2.6 | 1.38 | 0.13 | 0.05 | | | | | | | | | | | | | | | |
| 0.24 | | 0.21 | 1 | 0.91 | 0.12 | 0.01 | | | | | | | | | | | | | | | |
| 0.25 | | | | | | | | | | | | | | | | | | | | | |
| 0.26 | | 0.11 | 0.73 | 1.42 | 0.36 | 0.06 | | | | | | | | | | | | | | | |
| 0.27 | | 0.04 | 0.54 | 0.91 | 0.28 | 0.07 | | | | | | | | | 0.01 | | | | | | |
| 0.28 | | | 0.34 | 0.61 | 0.39 | 0.05 | 0.01 | | 0.01 | | | | | | | | | | | | |
| 0.29 | | | 0.07 | 0.12 | 0.12 | 0.04 | | | 0.01 | | | | | | | | | | | | |
| 0.3 | | | 0.07 | 0.06 | 0.04 | 0.01 | | | | | | | | | | | | | | | |
| 0.31 | | | | | | | | | | | | | | | | | | | | | |
| 0.32 | | | 0.02 | 0.09 | 0.05 | 0.04 | | | | | | | | | | | | | | | |
| 0.33 | | | 0.02 | 0.05 | 0.1 | 0.03 | | | | | | | | | | | | | | | |
| 0.34 | | | | 0.07 | 0.18 | | | | | | | | | | | | | | | | |

TABLE VI-continued

Matrix of amplitude (dP) and latency (dT) combinations corresponding to continuous pressure recordings presented in FIGS. 10c and 10d.

| dT\dP | 1 | 1.5 | 2 | 2.5 | 3 | 3.5 | 4 | 4.5 | 5 | 5.5 | 6 | 6.5 | 7 | 7.5 | 8 | 8.5 | 9 | 9.5 | 10 | 10.5 | 11 |
|---|---|---|---|---|---|---|---|---|---|---|---|---|---|---|---|---|---|---|---|---|---|
| 0.35 |   |   |   | 0.02 | 0.13 |   |   |   |   |   |   |   |   |   |   |   |   |   |   |   |   |
| 0.36 |   |   |   | 0.02 | 0.12 |   |   |   |   |   |   |   |   |   |   |   |   |   |   |   |   |
| 0.37 |   |   |   |   | 0.02 |   |   |   |   |   |   |   |   |   |   |   |   |   |   |   |   |

Reference is now given to FIG. 11. Two continuous intracranial pressure curves 21 are shown in FIGS. 11a and 11c. On the y axis is the scale of absolute mean pressure 17 computed according to conventional technology (Method 1). The time scale 12 is on the x axis. The trend curve 21 presents a continuous plot of mean pressures wherein mean pressure is computed each time sequence (6 seconds duration in this case) in a continuous series of time sequences. Mean pressures 21 are much higher in FIG. 11a than in FIG. 11c. Below the absolute pressure curves 21 (FIGS. 11a and 11c) is shown the corresponding trend plot 42 of balanced position of amplitude and latency computed each 6 seconds. The two-dimensional balanced position has been computed as a one-dimensional value, as described for Table IV. By applying the equation (no. 7) used to weight the matrix 36 presented in Table IV, each balanced position of amplitude 4 and latency 5 was expressed as a weight value. The weighted value is given the term predicted mean pressure 40 shown on the y axis of FIGS. 11b and 11d. The time scales 12 are identical for FIGS. 11a and 11b, and for 11c and 11d. Thus, the trend plots 42 of weighted balanced positions (predicted mean pressure) show balanced position of amplitude 4 and latency 5 computed each time sequence 11 (6 seconds) that is expressed as a weighted values termed predicted mean pressure 40. Each plot in said trend plot 42 represents the balanced position each time sequence 11 in a continuous series of time sequences. The trend plots 42 of weighted balanced positions are similar for FIGS. 11b and 11d. Thus, though absolute mean pressure curves 21 differed markedly, weighted trend plots 42 of balanced position did not differ. The trend plots 42 of weighted balanced position in FIGS. 11b and 11d correspond to the trend plot 42 schematically presented in FIG. 5e. The histograms presented in FIGS. 9c, 9d, 10b, and 10d showing weighted balanced position 40 on the x axis correspond to the histogram presentation shown in FIG. 8d. In both the trend plots and histograms weighted values 40 of balanced position of amplitude 4 and latency 5 are presented. These are examples of presentations and are not intended to limit the scope of the invention.

Reference is now given to FIG. 12. The present invention uses the method for analysis of single pressure waves 1 to provide a strategy for more optimal single pressure wave detection, particularly when non-invasive devices are used for pressure monitoring. A schematic representation is provided in FIG. 12a. The invention may be used in conjunction with various types of sensors 46 providing signals indicative of pressure. The sensor device itself is not a part of the invention. It is well known from the prior art that sensors 46 operate together with pressure transducers 47. An excitation signal is applied from the transducer 47 to the sensor 46, and the sensor 46 gives back a new signal indicative of the pressure to the transducer 47. The transducer 47 then processes the signal to another signal that is more suitable for further signal processing. The sensor device may as well incorporate a sensor-regulating device 48 that regulates how tile sensor 46 is applied to the object wherein pressure is measured. In general terms, the sensor device consists of a sensor 46, transducer 47 and sensor-regulating device 48. The pressure signals from the pressure transducer 47 are further converted into pressure-related digital data with a time reference, and analysed according to the invention within the processing unit 49. The method for analysis of single pressure waves provides an output that gives a first control signal 50 to a regulator device 52. Said regulator device may be a transducer that converts the first control signal 50 from the processing unit 49 into another second control signal 51. The second control signal 51 produced by the regulator 52 modifies the performance of the sensor-regulating device 48. The sensor-regulating device modifies the mode by which the sensor/transducer is able to sample signals indicative of pressure. Thereby, the inventive method for analysis of single pressure waves is used to control and modify the sampling mode of signals derivable from a pressure sensor device.

Though the sensor device itself is not a part of the invention, nor a method by which such a sensor device is used on an animal or human body cavity, some examples are given to illustrate the concept, though this represents no limitation of the scope of the invention. First, applanation tonometry are widely used for non-invasive pressure measurement. Pressure gradients exist across the walls of a pressurised elastic sphere. When a pressure sensor is applied to the surface of the flattened area, no pressure gradient exists over the flattened portion. Pressure measurements can be made when a constant pressure is applied to the flattened area. Applanation tonometry may for example be used in non-invasive blood pressure monitoring, monitoring of ocular pressure (i.e. pressure within the ocular bulb), and even monitoring fontanel pressure in infants with an open fontanel. The pressure sensor 46 consists of the pressure element that is in contact with the skill or eye bulb. Signals from the sensor 46 are converted within the pressure transducer 47. When pressures are measured using the principles of applanation tonometry, it is well known that the pressure pulsation's detected by the tonometer depend on the pressure by which the tonometer is applied to the measurement surface. With increasing pressure from the tonometer, pressure waves increase until the waves with highest amplitudes are recorded. The pressure by which the applanation tonometry is applied to the surface determines quality of signal detection. Therefore, devices for applanation tonometry may include a sensor-regulating device 48, which controls the pressure by which the tonometer is applied to the surface. Such a sensor-regulating device 48 may be an inflatable balloon housed in a solid frame, under control of a pneumatic system. Such a sensor-regulating device 48 provides the opportunity for controlled inflation of air into an air chamber of the sensor. The pneumatic system is automatic and controlled by a processing unit 49, in the way that the air chamber pressure is automatically regulated to show the best single pressure waves. Other sensors 46 apply Doppler signals to detect pressure related signals. The signal detected by the Doppler may be modified within the transducer 47. In such a system the sensor-regulating device 48 incorporates a system wherein Doppler signals are applied to/receive from the object, including acquisitions of direction of signal emission as well as the signal quantity and quality. The emission and detection of Doppler signals heavily depend on the angulations of the signal emitting source. In this situation the sensor-regulating device 48 determines how Doppler signal are applied to the object, including acquisitions of signal direction and strength. When the sensor 46 and transducer 47 use acoustic signals the sensor-regulating device 48 may as well control signal direction and signal quantity and quality. Since the sensor device itself is not a particular feature of the invention, a more detailed description is not given.

The procedure for controlling and changing the sampling mode of signals derivable from a pressure sensor device is further illustrated in FIGS. 12b and 12c. The digital signals are sampled and analysed during short time sequences 11 (e.g. of 3 seconds duration) in a continuous series of short time sequences 11. Said analysis of single wave 1 related parameters within said time sequences 11 is performed by a processing unit 49. For each time sequence 11 a number of single pressure wave 1 related parameters are computed, as already described in more detail. One or more of the following parameters are included:

(1) absolute mean pressure for each identified single pressure wave 1 [wavelength 7 ($P_{min}$-$P_{min}$)] within said time sequence 11;
(2) mean of mean pressure for all identified single pressure waves 1 [wavelength 7 ($P_{min}$-$P_{min}$)] within said time sequence 11;
(3) standard deviation of absolute mean pressure for all identified single pressure waves 1 [wavelength 7 ($P_{min}$-$P_{min}$)] within said time sequence 11;
(4) numbers of single pressure waves 1 during said time sequence 11;
(5) single pressure wave derived heart rate 16 during said time sequence 11;
(6) relative pressure amplitude ($\Delta P$) 4 value for each identified single pressure wave 1 [wavelength 7 ($P_{min}$-$P_{min}$)] within said time sequence 11;
(7) standard deviation of relative pressure amplitude ($\Delta P$) 4 values for all identified single pressure waves 1 [wavelength 7 ($P_{min}$-$P_{min}$)] within said time sequence 11;
(8) relative latency ($\Delta T$) 5 value for each identified single pressure wave 1 [wavelength 7 ($P_{min}$-$P_{min}$)] within said time sequence 11;
(9) standard deviation of relative latency ($\Delta T$) 5 values for all identified single pressure waves 1 [wavelength 7 ($_{min}$-$P_{min}$)] within said time sequence 11;
(10) rise time ($\Delta P/\Delta T$) coefficient 6 for each identified single pressure wave 1 [wavelength 7 ($P_{min}$-$P_{min}$)] within said time sequence 11;
(11) standard deviation of rise time ($\Delta P/\Delta T$) coefficient 6 for all identified single pressure waves 1 [wavelength 7 ($P_{min}$-$P_{min}$)] within said time sequence 11;
(12) relative latency ($\Delta T$) 5 value for each identified single pressure wave 1 [wavelength 7 ($_{min}$-$P_{min}$)] within said time sequence 11;
(13) balanced position within said first matrix 36 for combinations of single pressure wave amplitude ($\Delta P$) 4 and latency ($\Delta T$) 5 values within said time sequence 11; and
(14) balanced position within said second matrix 36 for combinations of single pressure wave rise-time ($\Delta P/\Delta T$) 6 coefficients within said time sequence 11.

FIG. 12b illustrates seven time sequences 11 ($1^{st}$, $2^{nd}$, $3^{rd}$, $4^{th}$, $5^{th}$, $6^{th}$, and $7^{th}$) where single pressure wave 1 detection is modified. Single pressure wave 1 detection is most optimal during the $3^{rd}$ and $4^{th}$ time sequences wherein the amplitudes 4 are most evident. For each time sequence 11 said analysis procedure is applied to all single pressure waves 1. Selected criteria are applied to the analysis output and would reveal most optimal single wave detection for the $3^{rd}$ and $4^{th}$ time sequences 11 in this example.

The output of said analysis within the processing unit 49 establishes or amends a first control signal 50 that is applied to a regulator 52. The mode of the first control signal 50 is determined by the output of said single pressure wave related analysis. Between each new time sequence, a first control signal 50 may be determined, depending on criteria applied to the analysis results. The first control signal 50 is converted within a regulator 52. The regulator 52 may be considered as a transducer converting the first control signal 50 into another second control signal 51. The regulator 52 deliverable second control signal 51 may depend on the type of sensor-regulating device 48 incorporated in the sensor device. Therefore, the deliverable second control signal 51 may modify a sensor-regulating device: 48 in a wide sense. An example is given with reference to applanation tonometry wherein a pneumatic system controls the pressure by which the sensor 46 is applied to the surface. The second control signal 51 delivered from the regulator 52 may determine the pressure level within the pneumatic system, which determines the pressure by which the tonometer is applied to the surface. This example is further illustrated in FIG. 12c. In this situation, the control signal level 53 determines the pressure level within a pneumatic system.

The pressure level 54 is increased for each new of the first three time sequence 11 ($1^{st}$, $2^{nd}$, and $3^{rd}$ time sequence). As indicated in FIG. 12b, single pressure wave 1 detection is improved for each new of said time sequences 11. The control signal level 53 and accordingly the pressure level 54 is kept constant between the $3^{rd}$ and $4^{th}$ time sequences 11 (FIG. 12c) wherein single waves 1 remain more or less unchanged. The control signal level 53 and accompanying pressure level 54 is reduced during the subsequent $5^{th}$, $6^{th}$, and $7^{th}$ time sequences 11, wherein also single wave 1 detection is reduced. The second control signal 51 produced by the regulator 52 may as well control a sensor regulating device 48 using Doppler signals. In this situation the second control signal 51 may control the angulations and signal quality and quantity of the sensor-regulating device 48 using Doppler signals. Furthermore, when a sensor device utilizes acoustic signals, the second control signal 51 may control the sensor regulating device 48 determining the quality and quantity of acoustic signals applied to the surface wherein pressures are measured.

The results of said single pressure wave 1 analysis are compared for different time sequences 11. Changes in a first control signal 50 and subsequent in another second control signal 51 both produce modifications of the sensor-regulating device 48. The deliverable control signals corresponding to analysis output Wherein single pressure wave parameters meet one or more selectable criteria would be used during subsequent pressure monitoring. The selectable criteria correspond to the control signal wherein the most optimum single pressure wave detection is obtained.

It is not within the scope of the invention to limit the strategy by which the process is performed. The system provides feedback interaction between the processing unit 49 performing said analysis, the deliverable first control signal 50 to the regulator 52 controlling and changing the deliverable second control signal 51 applied to the sensor-regulating device 48. It is described one example of the interactive operation of the regulator 52 and processing unit 49 related to the description shown in FIGS. 12b and 12c, though this represents no limitation of the scope of the invention. During a given time period of for example 30 seconds, the regulator 52 delivers a total of ten different second control signals 51, each separated by 3 seconds. During the period of 30 minutes, ten modifications of the sensor-regulating device 48 are made between each of said 3 second intervals. During the ten time sequences 11 (each lasting 3 seconds), single pressure waves are analyzed within the processing unit 49. For each of said time sequences 11 the output of the analysis within the processing unit 49 determines a first control signal 50 that corresponds to the second control signal 51 from the regulator 52. Accordingly, each time sequence 11 corresponds to a second control signal 51 from said regulator 52 that corresponds to an output of single pressure wave 1 analysis within said processing unit 49 that further corresponds to a first control signal 50 to the regulator 52. These corresponding values are determined for each individual of the ten time sequences 11 during said recording period of 30 minutes. During the subsequent pressure monitoring, the processing unit 49 provides the first control signal 50 that corresponds to optimum single pressure wave 1 detection. This first control signal 50 from the processing unit 49 to the regulator 52 gives another second control signal 51 to the sensor-regulating device 48, further enabling the sensor-regulating device 48 for optimum single pressure wave 1 detection. The procedure of determining the most optimum control signal (here exemplified as lasting 30 minutes) may be reiterated at selected intervals during an ongoing pressure measurement. Various modifications of this process are possible. For example, during an ongoing pressure monitoring the processing unit 49 may automatically determine the second control signal 51 from the regulator 48, wherein single pressure wave 1 detection is most optimum.

The invention claimed is:

1. A method for analyzing pressure-signals derivable from pressure measurements on or in a body of a human being or animal, comprising the steps of sampling said signals at specific intervals, and converting the pressure-signals into pressure related digital data with a time reference,
wherein for selectable time sequences the method comprises the further steps of:
a) identifying from said digital data the single pressure waves in said pressure-signals,
b) computing single pressure wave related parameters of said single pressure waves, selected from:
amplitude,
latency, and
rise time coefficient,
c) identifying numbers of single pressure waves with pre-selected parameter values of such waves with respect to said parameters such as amplitude, latency and rise time coefficient,
d) performing a plotting operation based on at least one of:
d1) plotting the numbers of occurrences of single pressure waves with pre-selected values of amplitude and latency in a first matrix, determining balanced position of amplitude and latency combinations in said first matrix, and presenting the balanced positions obtained as numerical values or as related to weighted values, and
d2) plotting the numbers of occurrences of single pressure waves with pre-selected values of rise time coefficients in a second matrix, determining balanced positions of rise time coefficients in said second matrix, and presenting the balanced positions obtained as numerical values or as related to weighted values.

2. A method according to claim 1, wherein said method is applied to continuous pressure-signals during said selectable time sequences.

3. A method according to claim 2, wherein said selectable time sequences lies in the range 5 -15 seconds.

4. A method according to claim 2 or 3, wherein single pressure waves occurring between two time sequences are included in one or the other of said two time sequences according to pre-selected criteria.

5. A method according to claim 2, wherein a continuous series of said selectable time sequences constitutes a continuous pressure recording period.

6. A method according to claim 5, wherein any of said selectable time sequences are accepted or rejected for further analysis according to selected criteria.

7. A method according to claim 1, comprising the further steps of applying the method to all continuous pressure-signals for each of said time sequences in a continuous series of said time sequences during a continuous measurement period.

8. A method according to claim 1, wherein said identifying step includes determination of all minimum (valleys) and maximum (peak) pressure values in said signal.

9. A method according to claim 1, wherein said identifying step of single pressure waves relates to identifying a minimum pressure value ($P_{min}$) related to a diastolic minimum value and a maximum pressure value ($P_{max}$) related to a systolic maximum value of said single pressure wave.

10. A method according to claim 9, wherein said systolic maximum pressure value ($P_{max}$) is one of three peak values occurring in said single pressure wave.

11. A method according to claim 10, wherein
a first (P1) of said three peak values in said single pressure wave has an amplitude related to the top of the percussion wave,
a second (P2) of said three peak values has an amplitude related to a tidal wave portion of said single pressure wave, and
a third (P3) of said three peak values has an amplitude related a dichrotic wave portion of said single pressure wave.

12. A method according to claim 10 or 11 further comprising the step of calculating one or more rise time coefficients $\Delta P/\Delta T$ based on a ratio between said amplitude and latency values.

13. A method according to claim 1, wherein said identifying step of single pressure waves includes determination of a minimum-maximum ($P_{min}/P_{max}$) pair of said single pressure wave.

14. A method according to claim 1, wherein said identifying step includes determining at least one of the single pressure wave parameters related to correct minimum-maximum pressure ($P_{min}/P_{max}$) pairs, said parameters selected from the group of: amplitude ($\Delta P$), latency ($\Delta T$), and rise time coefficient ($\Delta P/\Delta T$).

15. A method according to claim 1, wherein said single pressure wave amplitude relates to pressure amplitude=$\Delta P$=systolic maximum value ($P_{max}$)–diastolic minimum value ($P_{min}$).

16. A method according to claim 1, wherein said single pressure wave latency relates to time latency =$\Delta T$=time sequence wherein pressures increases from diastolic minimum pressure ($P_{min}$) to systolic maximum pressure ($P_{max}$).

17. A method according to claim 1, wherein said single pressure rise time coefficient relates to the relationship $\Delta P/\Delta T$ between amplitude $\Delta P$ and latency $\Delta T$.

18. A method according to claim 1, wherein said identifying step includes exclusion of minimum-maximum pressure ($P_{min}/P_{max}$) pairs with either amplitude ($\Delta P$), latency ($\Delta T$) or rise time coefficient ($\Delta P/\Delta T$) values outside pre-selected thresholds.

19. A method according to claim 1, wherein said single pressure wave parameters elected from the group of: amplitude ($\Delta P$), latency ($\Delta T$) and rise time coefficients ($\Delta P/\Delta T$) are relative values only and independent of any zero pressure level.

20. A method according to claim 1, wherein step b further includes a parameter of absolute mean pressure and step c includes a parameter of absolute mean pressure, and wherein absolute mean pressure for each individual of said single pressure waves relates to mean pressure during the time of the pressure waveform, i.e. from diastolic minimum pressure ($P_{min}$) to diastolic minimum pressure ($P_{min}$).

21. A method according to claim 20, wherein mean pressure for an individual single pressure wave is the sum of pressure levels within said pressure wave divided by numbers of pressure samples.

22. A method according to claim 20, wherein mean pressure for an individual single pressure wave is the area under a curve (AUC) for said single pressure wave.

23. A method according to claim 1, wherein step b further includes a parameter of absolute mean pressure and step c includes a parameter of absolute mean pressure, and wherein absolute mean pressure for a selectable time sequence is the sum of absolute mean pressure (wavelength $P_{min}$-$P_{min}$) for all individual single pressure waves during said time sequence divided by the numbers of single pressure waves within said identical time sequence.

24. A method according to claim 1, wherein step b further includes parameter of absolute mean pressure and step c includes a parameter of absolute mean pressure, and wherein absolute mean pressure of single pressure waves relates to absolute pressure relative to atmospheric pressure.

25. A method according to claim 1, wherein single pressure waves are rejected when absolute pressure values of single pressure wave diastolic minimum pressure ($P_{min}$) and systolic maximum pressure ($P_{max}$) of said single waves are outside selected threshold values.

26. A method according to claim 1, wherein heart rate during said time sequence is equal to numbers of single pressure waves during a time sequence divided by the duration of said time sequence.

27. A method according to claim 1, wherein heart rate during said time sequence is equal to numbers of single pressure waves during a time sequence divided by the sum of wavelengths ($P_{min}$-$P_{min}$) for all of said individual single pressure waves during said time sequence.

28. A method according to claim 1 wherein a time sequence of pressure recordings is accepted or rejected according to single pressure wave related parameters within said time sequence.

29. A method according to claim 28, wherein said time sequence is of a duration in the range 5 -15 seconds.

30. A method according to claim 28, wherein a time sequence is rejected when standard deviation of absolute pressures of minimumlmaximum ($P_{min}/P_{max}$) pair values of said single pressure waves is outside selected threshold values.

31. A method according to claim 28, wherein a time sequence is rejected when standard deviation of one or more of single pressure wave parameters selected from the group of: amplitude ($\Delta P$), latency ($\Delta T$) and rise time coefficient ($\Delta P/\Delta T$) is outside selected threshold values.

32. A method according to claim 28, wherein a time sequence is rejected when the number of single pressure waves within said time sequence is outside a selected threshold value.

33. A method according to claim 28, wherein a time sequence is rejected when single pressure wave derived heart rate for said time sequence is outside a selected threshold value.

34. A method according to claim 28, wherein a time sequence is rejected when the number of single pressure waves for said time sequence deviates outside selected values, as compared to the number of single pressure waves derived from another pressure recorded during identical time sequence with identical time reference.

35. A method according to claim 28, wherein a time sequence is rejected when single pressure wave derived heart rate for said time sequence deviates outside selected values, as compared to single pressure wave derived heart rate from another pressure recorded during identical time sequence with identical time reference.

36. A method according to claim 28, wherein a time sequence is rejected when single pressure wave derived heart rate for said time sequence deviates outside selected values, as compared to heart rate derived from other source.

37. A method according to claim 36, wherein said other source is pulse oxymetry or electrocardiography.

38. A method according to anyone of claims 28-37, wherein said rejection or acceptance of time sequences is performed repeatedly during ongoing pressure measurements.

39. A method according to anyone of claims 28-37, wherein a log is made for accepted and rejected time sequences during a recording period.

40. A method according to claim 1, comprising the further step of creating at least one of said first and second matrices based on determination of a number of single pressure waves with pre-selected values related to one or more single pressure wave related parameters, and indicating for each matrix cell at respective intersections in at least one of said first and second matrices the number of occurrence of matches between specific parameters of said single pressure waves.

41. A method according to claim 40, wherein said first matrix is created based on determining numbers of single pressure waves with pre-selected values related to amplitude ($\Delta P$) and latency ($\Delta T$), wherein one axis of said first matrix is related to an array of pre-selected values of pressure amplitude ($\Delta P$), wherein the other axis in said first matrix is related to an array of pre-selected latencies ($\Delta T$), and wherein indicating for each matrix cell at respective intersections in said first matrix a number of occurrence of matches between a specific pressure amplitude ($\Delta P$) and a specific latency ($\Delta T$) related to successive measurements of single pressure waves over said time sequence.

42. A method according to claim 40, wherein said second matrix is created based on determining numbers of single pressure waves with pre-selected values related to rise time coefficient ($\Delta P/\Delta T$), wherein one axis of said second matrix is related to an array of pre-selected values of rise time coefficient ($\Delta P/\Delta T$), and wherein each cell in said second matrix there is indicated occurrence of pre-selected rise time coefficients ($\Delta P/\Delta T$) related to successive measurements of single pressure waves over said time sequence.

43. A method according to claim 40, wherein the single pressure wave parameters are categorized into groups, said groups reflecting ranges of said single wave parameter values.

44. A method according to anyone of claims 40-43, wherein reiterated updating of said at least one of said first and second matrices is made during said time sequence and during ongoing measurements taken within a measurement period.

45. A method according to claim 44, wherein said reiterated updating occurs in a time range of every 5-15 seconds.

46. A method according to claim 40, wherein said at least one of said first and second matrices are computed for each consecutive time sequence in a series of repeated time sequences.

47. A method according to claim 40, wherein the occurrence of matches in said at least of said first and second matrices is indicated through actual number or standardisation based number of matches during the specific measurement period.

48. A method according to claim 47, wherein said standardisation is related to wavelength of a single pressure wave (heart rate).

49. A method according to claim 40, wherein the occurrence of matches is indicated through percentage of matches during the specific measurement period.

50. A method according to claim 40, wherein said standardisation of said numbers or percentages of occurrence of matches is a function of the length of the specific measurement period.

51. A method according to claim 1, comprising the further step of computing balanced position for a number of occurrences of said single pressure wave amplitude ($\Delta P$) and latency ($\Delta T$) values in said first matrix.

52. A method according to claim 51, wherein balanced position of said first matrix of numbers of amplitude ($\Delta P$) and latency ($\Delta T$) combinations relates to mean frequency distribution of amplitude ($\Delta P$) and latency ($\Delta T$) combinations during said time sequence.

53. A method according to claim 51, wherein reiterated computation of said matrix balanced position within said time sequence is made during ongoing measurements taken over a measurement period.

54. A method according to claim 53, wherein said reiterated updating is made in a time range of every 5-15 seconds.

55. A method according to claim 53, further wherein reiterated updates of balanced positions of amplitude and latency values correspond to reiterated updates of a weighted number of said balanced positions, and wherein the weighted values are the mean pressure values termed predicted mean pressure values.

56. A method according to claim 53, further wherein reiterated updates of balanced positions of amplitude and latency combinations as weighted numbers are made against time, said balanced position being plotted as weight value number against time in a trend plot during ongoing pressure measurements.

57. A method according to claim 53, further wherein reiterated updates of balanced positions of amplitude and latency combinations as weight numbers during said time sequence are presented as weighted values and presented in a histogram.

58. A method according to claim 51, wherein a new matrix balanced position is computed for each time sequence in a consecutive series of said time sequences during ongoing measurements taken over a measurement period.

59. A method according to claim 51, wherein balanced position of numbers of occurrences in said first or second matrix is presented as numerical values or as weighted values.

60. A method according to claim 1, wherein balanced position is computed for number of occurrences of said single pressure wave rise time coefficient ($\Delta P/\Delta T$) values in said second matrix.

61. A method according to claim 60, wherein said balanced position of said second matrix numbers of rise time coefficient ($\Delta P/\Delta T$) relates to mean frequency distribution of rise time coefficients ($\Delta P/\Delta T$) during said selected time sequence.

62. A method according to claim 1, wherein step b further includes a parameter of absolute mean pressure and step c includes a parameter of absolute mean pressure, and wherein the method further comprising the steps of:

storing said single pressure wave related digital data in a database, relating said set of digital data to a given time sequence, relating said set of digital data to individual time sequences in a continuous series of said time sequences.

63. A method according to claim 62, wherein said single pressure wave related digital data stored in said database include at least one of the following feature items:

a) absolute pressure values for diastolic minimum pressure ($P_{min}$) value of each accepted $P_{min}/P_{max}$ pair within said time sequence, b) absolute pressure values for systolic maximum pressure ($P_{max}$) value of each accepted $P_{min}/P_{max}$ pair within said time sequence, c) absolute mean pressure for each individual single pressure wave, that is mean pressure from $P_{min}$ to $P_{max}$ (wavelength) of each individual single pressure wave within said time sequence, d) relative amplitude ($\Delta P$) pressure value for each individual single pressure wave within said time sequence, e) relative latency ($\Delta T$) value for each individual single pressure wave within said time sequence, f) relative rise time coefficient ($\Delta P/\Delta T$) for each individual single pressure; wave within said time sequence, g) number of single pressure waves within said time sequence, h) single pressure wave derived heart rate, computed as number of single pressure waves divided by the total duration of wavelengths ($P_{min}$ to $P_{min}$) of single pressure waves within said time sequence, i) single pressure wave derived heart rate, computed as number of single pressure waves divided by the duration of said time sequence wherein said single pressure waves occur, j) mean of absolute mean pressure value for all individual single pressure waves (wavelength $P_{min}$-$P_{min}$) occurring within said time sequence, computed as the sum of absolute mean pressure (wavelength $P_{min}$-$P_{min}$) for all individual single waves during said time sequence, divided by numbers of single pressure waves within said time sequence, k) standard deviation for absolute mean pressure values of all individual single pressure waves within said time sequence, l) standard deviation for diastolic minimum pressure ($P_{min}$) values of all individual single waves within said time sequence, m) standard deviation for systolic maximum pressure ($P_{max}$) values of all individual single waves within said time sequence, n) standard deviation for pressure amplitude ($\Delta P$) values for all individual single pressure waves within said time sequence,
o) standard deviation for relative latency ($\Delta T$) values of all individual single pressure waves within said time sequence,
p) standard deviation for relative rise time coefficient ($\Delta P/\Delta T$) values of all individual single pressure waves within said time sequence,
q) balanced position of amplitude ($\Delta P$)/latency ($\Delta T$) combinations within said first matrix of combinations of single pressure wave amplitude ($\Delta P$) and latency ($\Delta T$) values within said time sequence, and
r) balanced position of rise-time coefficients ($\Delta P/\Delta T$) within said second matrix of single pressure wave rise-time coefficients ($\Delta P/\Delta T$) within said time sequence.

64. A method according to claim 63, wherein said time sequence is in the range of 5-15 seconds.

65. A method according to claim 63, wherein the method further comprises the steps of:
storing said single pressure wave related digital pressure data on a computer readable medium, and
providing graphical presentations and statistical analysis of differences or relationships within or between any of said single pressure wave related digital pressure data.

66. A method according to claim 65, wherein said statistical analysis includes plotting of single wave parameters in scatter plots wherein each axis refers to one or said single pressure wave parameters.

67. A method according to claim 62, wherein differences or relationships between any of the single pressure wave related digital pressure data stored in said database are analyzed statistically.

68. A method according to claim 67, wherein a best fitted curve or equation is established for any relationships of said single pressure wave related parameters.

69. A method according to claim 68, wherein the best fitted curve or equation relates to ranges for said single pressure wave related parameters.

70. A method according to claim 69, wherein said individual pressure measurements are included in determining said total best fitted curve or equation according to selectable criteria, said selectable criteria related to distribution of single pressure wave related parameters within said individual pressure measurement.

71. A method according to claim 62, wherein said statistical analysis includes plotting of differences of values of said single wave parameters between different pressures with identical time sequence and identical time reference.

72. A method according to claim 71, wherein said differences relate to differences of absolute mean pressure between different pressures with identical time sequences and identical time reference.

73. A method according to claim 71, wherein said differences relate to differences of balanced position of amplitude ($\Delta P$) between different pressures with identical time sequences and identical time reference.

74. A method according to claim 71, wherein said differences relate to differences of balanced position of latency ($\Delta T$) between different pressures with identical time sequences and identical time reference.

75. A method according to claim 71, wherein said differences relate to differences of rise time coefficients between different pressures with identical time sequences and identical time reference.

76. A method according to claim 62, wherein absolute mean pressure during said time sequence is related to balanced position of amplitude ($\Delta P$) during said identical time sequence.

77. A method according to claim 62, wherein absolute mean pressure during said time sequence is related to balanced position of latency ($\Delta T$) during said identical time sequence.

78. A method according to claim 62, wherein balanced position of amplitude ($\Delta P$) during said time sequence is related to balanced position of latency ($\Delta T$) during said identical time sequence.

79. A method according to claim 1, wherein mean pressure for an individual time sequence is determined as a function of balanced position of amplitude and latency within said identical time sequence.

80. A method according to anyone of claims 1, and 62 and 63, wherein step b further includes a parameter of absolute mean pressure and step c includes a parameter of absolute mean pressure, and wherein the method further comprising the steps of giving weights to the cells of at least one of said first and second matrices of single pressure wave related parameters, said weights determined by relationships between said single pressure wave related parameters.

81. A method according to claim 80, wherein the method further comprises the steps of:
creating at least one or said first and second matrices based on single pressure wave related digital data, indicating at each cell at respective intersections in said at least one or said first and second matrices number of occurrence of matches between specific parameters of said single pressure waves, weighting each cell in said at least one or said first and second matrices to give a weighted value, said weighting comprising the steps of:
computing for individual pressure recordings relationships between single pressure wave parameters including the single pressure wave parameters represented in said at least one or said first and second matrices,
computing for a plurality of individual pressure recordings relationships between single pressure wave parameters including the single wave parameters represented in said at least one or said first and second matrices,
computing an equation in which the weighted value is a function of the single wave parameters included in said at least one or said first and second matrices,
providing each cell in said at least one or said first and second matrices with a weighted value according to said equation, the input values in said equation being the column and row group midpoints of said at least one or said first and second matrices, and
presenting any occurrence of matches between specific parameters of said single pressure waves within a particular matrix cell as the weighted value of said matrix cell.

82. A method according to claim 81, comprising the further steps of:
creating said first matrix based on determining number of single pressure waves with pre-selected values related to amplitude ($\Delta P$) and latency ($\Delta T$), one axis of said first matrix, being related to an array of pre-selected values of pressure amplitude ($\Delta P$), and the other axis being related to an array of pre-selected latencies ($\Delta T$),
indicating at each cell at respective intersections in said first matrix number of occurrence of matches between specific combinations of single pressure wave amplitude ($\Delta P$) and latency ($\Delta T$) related to successive measurements of single pressure waves within a time sequence, and weighting each cell in said first matrix to provide a weighted value related to mean pressure during said time sequence, said weighting of the matrix cells comprising the steps of:
computing for individual pressure recordings or a plurality of individual pressure recordings the best fitted equation for a relationship between absolute mean pressure and balanced position of single pressure wave amplitude ($\Delta P$) within said time sequences, computing for individual pressure recordings or a plurality of individual pressure recordings the best fitted equation for a relationship between balanced position of single pressure wave amplitude ($\Delta P$) and balanced position of single pressure wave latency ($\Delta T$) within said time sequences, computing for individual pressure recordings or a plurality of individual pressure recordings the best fitted equation for the relationship between absolute mean pressure, and balanced position of single pressure wave amplitude ($\Delta P$) and balanced position of single pressure wave latency ($\Delta T$) within said time sequences, computing for individual pressure recordings or a plurality of individual pressure recordings an equation for the relationship between absolute mean pressure as a function of balanced position of single pressure wave amplitude ($\Delta P$) and balanced position of single pressure wave latency ($\Delta T$) within said time sequences, computing for each cell in said matrix a mean pressure value derivable from the equation in which mean pressure is a function of balanced position of single pressure wave amplitude ($\Delta P$) and balanced position of single pressure wave latency ($\Delta T$) within said time sequences, said amplitude ($\Delta P$) and latency ($\Delta T$) values put into the equation being made according to selected criteria, such as the midpoint of the amplitude ($\Delta P$) and latency ($\Delta T$) group values, and
reiterating the step of determining weighted scale values for all cells within said first matrix.

83. A method according to claim 82, wherein said criteria is midpoint of the amplitude ($\Delta P$) and latency ($\Delta T$) group values.

84. A method according to claim 81, wherein matrix cells are given a value represented as a function of parameters of the matrix columns and rows.

85. A method according to claim 81, wherein all matrix cells of an amplitude ($\Delta P$)/latency ($\Delta T$) matrix being said first matrix are represented by mean pressure values, said mean pressure values being a function of balanced positions of amplitude ($\Delta P$) and latency ($\Delta T$) values, said mean pressure values termed predicted mean pressure.

86. A method according to claim 81, wherein matrix cells of an amplitude ($\Delta P$)/latency ($\Delta T$) matrix being said first matrix are represented by selected colors corresponding to the mean pressure values of said first matrix cells.

87. A method according to claim 81, wherein the two-dimensional balanced position of amplitude ($\Delta P$) and latency ($\Delta T$) within a given time sequence is represented by a one-dimensional weight value.

88. A method according to claim 1, wherein a best fitted curve or equation is made on the basis of individual pressure measurements, said individual pressure measurements being built up of a continuous series of said time sequences.

89. A method according to claim 1, wherein a total best fitted curve or equation is made on the basis of two or more of said individual pressure measurements.

90. A method according to claim 88 or 89, wherein a mean type of best fitted curve or equations is made from two or more of said individual pressure measurements.

91. A method according to claim 1, wherein best fitted equations for different single pressure wave parameter relationships are combined.

92. A method according to claim 91, wherein one single pressure wave related parameter is determined as a function of two or more other single pressure wave related parameters.

93. A method according to claim 1, wherein said analysis of pressure-signals is related to human or animal body pressure elected from one or more of: intracranial pressure, arterial blood pressure, cerebrospinal fluid pressure, cerebral perfusion pressure, ocular pressure, gastrointestinal pressure, urinary tract pressure, or any type of soft tissue pressure.

* * * * *

UNITED STATES PATENT AND TRADEMARK OFFICE
CERTIFICATE OF CORRECTION

PATENT NO. : 7,559,898 B2
APPLICATION NO. : 10/613112
DATED : July 14, 2009
INVENTOR(S) : Per Kristian Eide It is certified that error appears in the above-identified patent and that said Letters Patent is hereby corrected as shown below:

In the Drawings:

Sheet 4 of 12, Fig. 4b should appear as follows:

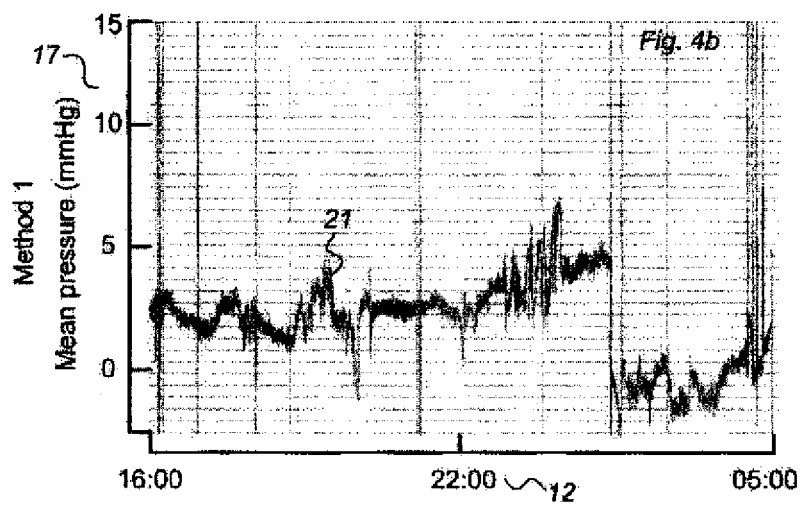

Signed and Sealed this
Eleventh Day of September, 2012

David J. Kappos
*Director of the United States Patent and Trademark Office*

CERTIFICATE OF CORRECTION (continued)
U.S. Pat. No. 7,559,898 B2

In the Drawings:

Sheet 6 of 12, Fig. 6a should appear as follows:

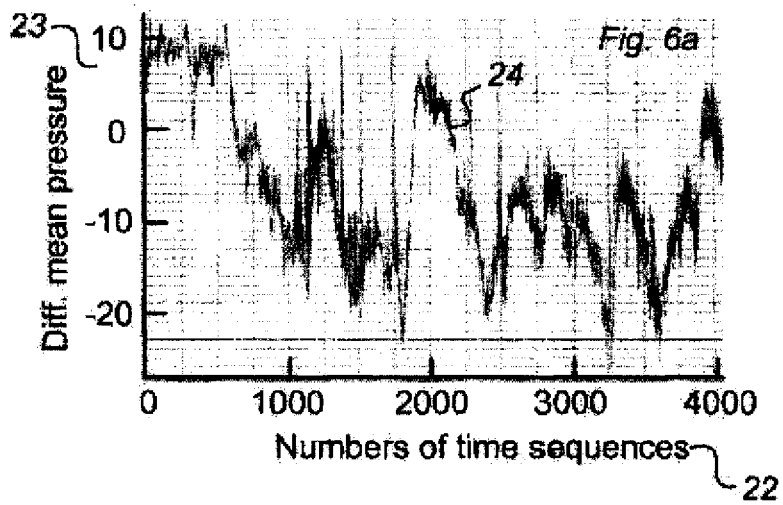

Sheet 6 of 12, Fig. 6b should appear as follows:

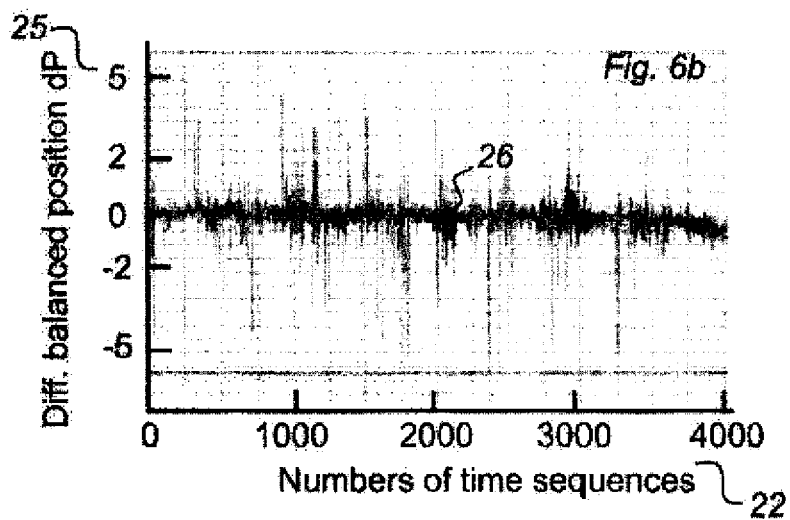

CERTIFICATE OF CORRECTION (continued)
U.S. Pat. No. 7,559,898 B2

In the Drawings:

Sheet 6 of 12, Fig. 6c should appear as follows:

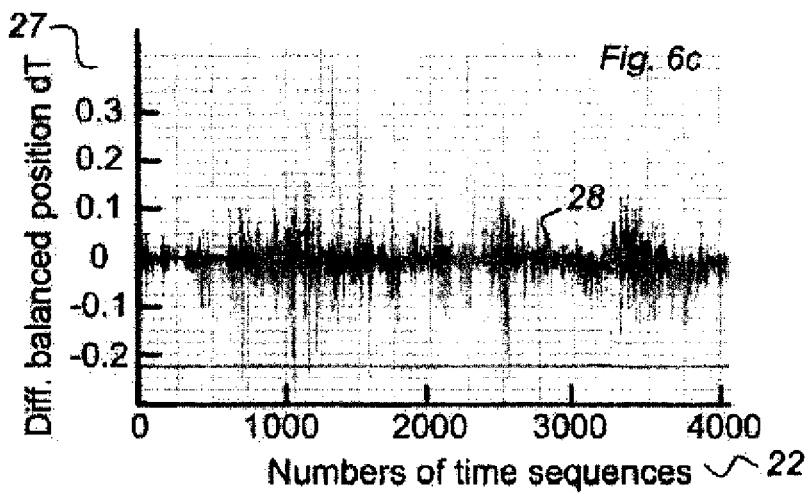

Sheet 10 of 12, Fig. 10b should appear as follows:

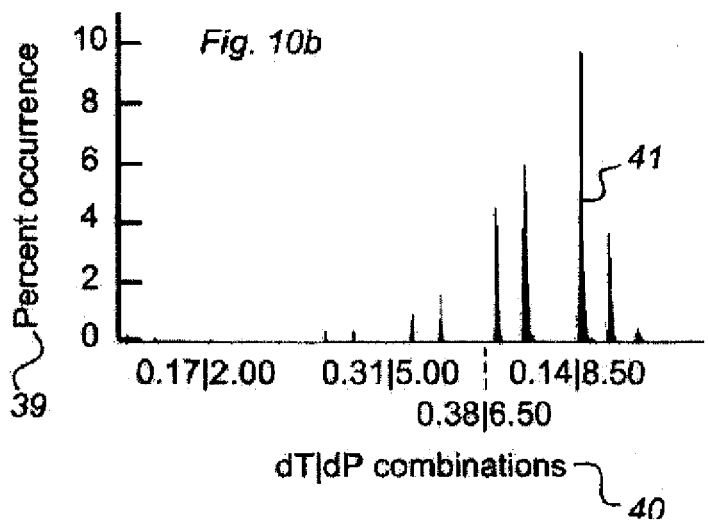

CERTIFICATE OF CORRECTION (continued)

U.S. Pat. No. 7,559,898 B2

Figure 11A:
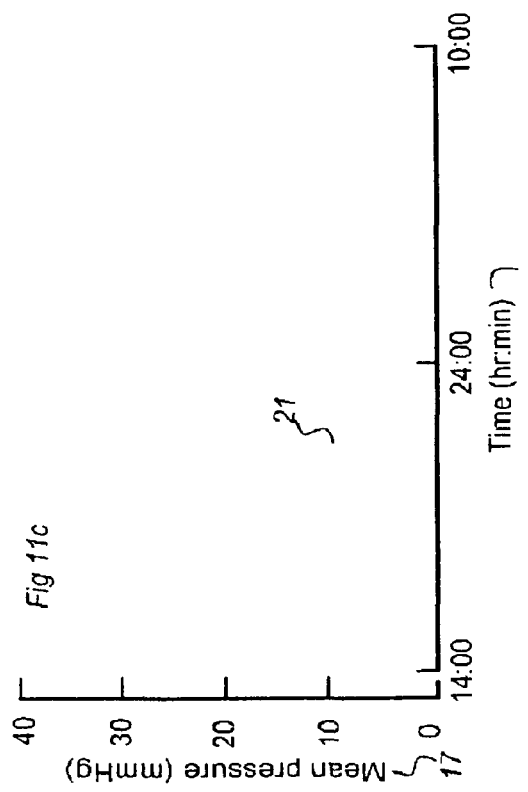
FIG. 11 shows trend plots of absolute mean intracranial pressure for two individuals (a, c), and trend plots (b, d) of weighted values (referred to as predicted mean pressure) of balanced position of amplitude and latency combinations within said time sequences.

In the Drawings:

Sheet 11 of 12, Fig. 11a should appear as follows:

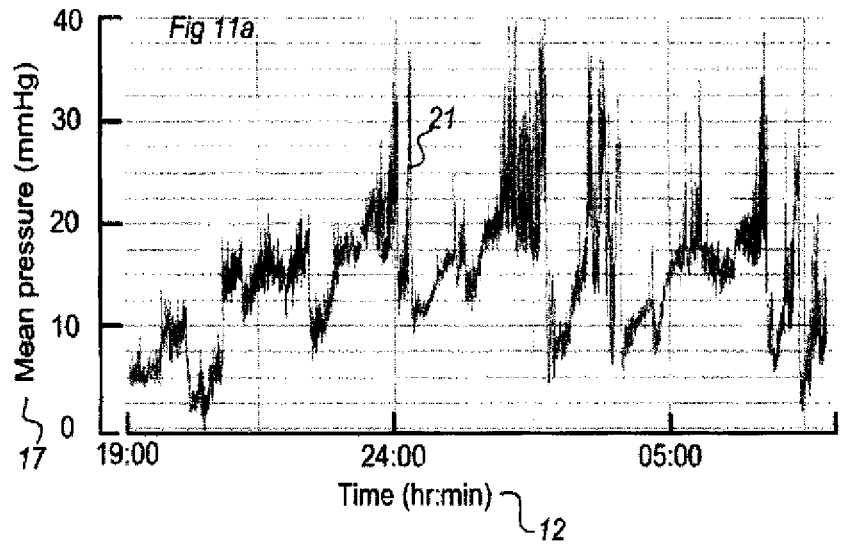

Figure 11B:
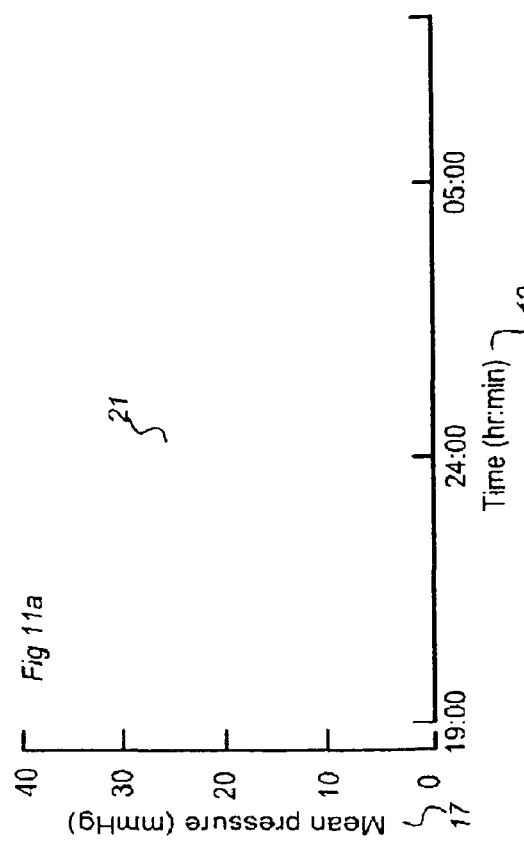

Sheet 11 of 12, Fig. 11b should appear as follows:

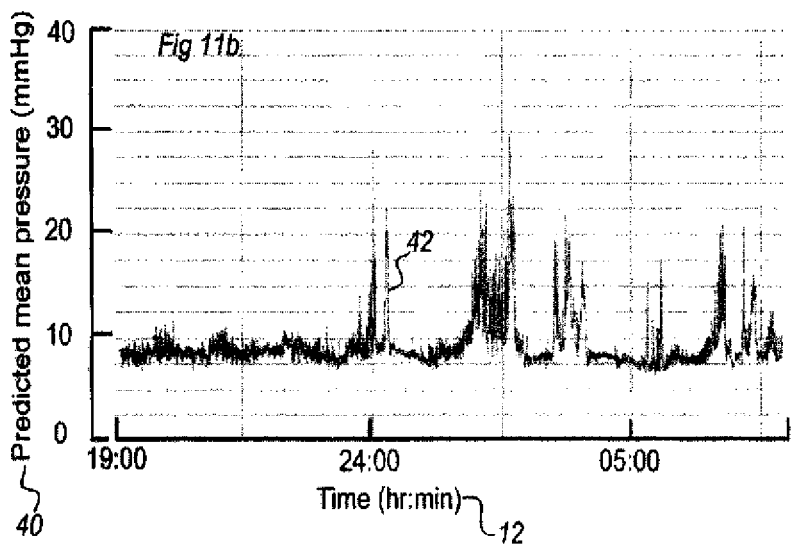

Figure 11C:
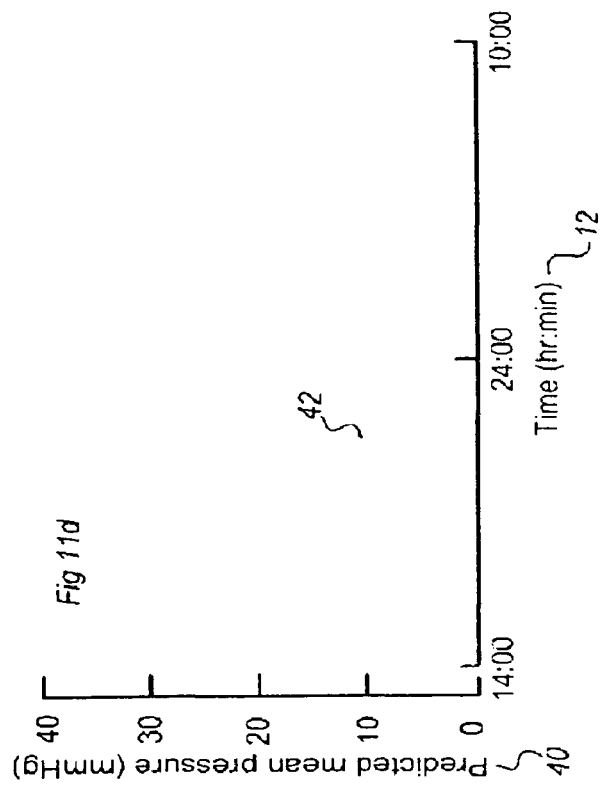
Figure 11D:
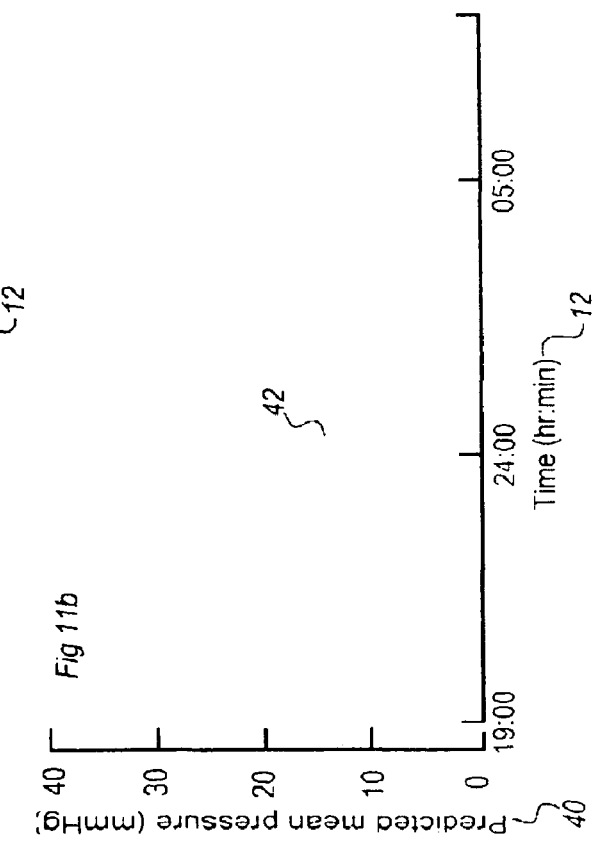

In the Drawings:

Sheet 11 of 12, Fig. 11c should appear as follows:
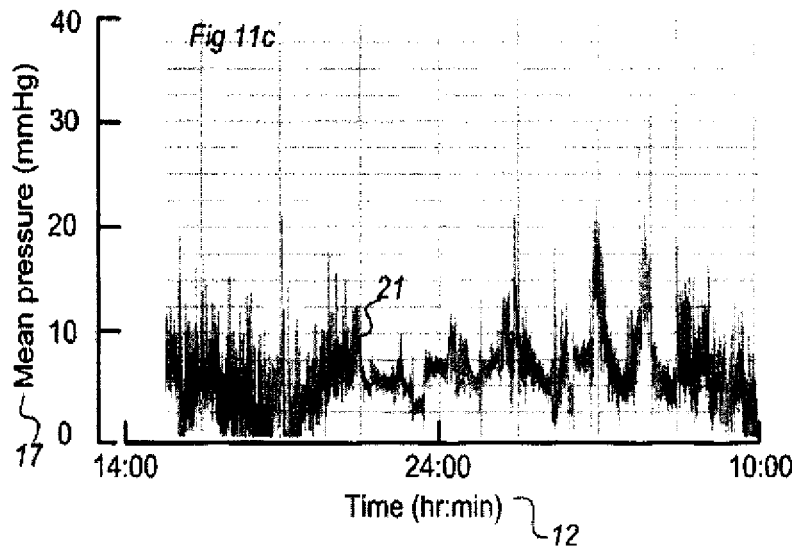
Sheet 11 of 12, Fig. 11d should appear as follows:
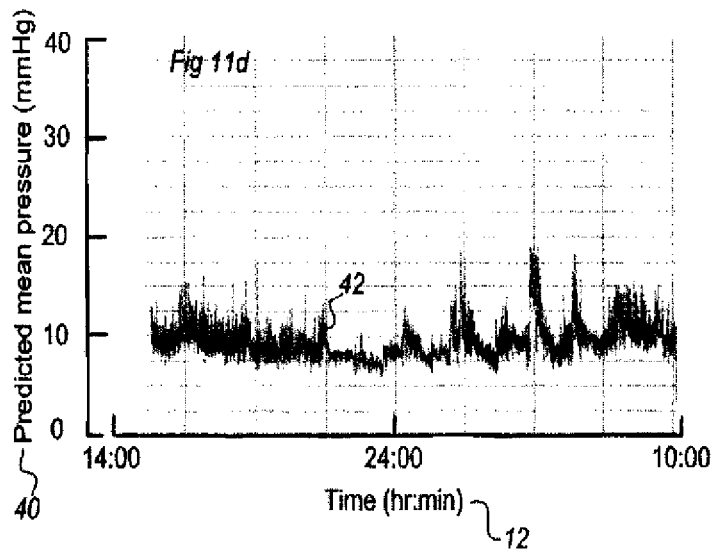
At column 1, lines 20-21:
"claims 1 and 94." should read --claim 1.--.
At column 1, line 36:
"shown oil the scope" should read --shown on the scope--.
At column 5, line 10:

"tonomtery" should read --tonometry--.

At column 35, line 67:

"how tile sensor" should read --how the sensor--.

In the Claims:

In Claim 17, lines 2 and 3:

"AP/ΔT" should read --ΔP/ΔT-- and "amplitude AP" should read --amplitude ΔP--.

In Claim 30, line 63:

"minimumlmaximum" should read --minimum/maximum--.

In Claim 63, line 32:

"$P_{max}$" should read --$P_{min}$--.

In Claim 81, lines 27, 29, 32, 38, 43, 47, 48, and 52:

"one or said" should read --one of said--.